(12) United States Patent
Urbanski et al.

(10) Patent No.: US 6,653,478 B2
(45) Date of Patent: Nov. 25, 2003

(54) SUBSTITUTED BENZIMIDAZOL-2-ONES AS VASOPRESSIN RECEPTOR ANTAGONISTS AND NEUROPEPTIDE Y MODULATORS

(75) Inventors: Maud J. Urbanski, Flemington, NJ (US); Joseph W. Gunnet, Jr., Flemington, NJ (US); Keith T. Demarest, Flemington, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/047,841

(22) Filed: Oct. 23, 2001

(65) Prior Publication Data

US 2003/0073842 A1 Apr. 17, 2003

Related U.S. Application Data

(60) Provisional application No. 60/243,817, filed on Oct. 27, 2000.

(51) Int. Cl.[7] ............... C07D 401/04; A61K 31/454
(52) U.S. Cl. .............. 546/199; 546/187; 546/199; 514/326; 514/322
(58) Field of Search .................. 546/187; 514/326

(56) References Cited

U.S. PATENT DOCUMENTS

| | | |
|---|---|---|
| 5,585,394 A | 12/1996 | Di Malta et al. |
| 5,849,780 A | 12/1998 | Di Malta et al. |

FOREIGN PATENT DOCUMENTS

| | | |
|---|---|---|
| WO | WO 95/02405 A1 | 1/1995 |
| WO | WO 97/40035 A1 | 10/1997 |
| WO | WO 98/11128 A1 | 3/1998 |
| WO | WO 98/44921 A1 | 10/1998 |
| WO | WO 98/44922 A1 | 10/1998 |
| WO | WO 98/45285 A1 | 10/1998 |
| WO | WO 99/52875 A1 | 10/1999 |
| WO | WO 99/64401 A2 | 12/1999 |
| WO | WO 00/18764 A1 | 4/2000 |
| WO | WO 00/18764 * | 4/2000 ............ 546/187 |
| WO | WO-00/18764 * | 4/2000 ............ 546/187 |
| WO | WO 00/26203 A1 | 5/2000 |

OTHER PUBLICATIONS

Albright, J. Donald and Chan, Peter S.; "Recent Advances in the Discovery and Development of Vasopressin Antagonists: Peptide and Nonpeptide V1a and V2 Receptor Antagonists" Current Pharmaceutical Design, 1997, 3, 615–632 1997 Bentham Science Publishers B.V.

CAPLUS accession No. 2000:227655, # 24 of 37, WO 00/18764 listing of RN numbers.*

* cited by examiner

Primary Examiner—Alan L. Rotman
Assistant Examiner—Janet L Coppins

(57) ABSTRACT

The invention is directed to substituted benzimidazol-2-ones of Formula I,

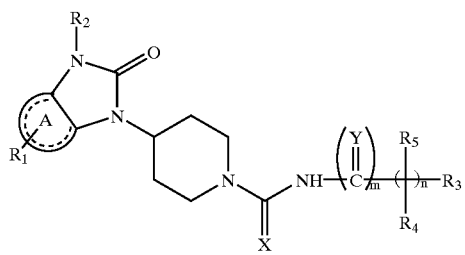

wherein A, X, Y, m, n, $R_1$, $R_2$, $R_3$, $R_4$, and $R_5$ are as described in the specification, which are useful as vasopressin receptor antagonists or Neuropeptide Y Modulators for treating conditions such as aggression, obsessive-compulsive disorders, hypertension, dysmenorrhea, congestive heart failure/cardiac insufficiency, coronary vasospasm, cardiac ischemia, liver cirrhosis, renal vasospasm, renal failure, edema, ischemia, stroke, thrombosis, water retention, nephrotic syndrome, central nervous injuries, obesity, anorexia, hyperglycemia, diabetes, anxiety, depression, asthma, memory loss, sexual dysfunction, disorders of sleep and other circadian rhythms, and Cushing's disease.

23 Claims, No Drawings

SUBSTITUTED BENZIMIDAZOL-2-ONES AS VASOPRESSIN RECEPTOR ANTAGONISTS AND NEUROPEPTIDE Y MODULATORS

CROSS REFERENCE TO RELATED APPLICATION

This application claims priority from U.S. Ser. No. 60/243,817, filed Oct. 27, 2000.

FIELD OF THE INVENTION

This invention relates to novel substituted benzimidazol-2-ones. More particularly, the compounds of the present invention modulate the binding of the peptide hormone vasopressin and neuropeptide Y to their respective receptors and are therefore useful for treating conditions involving increased vascular resistance, cardiac insufficiency, and disorders of energy metabolism.

BACKGROUND OF THE INVENTION

Vasopressin is a nonapeptide hormone that is secreted primarily from the posterior pituitary gland. The hormone effects its actions through the vascular V-1 and renal V-2 receptor subtypes. The functions of vasopressin include contraction of uterine, bladder, and smooth muscle; stimulation of glycogen breakdown in the liver; induction of platelet aggregation; release of corticotropin from the anterior pituitary and stimulation of renal water reabsorption. As a neurotransmitter within the central nervous system (CNS), vasopressin can affect aggressive behavior, sexual behavior, the stress response, social behavior and memory. The V-1a receptor mediates central nervous system effects, contraction of smooth muscle and hepatic glycogenolytic effects of vasopressin, while the V-1b receptor mediates anterior pituitary effects of vasopressin. The V-2 receptor, presumably found only in the kidney, effects the antidiuretic actions of vasopressin via stimulation of adenylate cyclase.

Elevated plasma vasopressin levels appear to play a role in the pathogenesis of congestive heart failure (P. A. Van Zwieten, *Progr. Pharmacol. Clin. Pharmacol.* 1990, 7, 49). As progress toward the treatment of congestive heart failure, nonpeptide vasopressin V-2 receptor antagonists have induced low osmolality aquaresis and decreased peripheral resistance in conscious dogs with congestive heart failure (H. Ogawa, *J. Med. Chem.* 1996, 39, 3547). In certain pathological states, plasma vasopressin levels may be inappropriately elevated for a given osmolality, thereby resulting in renal water retention and hyponatremia. Hyponatremia, associated with edematous conditions (cirrhosis, congestive heart failure, renal failure), can be accompanied by the syndrome of inappropriate secretion of antidiuretic hormone (SIADH). Treatment of SIADH-compromised rats with a vasopressin V-2 antagonist has corrected their existing hyponatremia (G. Fujisawa, *Kidney Int.* 1993, 44(1), 19). Due in part to the contractile actions of vasopressin at its V-1 receptor in the vasculature, vasopressin V-1 antagonists have reduced blood pressure as a potential treatment for hypertension as well. Thus, vasopressin receptor antagonists are useful as therapeutics in the conditions of hypertension, congestive heart failure/cardiac insufficiency, coronary vasospasm, cardiac ischemia, liver cirrhosis, renal vasospasm, renal failure, cerebral edema and ischemia, stroke, thrombosis, and water retention.

Several non-peptide arginine vasopressin (AVP) antagonists have been reported. One of the V1a selective antagonists is known as OPC 21268 (see J. Donald Albright and P. S. Chan, Current Pharm. Design, 1997, 3, 615–632),

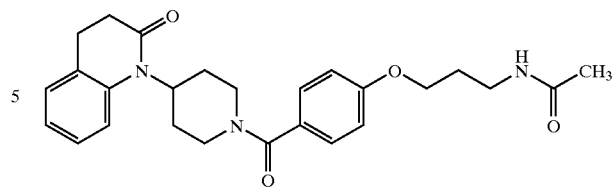

OPC 21268 which is stated to be only active in rat with no activity when tested for binding to human V1a receptor.

U.S. Pat. Nos. 5,849,780 and 5,585,394, both to Malta et. al., show compounds of the following structures, respectively:

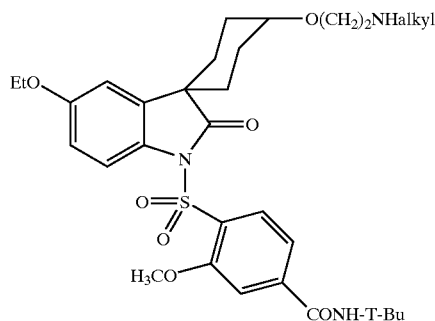

SR-121463A

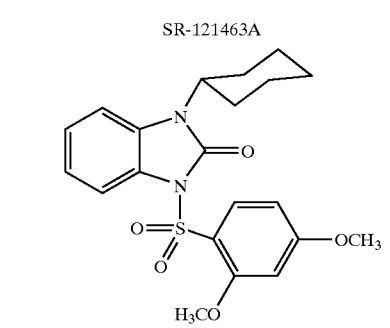

Sr-121463A is stated to be a potent selective orally active V2 receptor antagonist.

Neuropeptide Y (NPY) is a 36 residue, amidated polypeptide widely present in both the central and peripheral nervous systems. It is also present in the cardiovascular system, platelets, endothelium, adrenal medulla, pancreas, kidney and other organs. NPY binds to a number of G-protein coupled receptors such as Y1, Y2, and Y3. The Y1 receptor is stimulated by NPY or PYY (Peptide YY) and believed to be the major vascular receptor. The Y2 receptor is stimulated by C-terminal fragments of NPY or PYY and is abundantly expressed both centrally and peripherally. Present in adrenal medulla, heart, and brain stem, Y3 is exclusively responsive to NPY. Other subtypes of this receptor family are also known to exist. NPY has a number of biological effects. Intranasal administration of NPY reduces nasal airway resistance and vascular permeability. NPY also plays an important role in modulating the cardiovascular system, behavior, anxiety and the secretion of certain hormones; it contributes to the central and peripheral control of blood pressure, the regulation of feeding behavior, obesity, diabetes and psychiatric disorders.

It has been reported that Y1 agonists cause an increase in blood pressure as well as feeding behavior. Y2 agonists/antagonists, on the other hand, can modulate neurotransmitter release.

SUMMARY OF THE INVENTION

The present invention is directed to compounds represented by the following Formula I:

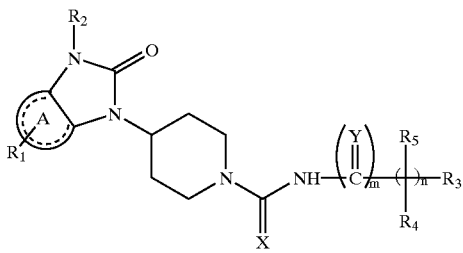

wherein

A is aryl or heteroaryl having 0–4 heteroatoms selected from N, O, and S;

X is selected from S, O, NH, and NCN;

Y is S or O;

$R_1$ is 1–3 groups selected from hydrogen, alkyl, substituted alkyl, halogen, nitro, methylenedioxy, nitrile, —$OR^a$, —$NHR^a$, —$NR^aR^b$, —$S(O)_pR^a$, —$N(R^a)C(O)R^b$, —$C(O)OR^a$, —$C(O)NR^aR^b$, —$SO_2NR^aR^b$, —$N(R^a)SO_2R^b$, $N(R^a)C(O)NR^a$, and $NHCOOR^a$, wherein $R^a$ and $R^b$ are independently selected from the group consisting of hydrogen, alkyl, substituted alkyl, aryl, substituted aryl, heterocyclyl, substituted heterocyclyl, heteroaryl, and substituted heteroaryl;

$R_2$ is selected from hydrogen, alkyl, and substituted alkyl;

$R_3$ is selected from hydrogen, alkyl, substituted alkyl, benzhydryl, aryl, substituted aryl, heteroaryl, substituted heteroaryl, heterocyclyl, substituted heterocyclyl, —$C(O)OR^c$, and —$C(O)NR^cR^d$, wherein $R^c$ and $R^d$ are independently selected from hydrogen, alkyl, substituted alkyl, aryl, substituted aryl, heteroaryl, substituted heteroaryl, heterocyclyl, and substituted heterocyclyl, or $NR^cR^d$ may be taken together to form a group selected from heteroaryl, substituted heteroaryl, heterocyclyl, and substituted heterocyclyl;

$R_4$ and $R_5$ are independently selected from hydrogen, alkyl, alkyl substituted with aryl or heteroaryl, phenyl, substituted phenyl, or $R_4$ and $R_5$ are non-existent when n is 0;

p is from 0 to 2;

n is 0 or 1; and m is 0 or 1, with the proviso that when m is 0, X is O, and $R_3$ is selected from heteroaryl, substituted heteroaryl, —$C(O)OR^c$, and —$C(O)NR^cR^d$ wherein $R^c$ and $R^d$ are independently selected from alkyl, substituted alkyl, aryl, substituted aryl, heteroaryl, substituted heteroaryl, heterocyclyl, and substituted heterocyclyl, or $NR^cR^d$ may be taken together to form a group selected from heteroaryl, substituted heteroaryl, heterocyclyl, and substituted heterocyclyl, then n is 0;

or an optical isomer, enantiomer, diastereomer, racemate thereof, or a pharmaceutically acceptable salt thereof.

The compounds of the present invention are vasopressin receptor antagonists which are useful in disease states of inner ear disorders, aggression, obsessive-compulsive disorders, hypertension, hyperglycemia, dysmenorrhea, congestive heart failure/cardiac insufficiency, coronary vasospasm, cardiac ischemia, liver cirrhosis, renal vasospasm, renal failure, cerebral edema and ischemia, stroke, thrombosis, water retention, nephrotic syndrome, central nervous injuries, diabetes, anxiety, depression, stress, and/or Cushing's disease.

The compounds of the present invention are also Neuropeptide Y modulators which are useful in disease states of hypertension, congestive heart failure/cardiac insufficiency, obesity, diabetes, anorexia, hyperglycemia, anxiety, depression, asthma, memory loss, sexual dysfunction, and disorders of sleep and other circadian rhythms.

An embodiment of the invention is a method of treating a condition associated with vasopressin receptor activity or Neuropeptide Y receptor activity in a subject in need thereof comprising administering to the subject a therapeutically effective amount of any of the compounds or pharmaceutical compositions thereof.

An embodiment of the invention is a method of treating a condition associated with Neuropeptide Y receptor activity in a subject in need thereof comprising administering to the subject a therapeutically effective amount of any of the compounds or pharmaceutical compositions thereof.

Another embodiment of the invention is a method of inhibiting the onset of a condition associated with vasopressin receptor activity or Neuropeptide Y receptor activity in the subject, which comprises administering to the subject a prophylactically effective dose of a pharmaceutical composition of a compound of Formula I.

Further exemplifying the invention is the method of treating obesity, diabetes, anxiety, depression, asthma, or hypertension, wherein the therapeutically effective amount of the compound is about 1 to about 30 mg/kg/day.

Still further exemplifying the invention is the method of inhibiting the onset of obesity, diabetes, anxiety, depression, asthma, or hypertension, wherein the prophylactically effective amount of the compound is about 1 to about 30 mg/kg/day.

An additional illustration of the invention is a method of treating a condition selected from aggression, obsessive-compulsive disorders, hypertension, dysmenorrhea, congestive heart failure/cardiac insufficiency, coronary vasospasm, cardiac ischemia, liver cirrhosis, renal vasospasm, renal failure, edema, ischemia, stroke, thrombosis, water retention, nephrotic syndrome, central nervous injuries, obesity, anorexia, hyperglycemia, diabetes, anxiety, depression, asthma, memory loss, sexual dysfunction, disorders of sleep and other circadian rhythms, and Cushing's disease. Preferably, the therapeutically effective amount of the compound administered for treating any of these conditions is about 1 to about 30 mg/kg/day.

Also included in the invention is the use of any of the compounds described above for the preparation of a medicament for treating a condition selected from aggression, obsessive-compulsive disorders, hypertension, dysmenorrhea, congestive heart failure/cardiac insufficiency, coronary vasospasm, cardiac ischemia, liver cirrhosis, renal vasospasm, renal failure, edema, ischemia, stroke, thrombosis, water retention, nephrotic syndrome, central nervous injuries, obesity, anorexia, hyperglycemia, diabetes, anxiety, depression, asthma, memory loss, sexual dysfunction, disorders of sleep and other circadian rhythms, and Cushing's disease.

DETAILED DESCRIPTION OF THE INVENTION

The present invention provides nonpeptide substituted benzimidazol-2-one compounds which are useful as antagonists of vasopressin and/or modulators of Neuropeptide Y activity. Particularly, these compounds inhibit the binding of vasopressin to V-1a, V-1b, and/or V-2 receptors as well as the binding of Neuropeptide Y to the varied Neuropeptide Y receptors. The compounds of this invention also inhibit vasopressin-induced intracellular calcium mobilization in transfected HEK-293 cells expressing human V-1a or V-1b receptors and/or inhibit vasopressin-induced cAMP accumulation in transfected HEK-293 cells expressing human V-2 receptors.

More particularly, the present invention is directed to compounds of Formula I:

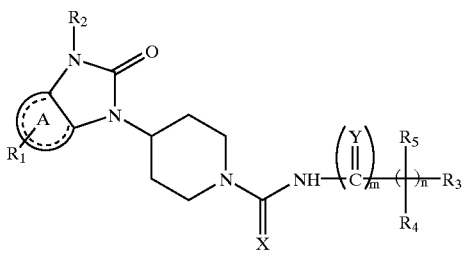

I wherein
A is aryl or heteroaryl having 0–4 heteroatoms selected from N, O, and S;
X is selected from S, O, NH, and NCN;
Y is S or O;
$R_1$ is 1–3 groups selected from hydrogen, alkyl, substituted alkyl, halogen, nitro, methylenedioxy, nitrile, —$OR^a$, —$NHR^a$, —$NR^aR^b$, —$S(O)_pR^a$, —$N(R^a)C(O)R^b$, —$C(O)OR^a$, —$C(O)NR^aR^b$, —$SO_2NR^aR^b$, —$N(R^a)SO_2R^b$, $N(R^a)C(O)NR^a$, and $NHCOOR^a$, wherein $R^a$ and $R^b$ are independently selected from the group consisting of hydrogen, alkyl, substituted alkyl, aryl, substituted aryl, heterocyclyl, substituted heterocyclyl, heteroaryl, and substituted heteroaryl;
$R_2$ is selected from hydrogen, alkyl, and substituted alkyl;
$R_3$ is selected from hydrogen, alkyl, substituted alkyl, benzhydryl, aryl, substituted aryl, heteroaryl, substituted heteroaryl, heterocyclyl, substituted heterocyclyl, —$C(O)OR^c$, and —$C(O)NR^cR^d$, wherein $R^c$ and $R^d$ are independently selected from hydrogen, alkyl, substituted alkyl, aryl, substituted aryl, heteroaryl, substituted heteroaryl, heterocyclyl, and substituted heterocyclyl, or $NR^cR^d$ may be taken together to form a group selected from heteroaryl, substituted heteroaryl, heterocyclyl, and substituted heterocyclyl;
$R_4$ and $R_5$ are independently selected from hydrogen, alkyl, alkyl substituted with aryl or heteroaryl, phenyl, substituted phenyl, or $R_4$ and $R_5$ are non-existent when n is 0;
p is from 0 to 2;
n is 0 or 1; and
m is 0 or 1, with the proviso that when m is 0, X is O, and $R_3$ is selected from heteroaryl, substituted heteroaryl, —$C(O)OR^c$, and —$C(O)NR^cR^d$ wherein $R^c$ and $R^d$ are independently selected from alkyl, substituted alkyl, aryl, substituted aryl, heteroaryl, substituted heteroaryl, heterocyclyl, and substituted heterocyclyl, or $NR^cR^d$ may be taken together to form a group selected from heteroaryl, substituted heteroaryl, heterocyclyl, and substituted heterocyclyl, then n is 0;
or an optical isomer, enantiomer, diastereomer, racemate thereof, or a pharmaceutically acceptable salt thereof.

The substituted benzimidazol-2-one compounds of the present invention are vasopressin receptor antagonists. In a preferred embodiment, the compounds are orally active. As demonstrated by the results of the pharmacological studies described hereinafter, the compounds show the ability to block vasopressin binding to recombinant V-1a, V-1b, and/or V-2, and therefore are useful as therapeutics in or prophylactics against conditions such as inner ear disorders, aggression, obsessive-compulsive disorders, hypertension, hyperglycemia, dysmenorrhea, congestive heart failure/cardiac insufficiency, coronary vasospasm, cardiac ischemia, liver cirrhosis, renal vasospasm, renal failure, edema, ischemia, stroke, thrombosis, water retention, nephrotic syndrome, stress, and central nervous injuries.

The substituted benzimidazol-2-one compounds of the present invention are also Neuropeptide Y receptor modulators. In a preferred embodiment, the compounds are orally active. The compounds show the ability to modulate the binding of Neuropeptide Y to Neuropeptide Y receptors, and therefore are useful as therapeutics in or prophylactics against conditions such as obesity, anorexia, diabetes, hyperglycemia, anxiety, depression, asthma, memory loss, sexual dysfunction, and disorders of sleep and other circadian rhythms.

In particular, compounds of Formula I, wherein A is phenyl or substituted phenyl are embodiments of the present invention. Compounds of Formula I wherein X is S or N are further embodiments of the present invention.

Compounds of Formula I, wherein $R_2$ is alkyl substituted with one or more groups selected from cycloalkyl, aryl, —$NHC(NH)NR^cR^d$, —$NR^cR^d$, —$C(O)OR^c$, —$OR^c$, —$NHC(O)R^c$, and —$C(O)NR^cR^d$, wherein $R^c$ and $R^d$ are independently selected from hydrogen, alkyl, substituted alkyl, aryl, substituted aryl, heteroaryl, substituted heteroaryl, heterocyclyl, and substituted heterocyclyl, or $NR^cR^d$ may be taken together to form a group selected from heteroaryl, substituted heteroaryl, heterocyclyl, and substituted heterocyclyl, are also embodiments of the present invention. More particularly X is S and $R_3$ is aryl or substituted aryl.

Compounds of Formula I, wherein A is aryl, X is S, $R_2$ is substituted alkyl, m is 0, n is 1, $R_3$ and $R_4$ are both aryl, and $R_5$ is H, are particular embodiments of the present invention.

More specifically, the following compounds are particular embodiments of the present invention:
1-piperidinecarbothioamide, 4-[3-[3-(cyclohexylmethyl-amino)propyl]-2,3-dihydro-2-oxo-1H-benzimidazol-1-yl]-N-(diphenylmethyl)-;
1-piperidinecarbothioamide, 4-[3-[3-(3,5-dimethyl-1-piperidinyl)propyl]-2,3-dihydro-2-oxo-1H-benzimidazol-1-yl]-N-(diphenylmethyl)-;
1-piperidinecarbothioamide, 4-[2,3-dihydro-2-oxo-3-[3-(1-piperidinyl)propyl]-1H-benzimidazol-1-yl]-N-(diphenylmethyl)-;
1-piperidinecarbothioamide, 4-[3-[3-(dimethylamino)propyl]-2,3-dihydro-2-oxo-1H-benzimidazol-1-yl]-N-(diphenylmethyl)-;
1-piperidinecarbothioamide, 4-[2,3-dihydro-2-oxo-3-[3-(1-pyrrolidinyl)propyl]-1H-benzimidazol-1-yl]-N-(diphenylmethyl)-;
1-piperidinecarbothioamide, 4-[3-(2-aminoethyl)-2,3-dihydro-2-oxo-1H-benzimidazol-1-yl]-N-(diphenylmethyl)-;
1-piperidinecarbothioamide, 4-[3-[3-[(aminoiminomethyl)amino]propyl]-2,3-dihydro-2-oxo-1H-benzimidazol-1-yl]-N-(diphenylmethyl)-;
1-piperidinecarbothioamide, 4-[3-(4-aminobutyl)-2,3-dihydro-2-oxo-1H-benzimidazol-1-yl]-N-(diphenylmethyl)-;

1-piperidinecarbothioamide, 4-[3-(4-aminobutyl)-2,3-dihydro-2-oxo-1H-benzimidazol-1-yl]-N-[(4-chlorophenyl)phenylmethyl]-;

1-piperidinecarbothioamide, 4-[3-(3-aminopropyl)-2,3-dihydro-2-oxo-1H-benzimidazol-1-yl]-N-(diphenylmethyl)-;

1-piperidinecarbothioamide, 4-[3-[2-(diethylamino)ethyl]-2,3-dihydro-2-oxo-1H-benzimidazol-1-yl]-N-(diphenylmethyl)-;

phenylalanine, N-[[4-(2,3-dihydro-2-oxo-1H-benzimidazol-1-yl)-1-piperidinyl]carbonothioyl]-, methyl ester; and 1-piperidinecarbothioamide, 4-(2,3-dihydro-2-oxo-1H-benzimidazol-1-yl)-N-(1,2-diphenylethyl)-.

The compounds of Formula I may be prepared from readily available starting materials in accordance with various known synthetic routes.

The present invention is also directed to intermediates of Formulae 4 and 5,

4

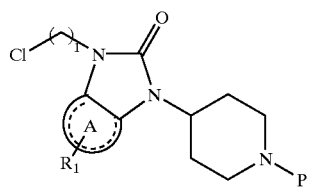

5

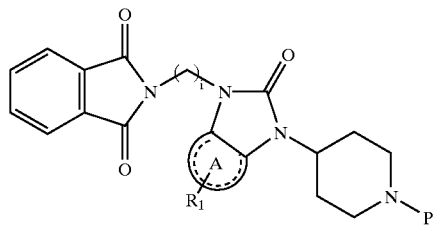

wherein P is hydrogen or a protecting group such as benzyl (Bn) or BOC (t-butyloxycarbonyl), i is an integer from 1 to 8, and A and R₁ are as described hereinabove.

The compounds of the present invention may also be present in the form of a pharmaceutically acceptable salt or salts. For use in medicine, the salt or salts of the compounds of this invention refer to non-toxic "pharmaceutically acceptable salt or salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative basic/cationic salts include, but are not limited to, benzathine, chloroprocaine, choline, diethanolamine, ethylenediamine, meglumine, procaine, aluminum, calcium, lithium, magnesium, potassium, sodium, or zinc.

Where the compounds according to this invention have at least one stereogenic center, they may accordingly exist as enantiomers. Where the compounds possess two or more stereogenic centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

As used herein, "treating" a disorder means eliminating or otherwise ameliorating the cause and/or effects thereof. To "inhibit" or "inhibiting" the onset of a disorder means preventing, delaying or reducing the likelihood of such onset.

Methods are known in the art for determining therapeutically and prophylactically effective doses for the instant pharmaceutical composition. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. The term "prophylactically effective amount" refers to that amount of active compound or pharmaceutical agent that inhibits in a subject the onset of a disorder as being sought by a researcher, veterinarian, medical doctor or other clinician, the delaying of which disorder is mediated by the reduction of increased vascular resistance.

Unless otherwise noted, under standard nomenclature used throughout this disclosure the terminal portion of the designated side chain is described first, followed by the adjacent functionality toward the point of attachment.

Unless otherwise noted, "alkyl" as used herein, whether used alone or as part of a substituent group, include straight and branched chains having 1 to 8 carbon atoms, as well as cycloalkyl groups containing 3 to 8 ring carbons and preferably 5 to 7 ring carbons, or any number within these ranges. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. An alkyl as used herein may be substituted with one or more independent groups including, for example, cycloalkyl, amino, substituted amino, halogen, hydroxy, heterocyclyl, substituted heterocyclyl, heteroaryl, substituted heteroaryl, and/or unsubstituted or substituted aryl such as phenyl or benzyl, —C(O)OR$^e$, OR$^e$, —OC(O)R$^e$, —C(O)NR$^e$R$^f$, —N(R$^e$)C(O)R$^f$, —N(R$^e$)C(O)NR$^f$, or —NHC(NH)NR$^e$R$^f$ wherein R$^e$ and R$^f$ are independently selected from hydrogen, alkyl, halogen, hydroxy, heterocyclyl, substituted heterocyclyl, heteroaryl, substituted heteroaryl, and/or unsubstituted or substituted aryl.

"Heterocyclyl" or "heterocycle" is a 3- to 8-member saturated or partially saturated single or fused ring system which consists of carbon atoms and from one to three heteroatoms selected from N, O and S. The heterocyclyl group may be attached at any heteroatom or carbon atom, which results in the creation of a stable structure. Examples of heterocyclyl groups include, but are not limited to morpholine, thiomorpholine, pyrazolidine, pyrazoline, pyrrolidine, piperidine, and piperazine. "Heterocyclyl" or "heterocycle" may be substituted with one or more independent groups including, but not limited to, H, halogen, oxo, OH, alkyl, substituted alkyl, amino, carboxyl, alkylcarboxyl, and alkoxy.

The term "Ar" or "aryl" as used herein, whether used alone or as part-of a substituent group, refers to an aromatic group such as phenyl, naphthyl, and fluorenyl. When the Ar or aryl group is substituted, it may have one to three substituents which are independently selected from $C_1$–$C_8$ alkyl, substituted $C_1$–$C_8$ alkyl (e.g., trifluoromethyl), $C_1$–$C_8$ alkoxy, substituted $C_1$–$C_8$ alkoxy (e.g., trifluoromethoxy), halogen, cyano, hydroxy, amino, substituted amino (e.g., $C_1$–$C_4$ alkylamino or $C_1$–$C_4$ dialkylamino wherein the alkyl groups can be the same or different), nitro, carboxyl, and unsubstituted, mono-, di- or tri-substituted phenyl wherein the substituents on the phenyl are independently selected from aryl, $C_1$–$C_8$ alkyl, $C_1$–$C_8$ alkoxy, substituted $C_1$–$C_8$ alkyl, fluorinated $C_1$–$C_8$ alkoxy, halogen, cyano, hydroxy, amino, nitro, carboxyl, alkylcarboxyl, alkylamino, dialkylamino and heteroaryl. "Ph" or "PH" denotes phenyl. "Bn" denotes benzyl.

The term "heteroaryl" as used herein represents a stable five or six-membered monocyclic or bicyclic aromatic ring system which consists of carbon atoms and from one to three heteroatoms selected from N, O and S. The heteroaryl group may be attached at any heteroatom or carbon atom, which results in the creation of a stable structure. Examples of heteroaryl groups include, but are not limited to pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl. Prefered heteroaryl groups include pyridinyl, thiophenyl, furanyl, quinolinyl, and

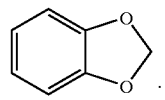

When the heteroaryl group is substituted, the heteroaryl group may have one to three substituents which are independently selected from $C_1$–$C_8$ alkyl, substituted $C_1$–$C_8$ alkyl, halogen, aryl, heteroaryl, alkoxy, alkylamino, dialkylamino, arylamino, nitro, carboxyl, alkylcarboxyl, and hydroxy.

The term "acyl" as used herein, whether used alone or as part of a substituent group, means an organic radical having 2 to 6 carbon atoms (branched or straight chain) derived from an organic acid by removal of the hydroxyl group.

The term "Ac" as used herein, whether used alone or as part of a substituent group, means acetyl.

The term "halogen" shall include iodine, bromine, chlorine and fluorine.

Whenever the term "alkyl", "acyl", or "aryl" or either of their prefix roots appear in a name of a substituent (e.g., aralkyl, dialkylamino), it shall be interpreted as including those limitations given above for "alkyl", "acyl", and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "composition" is intended to encompass a product comprising the specified ingredients in the specified amounts, as well as any product which results, directly or indirectly, from combinations of the specified ingredients in the specified amounts.

The present invention therefore provides a method of treating vascular resistance disorders in a subject in need thereof which comprises administering any of the compounds as defined herein in a quantity effective to treat vascular resistance disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of Formula I or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 1 mg to 30 mg/kg and may be given at a dosage of from about 1 to 30 mg/kg/day (preferred 3 to 15 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a stereogenic HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, Third Edition, John Wiley & Sons, 1999. The protecting groups may be removed at a convenient subsequent stage using methods known from the art.

This invention will be better understood by reference to the schemes and examples that follow, but those skilled in the art will readily appreciate that these are only illustrative of the invention as described more fully in the claims that follow thereafter.

Scheme I

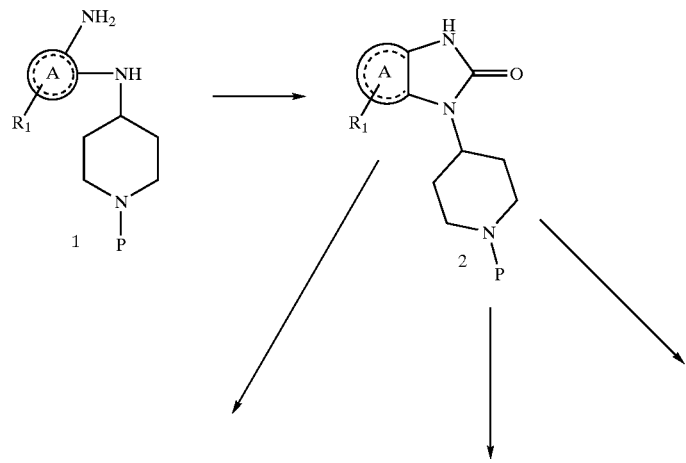

-continued
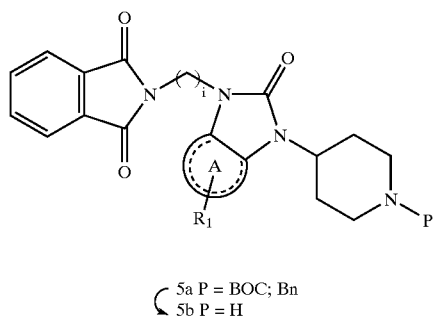
5a P = BOC; Bn
5b P = H
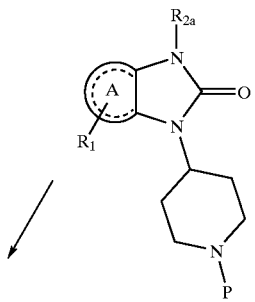
3a P = BOC, Bn
3b P = H
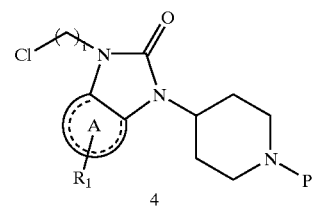
4
NHR$^c$R$^d$
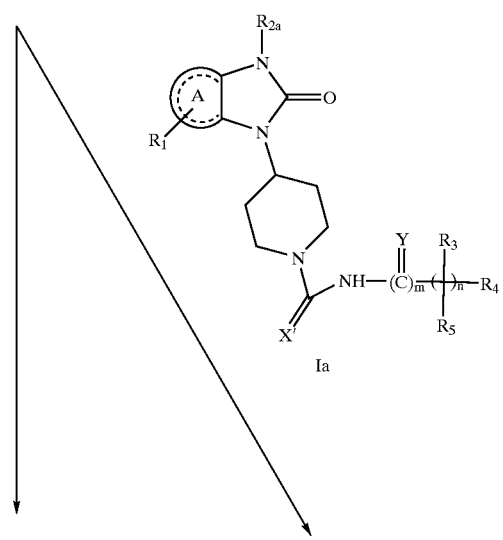
Ia
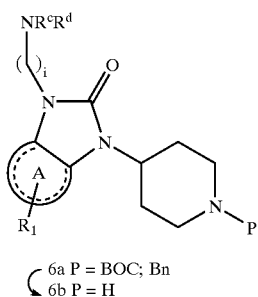
6a P = BOC; Bn
6b P = H
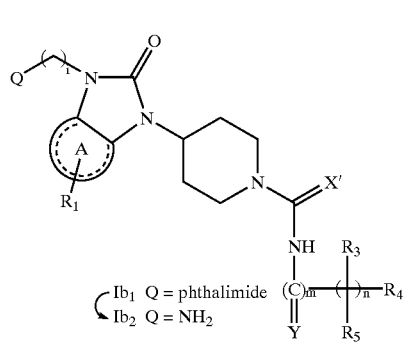
Ib$_1$ Q = phthalimide
Ib$_2$ Q = NH$_2$
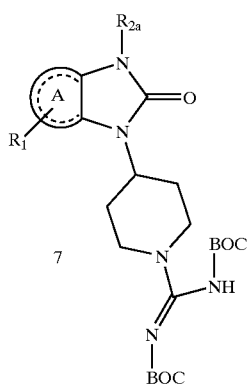
7

-continued

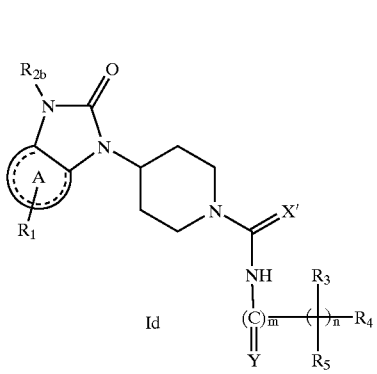

Id

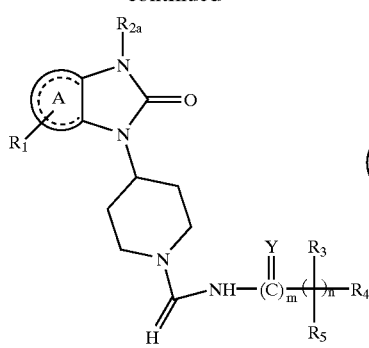

Ie

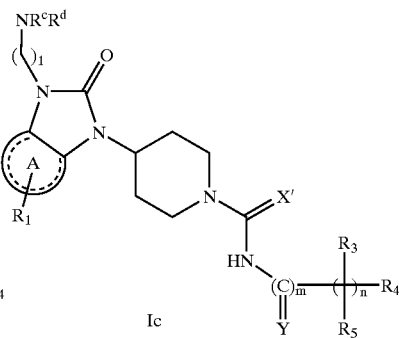

Ic

In accordance with Scheme I, wherein P is hydrogen or a protecting group such as benzyl (Bn) or BOC (t-butyloxycarbonyl), X' is O or S, $R_{2a}$ is selected from hydrogen, alkyl, and alkyl substituted with one or more groups selected from cycloalkyl, halogen, hydroxy, heterocyclyl, substituted heterocyclyl, heteroaryl, substituted heteroaryl, and unsubstituted or substituted aryl, —C(O)OR$^e$, OR$^e$, —OC(O)R$^e$, —C(O)NR$^e$R$^f$, $R_{2b}$ is selected from alkyl substituted with one or more —N(R$^e$)C(O)NR$^f$, —NR$^e$C(O)R$^f$, —NHC(NH)NR$^e$R$^f$ or, i is an integer from 1 to 8, and A, m, n, $R_1$, $R_2$, $R_3$, $R_4$, $R_5$, R$^e$, and R$^d$ are as described hereinabove, benzimidazol-2-ones 2, can be prepared from diamines 1 (which, when A is aryl, may be made by known methods: e.g., J. Med. Chem. 30, 814–819 (1987)), using known conditions and procedures. When A is heteroaryl, compound 1 can be prepared by reductive amination of the 2-nitro heteroarylamines that are known or can be prepared using known procedures (e.g., Heterocycles 38, 529–540 (1994), Arch. Pharm. 314, 564–567 (1981), JACS, 78, 242 (1956)) with commercially available BOC or benzyl protected 4-piperdone followed by reduction of the nitro group under palladium catalyzed hydrogenation reaction conditions. The intermediate 2 can then be heated with an alkyl, benzyl, or dialkylaminoalkyl halide in the presence of a base such as potassium carbonate, cesium carbonate or sodium hydride in a solvent such as dimethyl formamide (DMF), tetrahydrofuran (THF) or acetone to give the corresponding compounds of 3a. 2 can also be treated with a protected phthalimidoalkyl halide or a chloroalkyl halide to give the corresponding compounds of 4 and 5a. The chloride of compound 4 can be further displaced with mono- or di-substituted amines or cyclic amines to give the corresponding compounds of 6a.

The intermediates 3a, 5a, or 6a can be treated with trifluoroacetic acid to remove the protecting group P (P can be either benzyl or BOC) or with α-chloroethylchloroformate or under a hydrogenation condition to remove a benzyl protecting group. This forms the intermediates 3b, 5b, or 6b, respectively. The piperidine nitrogen can then be substituted by treatment with substituted isocyanates or substituted isothiocyanates in an appropriate solvent such as acetonitrile, tetrahydrofuran or methylene chloride to give products Ia, Ib$_1$, and Ic, respectively, wherein Y is O. Compounds Ia, Ib$_1$ and Ic wherein Y is O can then be converted to Ia, Ib$_1$ and Ic wherein Y is S by treatment with $P_2S_5$ with a base such as potassium hydroxide in an appropriate solvent such as toluene or benzene. In cases where the isocyanates or isothiocyanates are not commercially available, they can be prepared by treating the appropriate amines with reagents such as phosgene, thiophosgene or di-2-pyridylthionocabonate. Compound Ib$_1$ can be further treated with hydrazine in solvents such as ethanol (EtOH), methanol (MeOH), or THF to give the free amine Ib$_2$. The amine Ib$_2$ can then be acylated by the addition of acylhalides or anhydrides to give compounds Id. Compound 3b, 5b or 6b can be dissolved in an appropriate solvent such as DMF or THF then heated in the presence of 1,3-bis(tert-butoxycarbonyl)-2-methyl-2-thiopseudourea to afford a substituted guanidinyl intermediate 7. This intermediate 7, dissolved in a solvent such as DMF or THF, can be treated with alkyl or aryl halides under basic conditions (such as in NaH or KH) then treated with trifluoroacetic acid to remove the BOC groups to give compounds Ie wherein either m or n is 1, or $R_3$ is selected from hydrogen, alkyl, substituted alkyl, benzhydryl, heterocyclyl, substituted heterocyclyl, —C(O)OR$^e$, and —C(O)NR$^e$R$^d$.

Scheme II

In accordance with Scheme II, wherein Z is selected from aryl, substituted aryl, heteroaryl, and substituted heteroaryl, Z' is

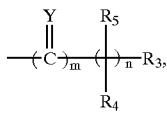

and A, Y, m, n, $R_1$, $R_2$, $R_3$, $R_4$, and $R_5$ are as described above, compounds of formula If can be prepared by heating compound 3b, 5b, or 6b with the appropriate substituted isothiouronium salt 8 (prepared as described in J. Med. Chem. 43, 2362–2370 (2000)) and triethylamine in a solvent such as DMF, THF or acetonitrile. Compounds 3b, 5b, or 6b can also be added to substituted thiourea 9, prepared by reacting sodium cyanamide with the corresponding isothiocyanate, in the presence of a water soluble carbodiimide such as 1-(3-dimethylaminopropyl)-3-ethylcarbodiimide hydrochloride and an appropriate solvent such as DMF and ethanol (procedure described in Tetrahedron Letters, 30, 7313–7316 (1989), to form corresponding compounds of Ig.

The method of treating conditions associated with vasopressin receptor or Neuropeptide Y receptor activity described in the present invention may be carried out using a pharmaceutical composition comprising any of the compounds as defined herein and a pharmaceutically acceptable carrier. The pharmaceutical composition may contain between about 100 mg and 1000 mg, preferably about 100 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms can be in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders of vascular resistance is required.

The daily dosage of the products may be varied over a wide range from 100 to 3000 mg per adult human per day. For oral administration, the compositions are preferably provided in the form of tablets containing the active ingredient in the amount sufficient for the symptomatic adjustment of the dosage to the patient to be treated. An effective amount of the drug is ordinarily supplied at a dosage level of from about 1 mg/kg to about 30 mg/kg of body weight per day. Preferably, the range is from about 3 to about 15 mg/kg of body weight per day, most preferably, from about 5 to about 10 mg/kg of body weight per day. The compounds may be administered on a regimen of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following examples are intended to illustrate the invention but not to limit it. Melting point determinations were done on a Thomas-Hoover capillary melting point apparatus and are uncorrected. Nuclear magnetic resonance ($^1$NMR) spectra were recorded on a Bruker AC300 (300 MHz) spectrometer. Chemical shifts are reported in parts per million (d) downfield relative to tetramethylsilane as standard. Mass spectra (m/z) were obtained on a HP 1100 LC/MSD.

EXAMPLE 1

1-[(N1-Piperidinocarbothioyldiphenylmethylamino)-4-yl]-1,3-dihydro-benzimidazol-2-one (Compound 1)

4-(2-Keto-1-benzimidazolinyl)piperidine (1.0 g, 4.61 mM) and benzhydryl isothiocyanate (1.0 g, 4.4 mM) in acetonitrile (20 ml) was stirred at room temperature for 48 hours. The white solid precipitates were collected and dried to give the product (1.78 g, 87%). m/z (MH$^+$) 443

EXAMPLE 2
1-[(N1-Piperidinocarbothioyl-(2-(4-chlorophenyl)ethylamino)-4-yl]-1,3-dihydro-benzimidazol-2-one (Compound 2)

4-(2-Keto-1-benzimidazolinyl)piperidine was treated as described in Example 1 substituting benzhydryl isothiocyanate with 2-(4-chloropheny) ethyl isothiocyanate to give the product as a white solid (0.28 g, 86%). m.p. 234–236° C.

Anal: Calc'd for C21H23ClN4OS; C, 60.79; H, 5.59; N, 13.50. Found; C, 60.83; H, 5.63; N, 13.33. m/z (MH$^+$) 415

EXAMPLE 3
1-[(N1-Piperidinocarbothioylphenylamino-4-yl]-1,3-dihydro-benzimidazol-2-one (Compound 3)

4-(2-Keto-1-benzimidazolinyl)piperidine was treated as described in Example 1 substituting benzhydryl isothiocyanate with phenyl isothiocyanate to give the product as a white solid. m.p. 250–252° C. m/z (MH$^+$) 353

EXAMPLE 4
1-[N1-Piperidinocarbothioyl-(2-methoxyphenyl)amino-4-yl]-1,3-dihydro-benzimidazol-2-one (Compound 4)

4-(2-Keto-1-benzimidazolinyl)piperidine was treated as described in Example 1 substituting benzhydryl isothiocyanate with 2-methoxyphenyl isothiocyanate to give the product as a white solid. m.p. 196–199° C. m/z (MH$^+$) 383

EXAMPLE 5
1-[(N1-Piperidinocarbothioyl-(4-methoxyphenyl)amino-4-yl]-1,3-dihydro-benzimidazol-2-one (Compound 5)

4-(2-Keto-1-benzimidazolinyl)piperidine was treated as described in Example 1 substituting benzhydryl isothiocyanate with 4-methoxyphenyl isothiocyanate to give the product as a white solid. m.p. 238–243° C. m/z (MH$^+$) 383

EXAMPLE 6
1-[(N1-Piperidinocarbothioyl-(3,4,5-trimethoxyphenyl)amino-4-yl]-1,3-dihydro-benzimidazol-2-one (Compound 6)

4-(2-Keto-1-benzimidazolinyl)piperidine was treated as described in Example 1 substituting benzhydryl isothiocyanate with 3,4,5-trimethoxyphenyl isothiocyanate to give the product as a white solid. m/z (MH$^+$) 443.

EXAMPLE 7
1-[(N1-Piperidinocarbothioyl-(R)-(−)-1-(1-napthyl)ethylamino-4-yl]-1,3-dihydro-benzimidazol-2-one (Compound 7)

4-(2-Keto-1-benzimidazolinyl)piperidine (0.11 g, 0.51 mM) and (R)-(−)-1-(1-naphthyl)ethyl isocyanate (0.099 g, 0.51 mM) in acetonitrile (5 ml) was stirred at room temperature overnight and evaporated in vacuo. The residual semi-solid was diluted with hexane. The solid precipitates were isolated by filtration and dried to give the product. m/z (MH$^+$) 415

EXAMPLE 8
1-[(N1-Piperidinocarbothioylbenzoylamino-4-yl]-1,3-dihydro-benzimidazol-2-one (Compound 8)

4-(2-Keto-1-benzimidazolinyl)piperidine was treated as described in Example 1 substituting benzhydryl isothiocyanate with benzoyl isothiocyanate to give the product m/z (MH$^+$) 381.

EXAMPLE 9
1-[N(Tert-butoxycarbonyl)piperidin-4yl]-1,3-dihydro-benzimidazol-2-one (Compound 9)

Di-tert-butyl dicarbonate (30 g, 0.14M) was slowly added to a cold (0° C.) solution of commercially available 4-(2-keto-1-benzimidazolinyl)piperidine (30 g, 0.14M) in dry tetrahydrofuran (250 ml). The mixture was slowly warmed up to room temperature and stirring was continued for 4 hours. Water (250 ml) was slowly added and stirring was continued overnight. The THF was removed under reduced pressure and the aqueous mixture extracted with ethyl acetate (2×250 ml). The combined ethyl acetate (EtOAc) extracts were washed with brine and dried over MgSO$_4$. The solvent was removed under reduced pressure to give the white solid product (42.2 g, 96%).

EXAMPLE 10
3-Methyl-1-[(N1-Piperidinocarbothioyldiphenylmethylamino)-4-yl]-1,3-dihydro-benzimidazol-2-one (Compound 10)

Sodium hydride (0.06 g, 1.48 mM, 60% dispersion in mineral oil) was added to a mixture of compound 9 as prepared in Example 9 (0.41 g, 1.3 mM) in dry THF (20 ml). The mixture was stirred at room temperature (RT) for one hour and methyl iodide (0.08 ml, 1.3 mM) was added. The mixture was stirred at reflux for one hour, cooled to RT overnight and quenched with water (20 ml). The THF was removed under reduced pressure and the aqueous mixture extracted with ethyl acetate (2×25 ml). The combined EtOAc extracts were dried over MgSO$_4$, evaporated in vacuo and residual semi-solid diluted with methylene chloride (80 ml). The resulting solution was cooled in an ice bath and excess trifluoroacetic acid (3 ml) was added. The mixture was stirred at RT for 2½ hours and a saturated NaHCO$_3$ solution (80 ml) was slowly added. The layers were separated, the organic layer washed again with saturated NaHCO$_3$ (1×80 ml) then dried over MgSO$_4$. The solvent was removed in vacuo and the solid product (0.122 g, 0.52 mM) diluted with acetonitrile. Benzhydryl isothiocyanate was then added and the mixture stirred at RT overnight. The white solid precipitates were collected and dried to give the product. m/z (MH$^+$) 457.

EXAMPLE 11
1-[(N1-Piperidinocarbothioylbenzylamino-4-yl]-1,3-dihydro-benzimidazol-2-one (Compound 11)

4-(2-Keto-1-benzimidazolinyl)piperidine was treated as described in Example 1 substituting benzhydryl isothiocyanate with benzyl isothiocyanate to give the product. m/z (MH$^+$) 367.

EXAMPLE 12
1-[(N1-Piperidinocarbothioyl-2-chlorobenzylamino-4-yl]-1,3-dihydro-benzimidazol-2-one (Compound 12)

4-(2-Keto-1-benzimidazolinyl)piperidine was treated as described in Example 1 substituting benzhydryl isothiocyanate with 2-chlorobenzyl isothiocyanate to give the product. m.p. 181–184° C. m/z (MH$^+$) 401.

EXAMPLE 13
1-[(N1-Piperidinocarbothioyl-2,2-diphenylethylamino-4-yl]-1,3-dihydro-benzimidazol-2-one (Compound 13)

Di(2-pyridyl) thionocarbonate (0.14 g, 0.61 mM) was added to a cold (0° C.) solution of 2,2-diphenylethylamine (0.12 g, 0.61 mM) in acetonitrile (10 ml). The mixture was slowly warmed up to room temperature, stirred at room temperature for 3 hours and 4-(2-keto-1-benzimidazolinyl)piperidine (0.140 g 0.64 mM) was added. The resulting solution was stirred at room temperature overnight, diluted with hexane (5 ml), stirred for an additional hour and filtered to give a solid product. m.p. 230–233° C. m/z (MH$^+$) 457.

EXAMPLE 14
1-[(N1-Piperidinocarbothioyl-2-methoxybenzylamino-4-yl]-1,3-dihydro-benzimidazol-2-one (Compound 14)

4-(2-Keto-1-benzimidazolinyl)piperidine was treated as described in Example 1 substituting benzhydryl isothiocyanate with 2-methoxybenzyl isothiocyanate to give the product. m/z (MH$^+$) 397

EXAMPLE 15
1-[(N1-Piperidinocarbothioyl-(1-naphthalenemethyl)amino-4-yl]-1,3-dihydro-benzimidazol-2-one (Compound 15)

4-(2-Keto-1-benzimidazolinyl)piperidine was treated as described in Example 1 substituting benzhydryl isothiocyanate with 1-naphthalenemethyl isothiocyanate to give the product. m/z (MH$^+$) 417

EXAMPLE 16
1-[(N1-Piperidinocarbothioyl-(3,4-methylenedioxybenzyl)amino-4-yl]-1,3-dihydro-benzimidazol-2-one (Compound 16)

4-(2-Keto-1-benzimidazolinyl)piperidine was treated as described in Example 1 substituting benzhydryl isothiocyanate with 3,4-methylenedioxybenzyl isothiocyanate to give the product. m/z (MH$^+$) 411

EXAMPLE 17
1-[(N1-Piperidinocarbothioyl-2,4-dichlorobenzylamino-4-yl]-1,3-dihydro-benzimidazol-2-one (Compound 17)

4-(2-Keto-1-benzimidazolinyl)piperidine was treated as described in Example 1 substituting benzhydryl isothiocyanate with 2,4-dichlorobenzyl isothiocyanate to give the product. m/z (MH$^+$) 436

EXAMPLE 18
1-[(N1-Piperidinocarbothioyl-2,3-dimethoxybenzylamino-4-yl]-1,3-dihydro-benzimidazol-2-one (Compound 18)

4-(2-Keto-1-benzimidazolinyl)piperidine was treated as described in Example 1 substituting benzhydryl isothiocyanate with 2,3-dimethoxybenzyl isothiocyanate to give the product. m/z (MH$^+$) 427

EXAMPLE 19
1-[(N1-Piperidinocarbothioyldiphenylmethylamino)-4-yl]-3-(2-N-morpholinoethyl)-1,3-dihydro-benzimidazol-2-one (Compound 19)

Compound 9, prepared in Example 9, was treated as described in Example 10 substituting methyl iodide with 4-(2-chloroethyl)morpholine hydrochloride (converted to the free base by washing a mixture of the hydrochloride salt in EtOAc with a saturated NaHCO$_3$ then drying over MgSO$_4$) to give the product. m/z (MH$^+$) 556

EXAMPLE 20
1-[(N1-Piperidinocarbothioyl-3,4,5-trimethoxybenzylamino-4-yl]-1,3-dihydro-benzimidazol-2-one (Compound 20)

4-(2-Keto-1-benzimidazolinyl)piperidine was treated as described in Example 1 substituting benzhydryl isothiocyanate with 3,4,5-trimethoxybenzyl isothiocyanate to give the product. m/z (MH$^+$) 457

EXAMPLE 21
1-[(N1-Piperidinocarbothioyl-(4-ethylbenzylamino)-4-yl]-1,3-dihydro-benzimidazol-2-one (Compound 21)

4-(2-Keto-1-benzimidazolinyl)piperidine was treated as described in Example 13 substituting 2,2-diphenylethylamine with 4-ethylbenzylamine to give the product. m/z (MH$^+$) 409

EXAMPLE 22
1-[(N1-Piperidinocarbothioyl-2-phenethylamino-4-yl]-1,3-dihydro-benzimidazol-2-one (Compound 22)

4-(2-Keto-1-benzimidazolinyl)piperidine was treated as described in Example 1 substituting benzhydryl isothiocyanate with 2-phenethyl isothiocyanate to give the product. m/z (MH$^+$) 381

EXAMPLE 23
1-[(N1-Piperidinocarbothioyl-(2-(3-chlorophenyl)ethylamino)-4-yl]-1,3-dihydro-benzimidazol-2-one (Compound 23)

4-(2-Keto-1-benzimidazolinyl)piperidine was treated as described in Example 1 substituting benzhydryl isothiocyanate with 2-(3-chlorophenyl)ethyl isothiocyanate to give the product. m/z (MH$^+$) 415

EXAMPLE 24
1-[(N1-Piperidinocarbothioyl-(4-dimethyaminobenzylamino)-4-yl]-1,3-dihydro-benzimidazol-2-one (Compound 24)

4-(2-Keto-1-benzimidazolinyl)piperidine was treated as described in Example 13 substituting 2,2-diphenylethylamine with 4-dimethylaminobenzylamine to give the product. m/z (MH$^+$) 410

EXAMPLE 25
1-[(N1-Piperidinocarbothioyltriphenylmethylamino)-4-yl]-1,3-dihydro-benzimidazol-2-one (Compound 25)

4-(2-Keto-1-benzimidazolinyl)piperidine was treated as described in Example 1 substituting benzhydryl isothiocyanate with trityl isothiocyanate to give the product. m/z (MH$^+$) 519

EXAMPLE 26
1-[(N1-Piperidinocarbothioyl-(2-N-morpholinoethylamino)-4-yl]-1,3-dihydro-benzimidazol-2-one (Compound 26)

4-(2-Keto-1-benzimidazolinyl)piperidine was treated as described in Example 1 substituting benzhydryl isothiocyanate with 2-morpholinoethyl isothiocyanate to give the product. m/z (MH$^+$) 390

EXAMPLE 27
1-[(N1-Piperidinocarbothioyl-(4-fluoro-α-methylbenzylamino)-4-yl]-1,3-dihydro-benzimidazol-2-one (Compound 27)

4-(2-Keto-1-benzimidazolinyl)piperidine was treated as described in Example 1 substituting benzhydryl isothiocyanate with 4-fluoro-α-methylbenyl isothiocyanate to give the product. m/z (MH$^+$) 399

EXAMPLE 28
1-[(N1-Piperidinocarbothioyl-(4-chlorobenzylamino)-4-yl]-1,3-dihydro-benzimidazol-2-one (Compound 28)

4-(2-Keto-1-benzimidazolinyl)piperidine was treated as described in Example 1 substituting benzhydryl isothiocyanate with 4-chlorobenzyl isothiocyanate to give the product. m/z (MH$^+$) 401

EXAMPLE 29
1-[(N1-Piperidinocarbothioyl-(3-pyridylmethylamino)-4-yl]-1,3-dihydro-benzimidazol-2-one (Compound 29)

A mixture of 4-(2-keto-1-benzimidazolinyl)piperidine (0.067 g, 0.308 mM), 3-picolyl isothiocyanate hydrobromide (0.071 g, 0.308 mM) and triethylamine (0.04 ml, 0.308) in acetonitrile (5 ml) were stirred at RT overnight. The resulting white solid precipitates were collected and dried to give the product. m/z (MH$^+$) 368

EXAMPLE 30
1-[(N1-Piperidinocarbothioyl-1-methyl-2-(4-chlorophenyl) amino-4-yl]-1,3-dihydro-benzimidazol-2-one (Compound 30)

4-(2-Keto-1-benzimidazolinyl)piperidine was treated as described in Example 13 substituting 2,2-diphenylethylamine with 4-chloroamphetamine hydrochloride to give the product. m/z (MH$^+$) 429

EXAMPLE 31
1-[(N1-Piperidinocarbothioyl-2-(4-nitrophenethyl)amino-4-yl]-1,3-dihydro-benzimidazol-2-one (Compound 31)

4-(2-Keto-1-benzimidazolinyl)piperidine was treated as described in Example 13 substituting 2,2-diphenylethylamine with 4-nitrophenethylamine hydrochloride to give the product. m/z (MH$^+$) 426

EXAMPLE 32
1-[(N1-Piperidinocarbothioyl-1,2-diphenylethylamino-4-yl]-1,3-dihydro-benzimidazol-2-one (Compound 32)

4-(2-Kketo-1-benzimidazolinyl)piperidine was treated as described in Example 13 substituting 2,2-diphenylethylamine with 1,2-diphenethylamine to give the product. m/z (MH$^+$) 457

EXAMPLE 33
1-[(N1-Piperidinocarbothioyl-9-aminofluoren-4-yl]-1,3-dihydro-benzimidazol-2-one (Compound 33)

4-(2-Keto-1-benzimidazolinyl)piperidine was treated as described in Example 13 substituting 2,2-diphenylethylamine with 9-aminofluorene hydrochloride to give the product. m/z (MH$^+$) 441

EXAMPLE 34
1-[(N1-Piperidinocarbothioyl-4-chlorodiphenylmethyl-amino-4-yl]-1,3-dihydro-benzimidazol-2-one (Compound 34)

4-(2-Keto-1-benzimidazolinyl)piperidine was treated as described in Example 13 substituting 2,2-diphenylethylamine with 4-chlorobenzhydrylamine hydrochloride to give the product. m/z (MH$^+$) 478

EXAMPLE 35
1-(N1-Piperidinocarbothioyldiphenylmethylamino-4-yl)-3-(2-diethyaminoethyl)-1,3-dihydrobenzimidazol-2-one (Compound 35)

Compound 9 as prepared in Example 9 was treated as described in Example 10 substituting methyl iodide with N,N-diethylaminoethylchloride to give the product. m/z (MH$^+$) 317

EXAMPLE 36
1-(N1-Piperidinocarbothioyl-(4-fluoro-□-methylbenzyl-amino)-4-yl)-3-(2-diethyaminoethyl)-1,3-dihydrobenzimidazol-2-one (Compound 36)

Compound 9 as prepared in Example 9 was treated as described in Example 35 substituting benzhydryl isothiocyanate with 4-fluoro-α-methylbenyl isothiocyanate to give the product. m/z (MH$^+$) 498.

EXAMPLE 37
1-(N1-Piperidinocarbothioyldiphenylmethylamino-4-yl)-3-benzyl-1,3-dihydrobenzimidazol benzimidazol-2-one (Compound 37)

Compound 9 as prepared in Example 9 was treated as described in Example 10 substituting methyl iodide with benzyl bromide to give the product. m/z (MH$^+$) 533

EXAMPLE 38
1-[(N1-Piperidinocarbothioyl-2-phenpropylamino-4-yl]-1,3-dihydrobenzimidazol-2-one (Compound 38)

4-(2-Keto-1-benzimidazolinyl)piperidine was treated as described in Example 1 substituting benzhydryl isothiocyanate with 2-phenpropyl isothiocyanate to give the product. m/z (MH$^+$) 395

EXAMPLE 39
1-(N1-Piperidinocarbothioyl-2-(4-chlorophenyl)ethyl-amino-4-yl)-3-benzyl-1,3-dihydrobenzimidazol-2-one (Compound 39)

Compound 9 as prepared in Example 9 was treated as described in Example 37 substituting benzhydryl isothiocyanate with 2-(4-chlorophenyl)ethyl isothiocyanate to give the product. m/z (MH$^+$) 506

EXAMPLE 40
1-[(N1-Piperidinocarbothioyl-(2-phenyl-1-L-carboxy-methyl)amino-4-yl]-1,3-dihydrobenzimidazol-2-one (Compound 40)

4-(2-Keto-1-benzimidazolinyl)piperidine was treated as described in Example 1 substituting benzhydryl isothiocyanate with methyl L-2-isothiocyanato-3-phenyl propionate to give the product. m/z (MH$^+$) 439

EXAMPLE 41
1-[(N1-Piperidinocarbothioyl-(2-phenyl-1-L-carboxy) amino-4-yl]-1,3-dihydro-benzimidazol-2-one (Compound 41)

A 6.6N NaOH (0.1 ml) solution was added to a mixture of Compound 40 (0.1 g, 0.228 mM), prepared in Example 40, in methanol (20 ml). The reaction mixture was allowed to stir for five hours then acidified to pH of 2 with concentrated hydrochloric acid. The methanol was removed under reduced pressure and the residual semi-solid diluted with water (10 ml). The mixture was stirred and the white solid precipitates collected by filtration and dried to give the product (0.6 g, 62%). m/z (MH$^+$) 425

EXAMPLE 42
1-(N1-Piperidinocarbothioyl-(2-phenyl-1-L-carboxy-methyl)amino-4-yl)-3-(2-diethyaminoethyl)-1,3-dihydro-benzimidazol-2-one (Compound 42)

Compound 9 as prepared in Example 9, was treated as described in Example 35 substituting benzhydryl isothiocyanate with methyl L-2-isothiocyanato-3-phenyl propionate to give the product. m/z (MH$^+$) 538

EXAMPLE 43
1-(N1-Piperidinocarbothioyl-(2-phenyl-1-L-carboxy) amino-4-yl)-3-(2-diethyaminoethyl)-1,3-dihydrobenzimidazol-2-one (Compound 43)

A solution of Compound 42, prepared in Example 42, was treated as described in Example 41 to give the product. m/z (MH$^+$) 524

EXAMPLE 44
1-[(N1-Piperidinocarbothioyl-(2-phenyl-1-L-acetamidoethylcarbamoyl)amino-4-yl]-1,3-dihydrobenzimidazol-2-one (Compound 44)

A mixture of Compound 41 (0.1 g, 0.24 mM) as prepared in Example 41, N-acetylethylenediamine (0.02 ml, 0.24 mM), 1-(3-dimethylaminopropyl)-3-ethylcarbodiimide hydrochloride (0.11 g, 0.58) and 1-hydroxybenzotriazole hydrate (0.016 g, 0.12 mM) in DMF (20 ml) was stirred at RT overnight and diluted with a 10% NaHCO$_3$ aqueous solution (30 ml). The mixture was extracted with EtOAc (2×50 ml). The combined EtOAc extracts were dried over MgSO$_4$ and evaporated to dryness. The solid residue was diluted with EtOAc and allowed to stand at RT overnight. The solid precipitates were collected and dried to give the product (0.066 g, 55%).

m/z (MH$^+$) 509

EXAMPLE 45
1-[(N1-Piperidinocarbothioyl-1-N-methylpiperazinocarbonyl-2-phenethylamino-4-yl]-1,3-dihydrobenzimidazol-2-one (Compound 45)

Compound 41 as prepared in example 41, was treated as described in Example 44 substituting N-acetylethylenediamine with N-methylpiperazine to give the product. m/z (MH$^+$) 507

EXAMPLE 46
1-[(N1-Piperidinocarbothioyl-1-[(tert-butoxycarbonyl)amino]-2-phenethylamino-4-yl]-1,3-dihydrobenzimidazol-2-one (Compound 46)

Compound 41 as prepared in example 41, was treated as described in Example 44 substituting N-acetylethylenediamine with tert-butyl N-(2-aminoethyl)carbamate to give the product. m/z (MH$^+$) 567

EXAMPLE 47
1-[(N1-Piperidinocarbothioyl-(1-carbamoyl-2-phenylamino-4-yl]-1,3-dihydro-benzimidazol-2-one (Compound 47)

Ammonium hydrogencarbonate (0.061 g, 0.77 mM) was added to a mixture of Compound 41 (0.30 g, 0.70 mM), prepared in Example 41, BOC anhydride (0.17 g, 0.80 mM), and pyridine (0.1 ml) in dioxane (5 ml). The resulting mixture was stirred at RT overnight and H$_2$O (30 ml) was added. The aqueous mixture was extracted with CH$_2$Cl$_2$ (2×30 ml). The combined CH$_2$Cl$_2$ layers were washed with 1N HCl (1×60 ml) then dried over MgSO$_4$. The solvents were removed under reduced pressure and the crude oil purified by chromatography (EM Silica gel 60, 5% MeOH in CH$_2$Cl$_2$) to give the product. m/z (MH$^+$) 424

EXAMPLE 48
1-[(N1-Piperidinocarbothioyl-2-methylphenylamino)-4-yl]-1,3-dihydro-benzimidazol-2-one (Compound 48)

4-(2-Keto-1-benzimidazolinyl)piperidine was treated as described in Example 1 substituting benzhydryl isothiocyanate with 2-methylphenyl isocyanate to give the product (0.16 g, 82%). m/z (MH$^+$) 351

EXAMPLE 49
1-[(N1-Piperidinocarbothioyl-2-phenylphenylamino)-4-yl]-1,3-dihydro-benzimidazol-2-one (Compound 49)

4-(2-Keto-1-benzimidazolinyl)piperidine was treated as described in Example 1 substituting benzhydryl isothiocyanate with 2-phenylphenyl isocyanate to give the product (0.185 g, 55%). m/z (MH$^+$) 413

EXAMPLE 50
1-[(N1-Piperidinocarbothioyl-D-tryptophancarboxymethylamino-4-yl]-1,3-dihydrobenzimidazol-2-one (Compound 50)

Thiophosgene (0.04 ml, 0.51 mM) was added to a cold (0° C.) mixture of D-tryptophan methyl ester hydrochloride (0.10 g, 0.39 mM) and pyridine (0.1 ml, 1.2 mM) in methylene chloride (20 ml). After stirring at 0° C. for an additional two hours, the 4-(2-keto-1-benzimidazolinyl)piperidine (0.085 g, 0.39 mM) was added and the mixture was allowed to stir at RT overnight. The mixture was then washed with H$_2$O (1×20 ml) and the CH$_2$Cl$_2$ layer dried over MgSO$_4$. All solvents were evaporated in vacuo and the residual oil chromatographed (EM silica gel 60; EtOAc) to give the product. m/z (MH$^+$) 478

EXAMPLE 51
1-[(N1-Piperidinocarbothioyl-D-benzylcarboxymethylamino-4-yl]-1,3-dihydrobenzimidazol-2-one (Compound 51)

4-(2-Keto-1-benzimidazolinyl)piperidine was treated as described in Example 50 substituting D-tryptophan methyl ester hydrochloride with D-phenylalanine methyl ester hydrochloride to give the product. m/z (MH$^+$) 439

EXAMPLE 52
1-[(N1-Piperidinocarbothioyl-(2-phenyl-1-L-carboxymethyl)amino-4-yl]-3-(3-N-carbobenzyloxyamino)propyl-1,3-dihydrobenzimidazol-2-one (Compound 52)

To a cold (0° C.) mixture of bromopropylamine hydrobromide (3 g, 13.7 mM) and triethylamine (5 ml, 35.9 mM) and methylene chloride (100 ml) was slowly added benzyl chloroformate (2.3 ml, 13.7 mM). The resulting mixture was slowly warmed up to RT, stirred at RT for 1 hour and H$_2$O (100 ml) was added. The layers were separated and the methylene chloride layer dried over MgSO$_4$. The solvent was removed in vacuo to give an oil. The oil (300 mg, 1.1 mM) was diluted with acetone (50 ml), Compound 9 (0.35 g, 1.1 mM) prepared in Example 9, and K$_2$CO$_3$ (0.3 g, 2.2 mM) was added. The mixture was stirred at reflux overnight, cooled to RT, evaporated in vacuo, and H$_2$O (50 ml) was added. The acetone was removed under reduced pressure and the aqueous mixture extracted with EtOAc (2×60 ml). The combined EtOAc extracts were dried over MgSO$_4$ and evaporated in vacuo to give the Cbz protected intermediate (0.45 g, 81%). The BOC group was removed by treatment of a cold (0° C.) solution of the Cbz protected intermediate (0.45 g, 0.89 mM) in methylene chloride (20 ml) with excess trifluoroacetic acid (2 ml). The mixture was stirred at room temperature overnight and evaporated to dryness. Trituration with diethyl ether gave the desired intermediate as a TFA salt. This intermediate was substituted for 4-(2-keto-1-benzimidazolinyl)piperidine and treated as described in Example 40 to give the product as a solid. m/z (MH$^+$) 630.

EXAMPLE 53
1-(Piperdin-4-yl)-3-(3-phthalimidopropyl)benzimidazol-2-one (Compound 53)

A mixture of Compound 9 (42.2 g, 0.13M), prepared in Example 9, and N-(3-bromopropyl)phthalimide (35 g, 0.13M) were dissolved in DMF (300 ml). Cesium carbonate (100 g, 0.3M) was added in one portion and the resulting heterogenous mixture heated in an 80° C. oil bath for 16 hours. The mixture was cooled to room temperature and the DMF removed under reduced pressure. The residue was poured into ice water (800 ml) and stirred at room temperature overnight. The white solid precipitates were collected and dried to give the desired product (60 g, 92%). The BOC group was removed by treatment of a solution of the compound in methylene chloride (500 ml) with excess trifluoroacetic acid (46 ml, 0.6M). The mixture was stirred at room temperature overnight and evaporated to dryness under reduced pressure. The resulting white solids were washed with diethyl ether and dried to give the desired TFA salt. m.p. 173–175° C. $^1$H NMR (300 MHz, DMSO-d6) δ8.79 (m, 1H; 8.54 (m, 1H); 7.82 (s, 4H); 7.35 (m, 1H); 7.25 (m, 1H); 7.07–6.90 (m, 2H); 4.55 (m, 1H); 3.90 (t, J=7 Hz, 2H); 3.63 (t, J=7 Hz, 2H); 3.42 (m, 2H); 3.15 (m, 2H); 2.60(m, 2H); 2.07 (m, 2H); 1.90 (m, 2H). MS: m/z (MH$^+$) 405

EXAMPLE 54
1-[(N1-Piperidinocarbothioyldiphenylmethylamino)-4-yl]-3-(3-N-phthalimidopropyl)-1,3-dihydrobenzimidazol-2-one (Compound 54)

To a stirred mixture of Compound 53 (46 g, 0.087M), prepared in Example 53, and triethylamine (20 ml, 0.177M in methylene chloride (500 ml) was slowly added benzhydryl isothiocyanate (20 g, 0.087M). The mixture was stirred at room temperature overnight and $H_2O$ (100 ml) was added. The $CH_2Cl_2$ was removed under reduced pressure and an additional 400 ml of $H_2O$ was added. The aqueous mixture was extracted with ethyl acetate (2×500 ml). The combined EtOAc extracts were dried ($MgSO_4$), filtered and evaporated in vacuo to give a semi-solid product. Recrystallization from EtOH gave the product as a white solid (40 g, 71%). m/z ($MH^+$) 630

EXAMPLE 55
1-[(N1-Piperidinocarbothioyldiphenylmethylamino)-4-yl]-3-(3-aminopropyl)-1,3-dihydrobenzimidazol-2-one Monohydrochloride (Compound 57)

To a suspension of Compound 54 (22 g, 0.035M), prepared in Example 54, in EtOH (250 ml) was added anhydrous hydrazine (2 ml, 0.07M). The mixture was stirred at room temperature overnight and evaporated to dryness. The solid residue was diluted with methylene chloride and filtered to remove the phthalhydazide by-product. The supernatant was evaporated in vacuo and flash column chromatographed (EM silica gel 60; 10% MeOH in $CH_2Cl_2$) to give the product (12.2 g, 70%). m/z ($MH^+$) 500. The HCl salt was prepared by the addition of a 1M HCl in $Et_2O$ solution to a mixture of the free base in methanol. The resulting white solid precipitates were collected and dried to give the product (11 g, 85%). m.p. 189–190° C. $^1H$ NMR (300 MHz, DMSO-d6) □8.46(d, J=8.55 Hz, 1H); 7.96 (s, 2H); 7.32 (m, 10H); 7.18–7.02 (m, 4H); 4.92 (d, J=12.9 Hz, 2H); 4.56 (m, 1H); 3.92 (t, J=6.7 Hz, 2H); 3.16 (t, J=12.7 Hz, 2H); 2.82 (t, J=7.2 Hz, 2H); 2.29 (m, 2H), 1.93 (m, 2H); 1.77 (m, 2H). Anal: Cal'd for $C_{29}H_{33}N_5OS$ HCl 3/4H2O; C, 63.41; H,6.51; N,12.75. Found; C 63.42; H,6.32; N,12.61.

EXAMPLE 56
1-[(N1-Piperidinocarbothioyl-(1-L-carboxymethyl-2-phenylamino)-4-yl]-3-(3-phthalimidopropyl)-1,3-dihydrobenzimidazol-2-one (Compound 56)

Compound 53 as prepared in Example 53 was treated as described in Example 54 substituting benzhydryl isothiocyanate with methyl L-2-isothiocyanato-3-phenyl propionate to the give the product. m/z ($MH^+$) 626

EXAMPLE 57
1-[(N1-Piperidinocarbothioyl-(1-L-carboxymethyl-2-phenylamino)-4-yl]-3-(3-aminopropyl)-1,3-dihydrobenzimidazol-2-one Hydrochloride (Compound 57)

Compound 56, as prepared in Example 56, was treated as described in Example 55 to give the product. m/z ($MH^+$) 533

EXAMPLE 58
1-[(N1-Piperidinocarbothioyl-(1-L-carboxymethyl-2-phenylamino)-4-yl]-3-(3-guanidinopropyl)-1,3-dihydrobenzimidazol-2-one (Compound 58)

Compound 57 (0.167 g, 0.33 mM), as prepared in Example 57, 3,5-dimethypyrazole-1-carboxamidine nitrate (0.067 g, 0.33 mM) and triethylamine (0.09 ml, 0.66 mM) were combined in DMF (10 ml) and stirred in a 45° C. oil bath for 16 hr. The DMF was removed under reduced pressure and the-crude product triturated with $Et_2O$. Purification of the resulting semi-solid by column chromatography (EM Silica gel 60; 20% MeOH in $CH_2Cl_2$) afforded the product (0.040 g, 22%). m/z ($MH^+$) 542

EXAMPLE 59
1-[(N1-Piperidinocarbothioyldiphenylmethylamino)-4-yl]-3-(3-guanidinopropyl)-1,3-dihydrobenzimidazol-2-one (Compound 59)

Compound 55, as prepared in Example 55, was substituted for compound 57 and treated as described in Example 58 to the give the product. m/z ($MH^+$) 575.

EXAMPLE 60
1-[(N1-Piperidinocarbothioyldiphenylmethylamino)-4-yl]-3-(2-carboethoxyethyl)-1,3-dihydro-benzimidazol-2-one (Compound 60)

A mixture of Compound 9 (1.1 g, 3.5 mM), as prepared in Example 9, Ethyl 3-bromopropionate (0.5 ml, 3.8 mM) and 2 equivalents of cesium carbonate in acetone was stirred at reflux for 48 hours. Once cooled to RT, $H_2O$ was added and the acetone was removed under reduced pressure. The resulting aqueous mixture was extracted with EtOAc (2×60 ml). The combined EtOAc extracts were dried over $MgSO_4$ and evaporated in vacuo. The resulting semi-solid was diluted with methylene chloride (30 ml), cooled to 0° C. in an ice bath and treated with excess trifluoroacetic acid (3.0 ml). After stirring for 6 hours, saturated $NaHCO_3$ (60 ml) was added and the layers were separated. The aqueous layer was again extracted with $CH_2Cl_2$ (60 ml). The combined $CH_2Cl_2$ layers were dried over $MgSO_4$, and evaporated in vacuo to give a semi-solid. This semi-solid (0.8 g, 2.5 mM) was dissolved in acetonitrile (30 ml) and treated with Benzhydryl isothiocyanate (0.6 g, 2.7 mM). The resulting mixture was stirred at RT overnight, evaporated in vacuo and chromatographed (EM silica gel 60; 10% EtOAc in $CH_2Cl_2$) to give the product. m/z ($MH^+$) 543.

EXAMPLE 61
1-[(N1-Piperidinocarbothioyldiphenylmethylamino)-4-yl]-3-(2-carboxyethyl)-1,3-dihydrobenzimidazol-2-one (Compound 61)

To a suspension of Compound 60 (0.110 g, 0.20 mM), as prepared in Example 60, in MeOH (10 ml) was added (0.15 ml) of a 50% $NaOH/H_2O$ solution. The suspension was stirred at RT till all solids dissolved (16 hrs). The MeOH was removed under reduced pressure and a 1N HCl (20 ml) solution was added. The white solid precipitates were collected by filtration, rinsing several times with water then dried to give the product (0.081 g, 79%). m/z ($MH^+$) 543.

EXAMPLE 62
1-[(N1-Piperidinocarboyl-2-biphenylylamino)-4-yl]-3-(3-aminopropyl)-1,3-dihydro-benzimidazol-2-one hydrochloride (Compound 62)

Compound 53, as prepared in Example 53, was treated as described in Example 54 substituting benzhydryl isothiocyanate with 2-biphenylylisocyanate. The resulting semi-solid product was substituted for Compound 54 then further treated as described in Example 55 to give the product. m/z ($MH^+$) 507.

EXAMPLE 63
1-[(N1-Piperidinocarbothioyldiphenylmethylamino)-4-yl]-3-(2-aminoethyl)-1,3-dihydrobenzimidazol-2-one Hydrochloride (Compound 63)

Compound 9 (1.2 g, 3.77 mM), as prepared in Example 9, and N-(2-bromoethyl) phthalimide (0.9 g, 3.77 mM) were dissolved in DMF (20 ml). Cesium carbonate (2.5 g, 7.5 mMM) was added in one portion and the resulting heterogenous mixture heated in an 80° C. oil bath for 16 hours. The mixture was cooled to RT, and ice H$_2$O (60 ml) was added. The aqueous mixture was extracted with two 80 ml portions of EtOAc. The combined EtOAc extracts were dried (MgSO$_4$) and evaporated in vacuo to give a solid intermediate. The BOC group was removed by treatment of a mixture of the solid intermediate in methylene chloride (30 ml) with excess trifluoroacetic acid (2 ml). The mixture was stirred at room temperature overnight, evaporated to dryness, diluted with EtOAc (80 ml) and washed with saturated NaHCO$_3$ (1×80 ml). The aqueous layer was again extracted with EtOAc (2×80 ml). The combined EtOAc extracts were dried over MgSO$_4$ and evaporated in vacuo to give the product (1.1 g, 75%). Without further purification, this product (0.40 g, 1.0 mM) was combined with benzhydryl isothiocyanate (0.23 g, 1.0 mM) in acetonitrile (30 ml). The mixture was stirred at RT overnight, evaporated in vacuo and chromatographed (EM silica gel 60, 10% EtOAc in CH$_2$Cl$_2$) to give a semi-solid product. Recrystallization from MeOH gave a white solid product. These solids (0.2 g) were dissolved in EtOH (15 ml) and treated with 2 equivalents of anhydrous hydrazine. The mixture was stirred at room temperature overnight and evaporated to dryness. The solid residue was diluted with methylene chloride and filtered to remove the phthalhydazide by-product. The supernatant was evaporated in vacuo and flash column chromatographed (EM silica gel 60; 10% MeOH in CH$_2$Cl$_2$) to give the product. The HCl salt was prepared by the addition of a 1M HCl in Et$_2$O solution to a mixture of the free base in methanol. The resulting white solid precipitates were collected and dried to give the product. m/z (MH$^+$) 523.

EXAMPLE 64

1-[(N1-Piperidinocarbothioyldiphenylmethylamino)-4-yl]-3-(4-aminobutyl)-1,3-dihydro-benzimidazol-2-one (Compound 64)

Compound 9, as prepared in Example 9, was treated as described in Example 63 substituting N-(2-bromoethyl) phthalimide with N-(4-bromobutyl) phthalimide to give the product. m/z (MH$^+$) 551

EXAMPLE 65

1-[(N1-Piperidinocarbothioyl-4-chlorodiphenylmethyl-amino)-4-yl]-3-(4-aminobutyl)-1,3-dihydro-benzimidazol-2-one (Compound 65)

Di(2-pyridyl)thionocarbonate (0.46 g, 1.96 mM) was added to a cold (0° C.) solution of 4-chlorobenzhydrylamine hydrochloride (0.5 g, 1.96 mM) and triethylamine (0.2 ml, 1.96 mM) in methylene chloride (20 ml). The mixture was slowly warmed up to room temperature then stirred at room temperature overnight to form 4-chlorobenzhydryl isothiocyanate. Compound 9, prepared in Example 9, was treated as described in Example 64 substituting the benzhydrylthioisocyanate with the 4-chlorobenzhydryl isothiocyanate prepared above to give the product. m/z (MH$^+$) 585

EXAMPLE 66

1-[(N1-Piperidinocarbothioyl-1,1-di(p-anisyl)methyl-amino)-4-yl]-1,3-dihydrobenzimidazol-2-one (Compound 66)

4-(2-Keto-1-benzimidazolinyl)piperidine was treated as described in Example 13 substituting 2,2-diphenylethylamine with 1,1-di(p-anisyl)methylamine to give the product. m/z (MH$^+$) 503.

EXAMPLE 67

5,6-Dichloro-1-[(N1-piperidinocarbothioylbenzhydrylamino)-4-yl]-3-(3-aminopropyl)-1,3-dihydrobenzimidazol-2-one (Compound 67)

A mixture of 1,2-dichloro-4-fluoro-5-nitrobenzene (5.5 g, 26.2 mM), 4-amino-1-benzylpiperidine (4.98 g, 26.2 mM) and K$_2$CO$_3$ (7.23 g, 5.24 mM) in DMF (40 ml) was stirred in an 80° C. oil bath for 6 hours, cooled to RT overnight and H$_2$O (180 ml) was added. The aqueous mixture was extracted with EtOAc (2×200 ml). The combined EtOAc extracts were washed with brine, dried over MgSO$_4$, and evaporated in vacuo to give a dark oil. The oil was dissolved in EtOAc and 10% Pd/C (5 mole %) was added. The resulting mixture was hydrogenated in a Parr apparatus at 50 psi of H$_2$ pressure over a 24 hour period. The mixture was filtered through Celite and the filtrated evaporated in vacuo to give a crude diamine product. Triphosgene (4.2 g, 14 mM) was added to a mixture of the diamine (5 g, 14 mM) and triethylamine (2 ml, 14 mM) dissolved in methylene chloride. The mixture was stirred at RT for 16 hours and the solid precipitates collected by filtration and dried to give the dichloro substituted benzimidazolone product. This dichloro substituted benzimidazolone (5.5 g, 15.7 mM), N-(3-Bromopropyl)phthalimide (3.9 g, 15.7 mM) and cesium carbonate (9.85 g, 30 mM) in DMF (50 ml) were stirred in an 80–85° C. oil bath for 48 hours, cooled to RT and evaporated in vacuo to remove the DMF. The residue was diluted with H$_2$O (100 ml) and extract with EtOAc (2×100 ml). The combined EtOAc extracts were dried over MgSO$_4$, and evaporated in vacuo to give a crude mixture containing the product. Recrystallization from Et$_2$O gave an off-white solid product. m/z (MH$^+$) 562.

The off-white solids (0.32 g, 0.57 mM) were dissolved in methylene chloride (20 ml), cooled in an ice-bath to 0° C., and 1-chloroethyl chloroformate (0.08 ml, 0.74 mM) was slowly added. The mixture was stirred at 0° C. for one hour, evaporated in vacuo and methanol (30 ml) was added Following 2 hours of refluxing, the mixture was cooled, was evaporated in vacuo, diluted with methylene chloride and stirred at RT for 1 hour. The solid precipitates were collected and dried to provide the de-benzylated intermediate as the HCl salt m/z (MH$^+$) 472. Benzhydryl isothiocyanate (0.60 g, 0.26 mM) was then added to a mixture of the de-benzylated intermediate (0.134 g, 0.26 mM) and triethylamine (0.04 ml, 0.26 mM) in methylene chloride (20 ml). The resulting mixture was stirred at RT overnight, diluted with water (15 ml) and layers were separated. The aqueous layer was again extracted with methylene chloride (20 ml). The combined methylene chloride extracts were dried over MgSO$_4$, evaporated in vacuo, dissolved in EtOH (15 ml) then treated with 2 equivalents of anhydrous hydrazine. The mixture was stirred at room temperature overnight and evaporated to dryness. The solid residue was diluted with methylene chloride and filtered to remove the phthalhydazide by-product. The supernatant was evaporated in vacuo and flash column chromatographed (EM silica gel 60; 10% MeOH in CH$_2$Cl$_2$) to give the product. m/z (MH$^+$) 568

EXAMPLE 68

1-[(N1-Piperidinocarbothioyl-1,1-di(p-anisyl)methylamino)-4-yl]-3-(3-aminopropyl)-1,3-dihydrobenzimidazol-2-one Hydrochloride (Compound 68)

Di(2-pyridyl)thionocarbonate (0.286 g, 1.2 mM) was added to a cold (0° C.) solution of 1,1-di(p-anisyl)methyl amine (0.3 g, 1.2 mM) and triethylamine (0.17 ml) in methylene chloride (10 ml). The resulting mixture was slowly warmed up to RT over a 4 hour period then stirred at RT for additional 1 hour to provide the 1,1-di(p-anisyl)

methyl isothiocyanate. The prepared isothiocyanate was added to Compound 53 (0.94 g, 0.43 mM), prepared in Example 53, dissolved in methylene chloride (10 ml). The mixture was stirred at RT overnight, diluted with water (20 ml) and the layers were separated. The aqueous layer was again extracted with methylene chloride (2×20 ml). The combined $CH_2Cl_2$ extracts were dried over $MgSO_4$, evaporated in vacuo and chromatoraphed (EM silica gel 60, 10% EtOAc in $CH_2Cl_2$) to give the pthalimide intermediate. This intermediate, substituted for Compound 54, was treated as described in Example 55 to give the HCl salt of the product. m/z ($MH^+$) 560

EXAMPLE 69

1-[(N1-piperidinocarbothioyldiphenylmethylamino)-4-yl]-3-(2-amidoethyl)-1,3-dihydro-benzimidazol-2-one (Compound 69)

Ammonium hydrogencarbonate (0.014 g, 0.178 mM) was added to a mixture of Compound 61 (0.046 g, 0.089 mM), prepared in Example 61, di-tert-butyl dicarbonate (0.020 g, 0.089 mM), and pyridine (0.1 ml) dissolved in dioxane (4 ml). The mixture was stirred at RT overnight and water (50 ml) was added. The mixture was stirred at RT for an additional 4 hours and the solid precipitates collected and dried to give a white solid product. m/z ($MH^+$) 514.

EXAMPLE 70

1-[N-(Tert-butoxycarbonyl)piperidin-4yl]-3-(3-chloropropyl)-1,3-dihydrobenzimidazol-2-one (Compound 70)

A mixture of Compound 9 (1.7 g, 5.3 mM), as prepared in Example 9, bromopropylchloride (5.3 ml, 5.3 mM) and cesium carbonate (3.5 g, 10.6 mM) in acetone (60 ml) was stirred at reflux for 24 hours then cooled to RT. The acetone was removed under reduced pressure, the residue diluted with water (60 ml) and the aqueous mixture was extracted with ethyl acetate (2×60 ml). The combined ethyl acetate layers were dried over $MgSO_4$ and evaporated in vacuo to give the product (2.1 g, 100%) as an oil that solidified on standing. m/z ($MH^+$) 393.

EXAMPLE 71

1-[(N1-piperidinocarbothioylbenzhydrylamino)-4-yl]-3-(3-N,N-dimethylaminopropyl)-1,3-dihydrobenzimidazol-2-one (Compound 71)

Compound 70 (0.490 g, 1.25 mM), prepared in Example 70, excess dimethylamine (2 ml, 40% aqueous solution) and THF (20 ml) were combined in a sealed tube and heated in a 68° C. oil bath for 24 hours. The mixture was allowed to cool to room temperature and the THF removed under reduced pressure. Water (30 ml) was added and the resulting aqueous mixture extracted with EtOAc (2×30 ml). The combined EtOAc extracts were dried over $MgSO_4$ and evaporated in vacuo to give a semi-solid. m/z ($MH^+$) 403. The BOC group was removed by treatment of a solution of the semi-solid in methylene chloride (10 ml) with excess trifluoroacetic acid (1 ml). The mixture was stirred at room temperature overnight and evaporated in vacuo. The residue was diluted with EtOAc (80 ml) then washed with saturated $NaHCO_3$ (2×60 ml). The EtOAc extract was dried over $MgSO_4$, evaporated in vacuo and the residual semi-solid (0.332 g, 0.011 mM) dissoloved in methylene chloride (40 ml) was treated with one equivalent of benzhydryl isothiocyanate (0.25 g, 0.011 mM). The resulting mixture was stirred at RT overnight, evaporated in vacuo and diluted with EtOAc. The precipitates were collected and dried to give the white solid product. m/z ($MH^+$) 528.

EXAMPLE 72

1-(Piperidino-4-yl)-3-(3-N-pyrrolidinopropyl)-1,3-dihydrobenzimidazol-2-one (Compound 72)

A mixture of Compound 70 (2.26 g, 5.7 mM), prepared in Example 70, pyrrolidine (1.0 ml, 10.4 mM), potassium carbonate (1.6 g, 11.5 mM) and a catalytic amount of sodium iodide in DMF (40 ml) was heated in a 70° C. oil bath for 16 hours. The mixture was allowed to cool to RT then diluted with water (200 ml). The aqueous mixture was extracted with EtOAc (2×250 ml). The combined EtOAc extracts were dried over $MgSO_4$ and evaporated in vacuo to give the product as an oil (2.4 g, 100%). This oil was dissolved in methylene chloride (100 ml), cooled in an ice bath to 0° C. and trifluoroacetic acid (10 ml) was slowly added. The mixture was slowly warmed to RT and stirred for 6 hours. The solvent and excess TFA was removed under reduced pressure and the product triturated with $Et_2O$ to give the white solid product as the trifloroacetic acid (TFA) salt (2.82 g, 89%). m/z ($MH^+$) 327.

EXAMPLE 73

1-[(N1-piperidinocarbothioylbenzhydrylamino)-4-yl]-3-(3-N-pyrrolidinopropyl)-1,3-dihydro-benzimidazol-2-one (Compound 73)

Compound 72, prepared in Example 72, was diluted with EtOAc (50 ml) and washed with saturated $NaHCO_3$ (50 ml). The aqueous layer was again extracted with EtOAc (60 ml). The combined EtOAc extracts were dried over $MgSO_4$ and evaporated in vacuo to give the free base of Compound 72. A mixture of this free base (0.132 g, 0.40 mM) and benzhydryl isothiocyanate (0.091 g, 0.40 mM) in methylene chloride (20 ml) were stirred at RT overnight. The methylene chloride was removed under reduced pressure and the residue diluted with EtOAc. The precipitates were collected and dried to give the white solid product. m/z ($MH^+$) 554.

EXAMPLE 74

1-[(N1-Piperidinocarbonylbenzylamino-4-yl]-1,3-dihydrobenzimidazol-2-one (Compound 74)

A mixture of 4-(2-keto-1-benzimidazolinyl)piperidine (0.11 g, 0.51 mM) and benzyl isocyanate (0.068 g, 0.53 mM) in methylene chloride (10 ml) were stirred at RT overnight and filtered to give the white solid product. m/z ($MH^+$) 351.

EXAMPLE 75

1-[(N1-Piperidinocarbonyldiphenylmethylamino-4-yl]-1,3-dihydrobenzimidazol-2-one (Compound 75)

4-(2-Keto-1-benzimidazolinyl)piperidine was treated as described in Example 74 substituting benzyl isocyanate with benzhydryl isocyanate to give the white solid product. m/z ($MH^+$) 427

EXAMPLE 76

1-[(N1-Piperidinocarbothioyldiphenylmethylamino)-4-yl]-3-(3-acetamidopropyl)-1,3-dihydrobenzimidazol-2-one (Compound 76)

One drop of sulfuric acid was added to a mixture of the free base of Compound 55 (0.286 g, 0.57 mM), as prepared in Example 55, dissolved in acetic anhydride (20 ml). The mixture was stirred at room temperature for 4 hours and poured into ice water (80 ml). The resulting aqueous mixture was extracted the EtOAc (2×80 ml). The combined EtOAc extracts were washed with 0.5N NaOH solution (80 ml), dried over $MgSO_4$ and evaporated in vacuo to give a crude semi-solid. Purification by column chromatography produced an off-white solid product. m/z ($MH^+$) 542.

EXAMPLE 77
1-[(N1-Piperidinocarbonyldiphenylmethylamino)-4-yl]-3-(3-aminopropyl)-1,3-dihydrobenzimidazol-2-one (Compound 77)

Compound 9, as prepared in Example 9, was treated as described in Example 63 substituting N-(2-bromoethyl) phthalimide with N-(3-bromopropyl) phthalimide and benzhydryl isothiocyanate with benzhydryl isocyanate to give the white solid product (0.18 g, 65%). m/z (MH$^+$) 484.

EXAMPLE 78
1-[(N1-piperidinocarbothioylbiphenylmethylamino)-4-yl]-3-(3-N-(N-Methylpiperazino)propyl)-1,3-dihydrobenzimidazol-2-one (Compound 78)

A mixture of Compound 70 (0.150 g, 0.38 mM), as prepared in Example 70, N-methylpiperazine (0.05 ml, 0.45 mM), potassium carbonate (0.08 g, 0.57 mM) and a catalytic amount of sodium iodide in DMF (10 ml) was heated in a 70° C. oil bath for 16 hours. The mixture was allowed to cool to RT then diluted with water (30 ml). The aqueous mixture was extracted with EtOAc (2×40 ml). The combined EtOAc extracts were dried over MgSO$_4$ and evaporated in vacuo to give an oil (167 mg, 95%). This oil was dissolved in methylene chloride (20 ml), cooled in an ice bath to 0° C. and trifluoroacetic acid (2 ml) was slowly added. The mixture was slowly warmed to RT and stirred for 6 hours. The solvent and excess TFA was removed under reduced pressure and the product triturated with Et$_2$O to give the white solid as the TFA salt. This white solid (0.150 g, 0.26 mM) was combined with triethylamine (0.09 ml, 0.64 mM) and benzhydryl isothiocyanate (0.058 g, 0.26 mM) in CH$_2$Cl$_2$ and stirred at room temperature for 16 hours. The reaction mixture was diluted with water and layers were separated. The aqueous layer was again extracted with CH$_2$Cl$_2$. The combined CH$_2$Cl$_2$ layers were dried over MgSO4, evaporated in vacuo and filtered through a short silica gel column (EM Silica gel 60; 5% MeOH in CH$_2$Cl$_2$) to give the product as a solid. (86 mg, 57%). m/z (MH$^+$) 583.

EXAMPLE 79
1-[(N1-piperidinocarbothioylbiphenylmethylamino)-4-yl]-3-(3-N,N-dipropylaminopropyl)-1,3-dihydrobenzimidazol-2-one (Compound 79)

Compound 70, prepared in Example 70, was treated as described in Example 78 substituting the N-methylpiperazine with dipropylamine to give the product as a solid. m/z (MH$^+$) 584

EXAMPLE 80
1-[(N1-piperidinocarbonylbiphenylmethylamino)-4-yl]-3-(3-N,N-dipropylaminopropyl)-1,3-dihydrobenzimidazol-2-one (Compound 80)

Compound 70, prepared in Example 70, was treated as described in Example 79 substituting the substituting the benzhydryl isothiocyanate with benzhydryl isocyanate to give the product as a solid. m/z (MH$^+$) 568.

EXAMPLE 81
1-[(N1-piperidinocarbothioylbiphenylmethylamino)-4-yl]-3-(3-N-piperidinylpropyl)-1,3-dihydrobenzimidazol-2-one (Compound 81)

Compound 70, as prepared in Example 70, was treated as described in Example 78 substituting the N-methylpiperazine with piperdine to give the product as a solid. m/z (MH$^+$) 568

EXAMPLE 82
1-[(N1-piperidinocarbothioylbiphenylmethylamino)-4-yl]-3-(3,4-dimethylpiperidine-1-yl-propyl)-1,3-dihydrobenzimidazol-2-one (Compound 82)

Compound 70, as prepared in Example 70, was treated as described in Example 78 substituting the N-methylpiperazine with 3,5-methylpiperidine to give the product as a solid. m/z (MH$^+$) 596

EXAMPLE 83
1-[(N1-piperidinocarbothioylbiphenylmethylamino)-4-yl]-3-[3-(4-ethylcarboxypiperidine)propyl]-1,3-dihydrobenzimidazol-2-one (Compound 83)

Compound 70, as prepared in Example 70, was treated as described in Example 78 substituting the N-methylpiperazine with 4-ethylcarboxypiperidine to give the product as a solid. m/z (MH$^+$) 640

EXAMPLE 84
1-[(N1-piperidinocarbothioylbiphenylmethylamino)-4-yl]-3-(3-morpholinopropyl)-1,3-dihydrobenzimidazol-2-one (Compound 84)

Compound 70, as prepared in Example 70, was treated as described in Example 78 substituting the N-methylpiperazine with morpholine to give the product as a solid. m/z (MH$^+$) 570.

EXAMPLE 85
1-[(N1-piperidinocarbothioylbiphenylmethylamino)-4-yl]-3-(3-N,N-diethylaminopropyl)-1,3-dihydrobenzimidazol-2-one (Compound 85)

Compound 70, as prepared in Example 70, was treated as described in Example 78 substituting the N-methylpiperazine with diethylamine to give the product as a solid. m/z (MH$^+$) 556

EXAMPLE 86
1-[(N1-Piperidinocarbothioyl-(2-phenyl-1-L-carboxymethyl)amino-4-yl)-4-yl]-3-(3-pyrrolidinylpropyl)-1,3-dihydrobenzimidazol-2-one (Compound 86)

A mixture of Compound 72 (0.26 g, 0.47 mM), as prepared in example 72, triethylamine (0.2 ml, 1.4 mM) and methyl L-2-isothiocyanato-3-phenyl propionate (0.104 g, 0.47 mM) in methylene chloride (30 ml) were stirred at RT overnight, diluted with water (30 ml) and layers were separated. The aqueous layer was again extracted with CH$_2$Cl$_2$ (1×30 ml). The combined CH$_2$Cl$_2$ layers were dried over MgSO$_4$, evaporated in vacuo then filtered through a short silica gel column (EM Silica gel 60; 5% MeOH in CH$_2$Cl$_2$) to give the product as a solid. m/z (MH$^+$) 550

EXAMPLE 87
1-[(N1-Piperidinocarbothioyl-(2-methoxyphenyl)amino)-4-yl]-3-(3-pyrrolidinylpropyl)-1,3-dihydrobenzimidazol-2-one (Compound 87)

Compound 72, as prepared in Example 72, was treated as described in Example 86 substituting methyl L-2-isothiocyanato-3-phenyl propionate with 2-methoxyphenyl isothiocyanate to give a solid product. m/z (MH$^+$) 494

EXAMPLE 88
1-[(N1-piperidinocarbothioylbiphenylmethylamino)-4-yl]-3-(3-cyclohexylmethylaminopropyl)-1,3-dihydrobenzimidazol-2-one (Compound 88)

To a mixture of the free base of Compound 55 (0.050 g, 0.1 mM), prepared in Example 55, and cyclohexanecarboxaldehyde (0.012 g, 0.1 mM) in methanol (10 ml) was added acetic acid (3 drops). The resultant mixture was stirred at RT for 3 hours and sodium cyanoborohydride (0.006 g, 0.1 mM) was added. The mixture was stirred at RT for two hours, cooled in an ice bath and a 6N NaOH solution was added to a basic pH. Water (50 ml) was added and the resulting mixture extracted with ethyl acetate (2×60 ml). The combined EtOAc extracts were dried over MgSO4, evaporated in vacuo and purified by chromatography (EM silica gel 60; 5% MeOH in $CH_2Cl_2$) to give the product as a white solid. m/z ($MH^+$) 596

EXAMPLE 89

1-[(N1-Piperidinocarbothioyl-(2-fluorobenzyl)amino)-4-yl]-3-(3-pyrrolidinylpropyl)-1,3-dihydrobenzimidazol-2-one (Compound 89)

Compound 72, as prepared in Example 72, was treated as described in Example 86 substituting methyl L-2-isothiocyanato-3-phenyl propionate with 2-fluorobenzyl isothiocyanate to give the product as a solid. m/z ($MH^+$) 480.

EXAMPLE 90

1-(N1-Piperidinocarbothioyl-(2-phenylbenzylamino)-4-yl)-3-(2-diethyaminoethyl)benzimidazol-2-one (Compound 90)

Compound 9, as prepared in Example 9 was treated as described in Example 35 substituting the benzhydryl isothiocyanate with 2-phenylbenzyl isothiocyanate (prepared by treating 2-phenylbenzylamine with di(2-pyridyl)thionocarbonate following the procedure used to prepare 1,1-di(p-anisyl)methyl isothiocyanate in Example 68) to give the product as a solid. m/z ($MH^+$) 542

EXAMPLE 91

1-(N1-Piperidinocarbonyldiphenylmethylamino-4-yl)-3-(2-N,N-diethyaminoethyl)benzimidazol-2-one (Compound 91)

Compound 9, as prepared in Example 9, was treated as described in Example 35 substituting benzhydryl isothiocyanate with benzhydryl isocyanate to give the product as a solid. m/z ($MH^+$) 526.

EXAMPLE 92

1-[(N1-Piperidinocarbonyl-2-methylphenylamino)-4-yl]-3-(2-N,Ndiethylaminoethyl)-1,3-dihydrobenzimidazol-2-one (Compound 92)

Compound 9, as prepared in Example 9, was treated as described in Example 35 substituting benzhydryl isothiocyanate with 2-methylphenyl isocyanate to give the product as a solid. m/z ($MH^+$) 450

EXAMPLE 93

1-(N1-Piperidinocarbothioyldiphenylmethylamino-4-yl)-3-(3-1N-methylpyrrolidin-2-yl-propyl)-1,3-dihydrobenzimidazol-2-one (Compound 93)

Compound 9, as prepared in Example 9, was treated as described in Example 10 substituting methyl iodide with 2-2-(chloroethyl)-1-methylpyrrolidine hydrochloride (converted to the free base by washing a mixture of the hydrochloride salt in EtOAc with a saturated $NaHCO_3$ solution then drying over $MgSO_4$) to give the product. m/z ($MH^+$) 538.

EXAMPLE 94

1-(N1-Piperidinocarbonyldiphenylmethylamino-4-yl)-3-(3-1N-methylpyrrolidin-2-yl-propyl)-1,3-dihydrobenzimidazol-2-one (Compound 94)

Compound 9, as prepared in Example 9, was treated as described in Example 93 substituting the benzhydryl isothiocyanate with benzhydryl isocyanate to give the product.

EXAMPLE 95

1-[(N1-piperidinocarbonylbiphenylmethylamino)-4-yl]-3-(3-morpholinopropyl)-1,3-dihydrobenzimidazol-2-one (Compound 95)

Compound 70, as prepared in Example 70, was treated as described in Example 84 substituting the benzhydryl isothiocyanate with benzhydryl isocyanate to give the product as a solid. m/z ($MH^+$) 554.

EXAMPLE 96

1-[(N1-piperidinocarbonyldiphenylmethylamino)-4-yl]-3-(3-N-pyrrolidinylpropyl)-1,3-dihydrobenzimidazol-2-one (Compound 96)

Compound 72, prepared in Example 72, was treated as described in Example 86 substituting methyl L-2-isothiocyanato-3-phenyl propionate with benzhydryl isocyanate to give the product as a solid. m/z ($MH^+$) 538.

EXAMPLE 97

1-[(N1-piperidinocarbonylbiphenylmethylamino)-4-yl]-3-(3-N-piperidinylpropyl)-1,3-dihydrobenzimidazol-2-one (Compound 97)

Compound 72, prepared in Example 72, was treated as described in Example 81 substituting the benzhydryl isothiocyanate with benzhydryl isocanate to give the product as a solid. m/z ($MH^+$) 552.

EXAMPLE 98

1-[(N1-piperidinocarbothioylbiphenylmethylamino)-4-yl]-3-(3-N,N-methylcyclohexylaminopropyl)-1,3-dihydrobenzimidazol-2-one (Compound 98)

Compound 70, prepared in Example 70, was treated as described in Example 78 substituting the N-methyl piperazine with N-methyl cyclohexylamine to give the solid as a product. m/z ($MH^+$) 596.

EXAMPLE 99

1-[(N1-piperidinocarbonylbiphenylmethylamino)-4-yl]-3-(4-methylpiperidin-1-yl-propyl)-1,3-dihydrobenzimidazol-2-one (Compound 99)

Compound 70, prepared as described in Example 70, was treated as described in Example 113 substituting the benzhydryl isothiocyanate with benzhydryl isocyanate to give the title compound. m/z ($MH^+$) 566.

EXAMPLE 100

1-[(N1-piperidinocarbonylbiphenylmethylamino)-4-yl]-3-(3-N-(N-Methylpiperazino)propyl)-1,3-dihydrobenzimidazol-2-one (Compound 100)

Compound 70, prepared as described in Example 70, was treated as described in Example 78 substituting the benzhydryl isothiocyanate with benzhydryl isocyanate to give the title compound. m/z ($MH^+$) 567.

EXAMPLE 101

1-[(N1-piperidinocarbothioylbiphenylmethylamino)-4-yl]-3-(3,4-dimethypiperidin-1-yl-propyl)-1,3-dihydrobenzimidazol-2-one (Compound 101)

Compound 70, prepared as described in Example 70, was treated as described in Example 82 substituting the benzhydryl isothiocyanate with benzhydryl isocyanate to give the title compound. m/z ($MH^+$) 580.

EXAMPLE 102

1-[(N1-piperidinocarbothioylbiphenylmethylamino)-4-yl]-3-(N-dihydropyrrolidinylpropyl)-1,3-dihydrobenzimidazol-2-one (Compound 102)

Compound 70, as prepared in Example 70, was treated as described in Example 78 substituting the N-methylpipera-

EXAMPLE 103

1-[N-(Tert-butoxycarbonyl)piperidin-4yl]-3-(3-chloropropyl)-1,3-dihydro-benzimidazol-2-one (Compound 103)

The title compound was prepared as described in Example 70 substituting the 3-bromopropylchloride with 4-bromobutylchloride. m/z (MH$^+$) 407.

EXAMPLE 104

1-[(N1-piperidinocarbothioylbiphenylmethylamino)-4-yl]-3-(3-N-pyrrolidinylbutyl)-1,3-dihydrobenzimidazol-2-one (Compound 104)

A mixture of Compound 103 (0.280 g, 0.69 mM), as prepared in Example 103, pyrrolidine (0.08 ml, 0.96 mM), potassium carbonate (0.190 g, 1.4 mM) and a catalytic amount of sodium iodide in DMF (10 ml) was heated in a 70° C. oil bath for 16 hours. The mixture was allowed to cool to RT then diluted with water (200 ml). The aqueous mixture was extracted with EtOAc (2×250 ml). The combined EtOAc extracts were dried over MgSO$_4$ and evaporated in vacuo to give an oil. This oil was dissolved in methylene chloride (20 ml), cooled in an ice bath to 0° C. and trifluoroacetic acid (2 ml) was slowly added. The mixture was stirred at 0° C. for 3½ hours. The solvent and excess TFA was removed under reduced pressure and the product triturated with Et$_2$O to give a semi-solid intermediate as the TFA salt (0.35 g, 89%). This intermediate (0.350 g, 0.61 mM) was combined with triethylamine (0.2 ml, 1.5 mM) and benzhydryl isothiocyanate (0.138 g, 0.61 mM) in CH$_2$Cl$_2$ (40 ml) and stirred at room temperature for 16 hours. The reaction mixture was diluted with water (40 ml) and layers were separated. The aqueous layer was again extracted with CH$_2$Cl$_2$ (40 ml). The combined CH$_2$Cl$_2$ layers were dried over MgSO$_4$, evaporated in vacuo and the crude semi-solid purified by chromatography (EM Silica gel 60; 5% MeOH in CH$_2$Cl$_2$) to give the product (86 mg, 57%). m/z (MH$^+$) 568.

EXAMPLE 105

1-[(N1-piperidinocarbothioylbenzylamino)-4-yl]-3-(3-N-piperidinylpropyl)-1,3-dihydrobenzimidazol-2-one (Compound 105)

Compound 72, as prepared in Example 72, was treated as described in Example 81 substituting benzhydryl isothiocyanate with benzyl isothiocyanate to give the product as a solid. m/z (MH$^+$) 492.

EXAMPLE 106

1-[(N1-piperidinocarbonybenzylamino)-4-yl]-3-(3-N-piperidinylpropyl)-1,3-dihydrobenzimidazol-2-one (Compound 106)

Compound 72, as prepared in Example 72, was treated as described in Example 81 substituting benzhydryl isothiocyanate with benzyl isocyanate to give the product as a solid. m/z (MH$^+$) 476

EXAMPLE 107

1-[(N1-piperidinocarbothioylbiphenylmethylamino)-4-yl]-3-(3-N-pyrrolidinylbutyl)-1,3-dihydrobenzimidazol-2-one (Compound 107)

Compound 103, as prepared in Example 103, was treated as described in Example 104 substituting pyrrolidine with piperidine to give the product as a solid. m/z (MH$^+$) 582.

EXAMPLE 108

1-[(N1-piperidinocarbothioylbiphenylmethylamino)-4-yl]-3-(3-hydroxypropyl)-1,3-dihydrobenzimidazol-2-one (Compound 108)

Compound 9, as prepared in Example 9, was treated as described in Example 53 substituting the N-(3-bromopropy)phthalimide with 2-(3-bromopropoxy)tetrahydro-2H-pyran. The resulting TFA salt was further treated as described in Example 54 to give the product. m/z (MH$^+$) 501.

EXAMPLE 109

1-[(N1-piperidinocarbothioyl-2-methylphenylamino)-4-yl]-3-(3-N-piperidinylpropyl)-1,3-dihydrobenzimidazol-2-one (Compound 109)

Compound 72, as prepared in Example 72, was treated as described in Example 81 substituting benzhydryl isothiocyanate with 2-methylphenyl isothiocyanate to give the product as a solid. m/z (MH$^+$) 492.

EXAMPLE 110

1-[(N1-piperidinocarbonyl-2-methylphenylamino)-4-yl]-3-(3-N-piperidinylpropyl)-1,3-dihydrobenzimidazol-2-one (Compound 110)

Compound 72, as prepared in Example 72, was treated as described in Example 81 substituting benzhydryl isothiocyanate with 2-methylphenyl isocyanate to give the product as a solid. m/z (MH$^+$) 476

EXAMPLE 111

1-[(N1-piperidinocarbothioyl-2-methoxybenzylamino)-4-yl]-3-(3-N-piperidinylpropyl)-1,3-dihydrobenzimidazol-2-one (Compound 111)

Compound 72, as prepared in Example 72, was treated as described in Example 81 substituting benzhydryl isothiocyanate with 2-methoxybenzyl isothiocyanate to give the product as a solid. m/z (MH$^+$) 522.

EXAMPLE 112

1-[(N1-piperidinocarbothioyl-1-naphthalmethylamino)-4-yl]-3-(3-N-piperidinylpropyl)-1,3-dihydrobenzimidazol-2-one (Compound 112)

Compound 72, as prepared in Example 72, was treated as described in Example 81 substituting benzhydryl isothiocyanate with 1-Naphthalenemethyl isothiocyanate to give the product as a solid. m/z (MH$^+$) 542.

EXAMPLE 113

1-[(N1-piperidinocarbothioylbiphenylmethylamino)-4-yl]-3-(4-methylpiperidin-1-yl-propyl)-1,3-dihydrobenzimidazol-2-one (Compound 113)

Compound 70, as prepared in Example 70, was treated as described in Example 78 substituting the N-methylpiperazine with 4-methylpiperidine to give the product as a solid. m/z (MH$^+$) 582.

EXAMPLE 114

1-[(N1-piperidinocarbonyl-2-fluorophenylamino)-4-yl]-3-(3-N-piperidinylpropyl)-1,3-dihydrobenzimidazol-2-one (Compound 114)

Compound 72, as prepared in Example 72, was treated as described in Example 81 substituting benzhydryl isothiocyanate with 2-fluorophenyl isocyanate to give the product as a solid. m/z (MH$^+$) 480.

EXAMPLE 115

1-[(N1-piperidinocarbonthioyl-2-fluorophenylamino)-4-yl]-3-(3-N-piperidinylpropyl)-1,3-dihydrobenzimidazol-2-one (Compound 115)

Compound 72, as prepared in Example 72, was treated as described in Example 81 substituting benzhydryl isothiocyanate with 2-fluorophenyl isothiocyanate to give the product as a solid. m/z (MH$^+$) 496.

EXAMPLE 116

1-[(N1-piperidinocarbonthioyl-R-(−)-alpha-methylbenzylamino)-4-yl]-3-(3-N-piperidinylpropyl)-1,3-dihydrobenzimidazol-2-one (Compound 116)

Compound 72, as prepared in Example 72, was treated as described in Example 81 substituting benzhydryl isothiocyanate with R-(−)-alpha-methylbenzyl isothiocyanate to give the product as a solid. m/z (MH$^+$) 506.

EXAMPLE 117

1-[(N1-piperidinocarbonyl-2-propylphenylamino)-4-yl]-3-(3-N-piperidinylpropyl)-1,3-dihydrobenzimidazol-2-one (Compound 117)

Compound 72, as prepared in Example 72, was treated as described in Example 81 substituting benzhydryl isothiocyanate with 2-propylphenyl isocyanate to give the product as a solid. m/z (MH$^+$) 504.

EXAMPLE 118

1-[(N1-piperidinocarbothioyl-2,2-diphenylethylamino)-4-yl]-3-(3-N-piperidinylpropyl)-1,3-dihydrobenzimidazol-2-one (Compound 118)

Compound 72, as prepared in Example 72, was treated as described in Example 81 substituting benzhydryl isothiocyanate with 2,2-diphenylethyl isothiocyanate to give the product as a solid. m/z (MH$^+$) 582.

EXAMPLE 119

1-[(N1-piperidinocarbothioyl-2-methoxyphenylamino)-4-yl]-3-(3-N-piperidinylpropyl)-1,3-dihydrobenzimidazol-2-one (Compound 119)

Compound 72, as prepared in Example 72, was treated as described in Example 81 substituting benzhydryl isothiocyanate with 2-methoxyphenyl isothiocyanate to give the product as a solid. m/z (MH$^+$) 508.

EXAMPLE 120

1-[(N1-piperidinocarbonyltriphenylmethylamino)-4-yl]-3-(3-N-piperidinylpropyl)-1,3-dihydrobenzimidazol-2-one (Compound 120)

Compound 72, as prepared in Example 72, was treated as described in Example 81 substituting benzhydryl isothiocyanate with trityl isocyanate to give the product as a solid. m/z (MH$^+$) 628.

EXAMPLE 121

1-[(N1-piperidinocarbothioyltriphenylmethylamino)-4-yl]-3-(3-N-piperidinylpropyl)-5-trifluoromethyl-1,3-dihydrobenzimidazol-2-one (Compound 121)

4-Fluoro-3-nitrobenzotrifluoride was substituted for 1,2-dichloro-4-fluoro-5-nitrobenzene and treated as described in Example 67, also substituting the N-(3-bromopropyl) phthalimide for N-(gammachloropropyl)piperidine HCl, to give the product. m/z (MH$^+$) 636.

EXAMPLE 122

1-[(N1-piperidinocarbothioylbiphenylmethylamino)-4-yl]-3-(4-propylpiperidin-1-yl-propyl)-1,3-dihydrobenzimidazol-2-one (Compound 122)

Compound 70, prepared in Example 70, was treated as described in Example 78 substituting the N-methyl piperazine with 4-N-propylpiperidine to give the solid as a product. m/z (MH$^+$) 610.

EXAMPLE 123

1-[(N1-Piperidinocarbothioyl-(2,3-dimethoxybenzyl)amino)-4-yl]-3-(3-pyrrolidinylpropyl)-1,3-dihydrobenzimidazol-2-one (Compound 123)

Compound 72, as prepared in Example 72, was treated as described in Example 86 substituting methyl L-2-isothiocyanato-3-phenyl propionate with 2,3-dimethoxybenzyl isothiocyanate to give a solid product. m/z (MH$^+$) 500.

EXAMPLE 124

1-[(N1-piperidinocarbothioyl-4-chlorobenzylamino)-4-yl]-3-(3-N-piperidinylpropyl)-1,3-dihydrobenzimidazol-2-one (Compound 124)

Compound 72, as prepared in Example 72, was treated as described in Example 81 substituting benzhydryl isothiocyanate with 4-chlorobenzyl isothiocyanate to give the product as a solid. m/z (MH$^+$) 527.

EXAMPLE 125

1-[(N1-piperidinocarbothioylcyclohexylamino)-4-yl]-3-(3-N-piperidinylpropyl)-1,3-dihydrobenzimidazol-2-one (Compound 125)

Compound 72, as prepared in Example 72, was treated as described in Example 81 substituting benzhydryl isothiocyanate with cyclohexyl isothiocyanate to give the product as a solid. m/z (MH$^+$) 484

EXAMPLE 126

1-[(N1-piperidinocarbothioyltriphenylmethylamino)-4-yl]-3-(3-N-piperidinylpropyl)-1,3-dihydrobenzimidazol-2-one (Compound 126)

Compound 72, as prepared in Example 72, was treated as described in Example 81 substituting benzhydryl isothiocyanate with trityl isothiocyanate to give the product as a solid. m/z (MH$^+$).

EXAMPLE 127

1-(N-1-Piperidinocarbothioyl-(2-phenylbenzylamino)-4-yl)-3-(3-N-pyrrolidinopropyl)benzimidazol-2-one (Compound 127)

Compound 72, as prepared in Example 72, was treated as described in Example 81 substituting benzhydryl isothiocyanate with 2-phenylbenzyl isothiocyanate (prepared by treating 2-phenylbenzylamine with di(2-pyridyl) thionocarbonate following the procedure used to prepare 1,1-di(p-anisyl)methyl isothiocyanate in Example 68) to give the product as a solid. m/z (MH$^+$) 568

EXAMPLE 128

1-[(N1-piperidinocarbothioylpropylamino)-4-yl]-3-(3-N-piperidinylpropyl)-1,3-dihydrobenzimidazol-2-one (Compound 128)

Compound 72, as prepared in Example 72, was treated as described in Example 81 substituting benzhydryl isothiocyanate with propyl isothiocyanate to give the product. m/z (MH$^+$) 444

EXAMPLE 129
1-[(N1-piperidinocarbothioyl-1-adamantylamino)-4-yl]-3-(3-N-piperidinylpropyl)-1,3-dihydrobenzimidazol-2-one (Compound 129)

Compound 72, as prepared in Example 72, was treated as described in Example 81 substituting benzhydryl isothiocyanate with 1-adamantyl isothiocyanate to give the product. m/z (MH$^+$) 536

EXAMPLE 130
1-[(N1-piperidinocarbothioyl-butylamino)-4-yl]-3-(3-N-piperidinylpropyl)-1,3-dihydrobenzimidazol-2-one (Compound 130)

Compound 72, as prepared in Example 72, was treated as described in Example 81 substituting benzhydryl isothiocyanate with t-butyl isothiocyanate to give the product. m/z (MH$^+$) 444

EXAMPLE 131
1-[(N1-piperidinocarbothioylfluorenylamino)-4-yl]-3-(3-N-piperidinylpropyl)-1,3-dihydrobenzimidazol-2-one (Compound 131)

Compound 72, as prepared in Example 72, was treated as described in Example 81 substituting benzhydryl isothiocyanate with 9-fluorenyl isothiocyanate (prepared by treating 9-aminofluorene with di(2-pyridyl)thionocarbonate following the procedure used to prepare 1,1-di(p-anisyl)methyl isothiocyanate in Example 68) to give the product as a solid. m/z (MH$^+$) 566

EXAMPLE 132
1-[(N1-piperidinocarbothioyl-2-isopropylphenylamino)-4-yl]-3-(3-N-piperidinylpropyl)-1,3-dihydrobenzimidazol-2-one (Compound 132)

Compound 72, as prepared in Example 72, was treated as described in Example 81 substituting benzhydryl isothiocyanate with 2-isopropylphenyl isothiocyanate to give the product. m/z (MH$^+$) 520

EXAMPLE 133
1-[(N1-piperidinocarbothioylphenpropylamino)-4-yl]-3-(3-N-piperidinylpropyl)-1,3-dihydrobenzimidazol-2-one (Compound 133)

Compound 72, as prepared in Example 72, was treated as described in Example 81 substituting benzhydryl isothiocyanate with phenpropyl isothiocyanate to give the product. m/z (MH$^+$) 520

EXAMPLE 134
1-[(N1-Piperidinocarbothioyldiphenylmethylamino)-4-yl]-3-(3-cyclohexylpropyl)-1,3-dihydro-benzimidazol-2-one (Compound 134)

Compound 9, as prepared in Example 9, was treated as described in Example 10 substituting methyl iodide with cyclohexylpropylbromide to give the product. m/z (MH$^+$) 567

EXAMPLE 135
1-[(N-Piperidin-1-yl)-N-(2-phenylbenzyl)guanidin-4-yl]-3-pyrrolidin-1-yl-1,3-dihydro-benzimidazol-2-one (Compound 135)

A mixture of the TFA salt of Compound 72 (0.266 g, 0.48 mM), as prepared in Example 72, 1,3-bis(tertbutoxycarbonyl)-2-methyl-2-thiopseudourea (0.138 g, 0.48 mM) and excess triethylamine (0.4 ml, 2.8 mM) was gently heated in a 40° C. oil bath and stirred at that temperature for three days. The reaction mixture was cooled to room temperature, diluted with water (40 ml) and extracted with ethyl acetate (2×50 ml). The combined ethyl acetate extracts were dried over MgSO$_4$, evaporated in vacuo and the crude mixture chromatographed (EM silica gel 60, 10% MeOH in CH$_2$Cl$_2$) to give the desired guanidine intermediate (0126 g, 46%). Sodium hydride (0.007 g, 0.25 mM was them added to a cooled (0° C.) mixture of the guanidine intermediate (0.126 g, 0.22 mM) in dry DMF (5 ml). The resulting mixture was slowly warmed up to RT, stirred at RT for 1 hour and 2-phenylbenzyl bromide was slowly added. Stirring was continued for an additional 4 hours and H$_2$O (40 ml) was slowly added. The aqueous mixture was extracted with ethyl acetate (2×50 ml). The combined ethyl acetate extracts were dried over MgSO$_4$ and evaporated in vacuo. The product, isolated by trituration with Et$_2$O, was diluted with methylene chloride (20 ml), cooled to 0° C. and TFA (2 ml) was added. The mixture was warm up to RT then stirred at RT overnight. The mixture was diluted with saturated NaHCO$_3$ (40 ml), another (20 ml) of methylene chloride was added and the layers were separated. The methylene chloride layer was again washed with saturated NaHCO$_3$, dried over MgSO$_4$, evaporated in vacuo and chromatographed (10% MeOH in CH$_2$Cl$_2$) to give the product. (MH$^+$) 537.

EXAMPLE 136
V1a, V1b or V2 Binding Assay

Receptor binding studies were performed using recombinant human V1a, V1b or V2 receptors. Cellular membranes were harvested from HEK-293 cells transfected to express either the V1a, V1b or V2 receptors. Compounds were evaluated for their ability to displace $^3$H-arginine vasopressin ($^3$H-AVP; specific activity 40–87 Ci/mmol; NEN Life Sciences, Boston, Mass.). Compounds were solubilized in dimethylsulfoxide (DMSO) and diluted to working concentration of 10% DMSO with assay buffer (50 mM Tris, 5 mM MgCl$_2$, 0.1% BSA, pH 7.5). Assay buffer was supplemented with several protease inhibitors (1 mM Pefabloc, 5 µg/ml aprotinin/leupeptin/pepstatin A, 50 µg/ml bacitracin; Sigma Chemical, St. Louis, Mo.). Non-specific binding was determined using 1.25 µM arginine vasopressin (AVP; Peninsula Labs, Belmont, Calif.). Assay reagents and test compounds were added to 96-well round bottom polypropylene plates (145 µl buffer, 5 µl compound in 10% DMSO, 25 µl buffer containing 10,000 cpm tracer, 25 µl cell membrane). After incubation for 1 hour at room temperature, the well contents were aspirated across a Unifilter GF/C plate (Packard Instrument, Downers Grove, Ill.) which had been presoaked in 0.3% polyethyleneimine to prevent peptide sticking. The wells were washed repeatedly with cold saline containing 0.05% Tween 20. The plate was then dried and 25 µl Microscint-20 cocktail (Packard Instruments) added to each well. The plates were sealed and counted on a Top-Count scintillation counter (Packard Instruments) using quench correction.

EXAMPLE 137
Neuropeptide Y Receptor Binding Assay

| MATERIALS |
|---|
| Cell Membranes from KAN-TS cells having NPY2 receptors |
| $^{125}$I-PYY (NEN, cat. #NEX240) |
| PYY 3–36 human, (Bachem, cat. #H-8585.0500) |
| Buffers: |

| | |
|---|---|
| Homogenization buffer: | 20 mM Tris-HCl, pH 7.7 |
| | 5 mM EDTA |

-continued

| MATERIALS | |
|---|---|
| Binding buffer: | 20 mM HEPES, pH 7.4 |
| | 120 mM NaCl |
| | 0.22 mM $KH_2PO_4$ |
| | 1.3 mM $CaCl_2$ |
| | 0.8 mM $MgSO_4$ |
| Compound Diluent: | 30% DMSO in 50 mM HEPES |
| Wash buffer: | PBS (GIBCO, cat. #14040-133) |
| Compounds: | 400 μM in 30% DMSO/50 mM HEPES, pH 7.4 |

Method
Load 96-well RIA racks with RIA vials (Sarstedt, cat. #73.1055)
Prepare membranes—use 2×15 cm confluent plates/96-well assay plate
  Add 14 mls Homogenization buffer/cell pellet
  Homogenize at high speed for 15 seconds
  Transfer to 15 ml conical tube and spin 5' at 4° C. at setting 3 in RT6000 centrifuge
  Transfer supernatant to 30 ml Corex tube
  Balance and spin 25' at 15,000 rpm at 4° C.
  Resuspend pellet in 10 mls Binding buffer
  Homogenize at high speed for 15 sec.
  Bring volume up to 50 mls in Binding buffer (25 mls/2× 96-well plates)
  Keep on ice until use or freeze in aliquots (2 plates/tube) in −70° C.
Prepare $^{125}$I-PYY (for 2×96-well compound plates)
  Dilute 50 uCi $^{125}$I-PYY in 1 ml $H_2O$
  Add 0.4 ml 10% BSA to 20 ml Binding buffer
  Add 150 μl $^{125}$I-PYY, mix well
Prepare Controls:
  NSB (1 μM PYY final conc.): 40 μl PYY (100 μM stock)+60 μl 30% DMSO in HEPES=40 μM PYY—add 5 μl/well
  Total Binding: Add 5 μl/well of Compound Diluent
To start reaction:
  Add 5 μl compound (final conc. @10 μM)
  Add 95 μl $^{125}$I-PYY
  Add 100 μl membrane
  Incubate at R.T. for 1 hr.
To stop reaction:
  Spin plates for 10' at setting 9 in RT6000 centrifuge
  Aspirate supernatant from tubes, add 300 μl PBS and aspirate again.
  After plates are washed and aspirated, put individual tubes in 12×75 mm polypropylene carrier tubes. Count on gamma counter.

Table I below sets forth the vasopressin receptor and neuropeptide Y receptor binding data of some compounds of the instant invention.

TABLE I

| | | | Binding IC$_{50}$ (μM) or % Inh @ μM | | | |
|---|---|---|---|---|---|---|
| No. | Structure | M.W. | NPY-2@10 | V1a@1.0 | V1b@1.0 | V2@1.0 |
| 1 | | 442.58 | 52% | 0.59 | 0%@10 | 38% |
| 2 | | 414.96 | 1% | 21% | 0%@10 | 7% |

TABLE I-continued

| No. | Structure | M W. | NPY-2@10 | V1a@1.0 | V1b@1.0 | V2@1.0 |
|---|---|---|---|---|---|---|
| | | | Binding IC$_{50}$ ($\mu$M) or % Inh @ $\mu$M | | | |
| 3 | 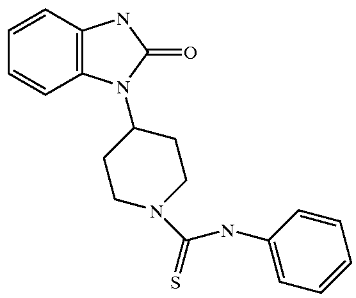 | 352.46 | 13% | 0% | 0%@10 | 7% |
| 4 | 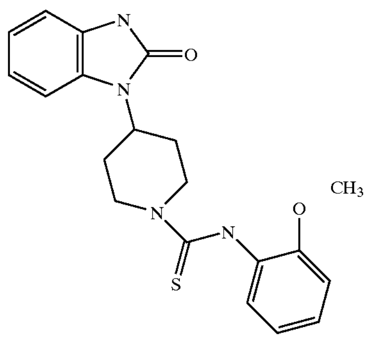 | 382.49 | 6% | 0% | 0%@10 | 0% |
| 5 | 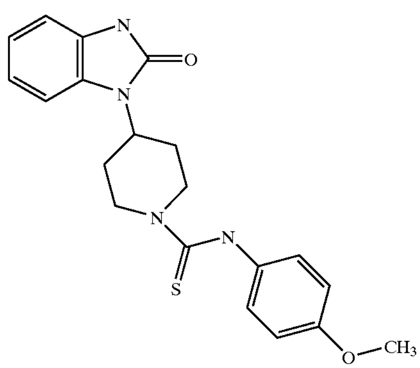 | 382.49 | 14% | 38% | 8%@10 | 34% |
| 6 | 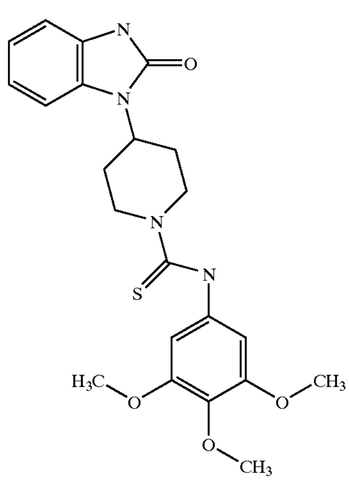 | 442.54 | 16% | 20% | 0%@10 | 9% |

TABLE I-continued

| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 7 | | 414.51 | 13% | 9.2 | 11%@10 | 31% |
| 8 | | 380.47 | 5% | 55% | 13%@10 | 10% |
| 10 | | 456.61 | 34% | 0.38 | — | 51% |

TABLE I-continued

| No. | Structure | M W. | NPY-2@10 | V1a@1.0 | V1b@1.0 | V2@1.0 |
|---|---|---|---|---|---|---|
| | | | Binding IC$_{50}$ ($\mu$M) or % Inh @ $\mu$M | | | |
| 11 | benzimidazol-2-one-piperidine-N-benzyl thiourea | 366.49 | 26% | 3.1 | 0%@10 | 3% |
| 12 | benzimidazol-2-one-piperidine-N-(2-chlorobenzyl) thiourea | 400.93 | 21% | 2.5 | 0%@10 | 5%@10 |
| 13 | benzimidazol-2-one-piperidine-N-(2,2-diphenylethyl) thiourea | 456.61 | 22% | 1.2 | 1%@10 | 4%@10 |
| 14 | benzimidazol-2-one-piperidine-N-(2-methoxybenzyl) thiourea | 396.51 | 18% | 0% | 0%@10 | 1% |

TABLE I-continued
| No. | Structure | M W. | Binding IC₅₀ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 15 | 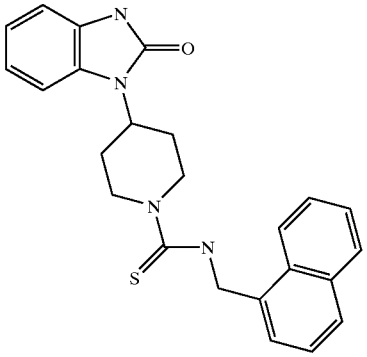 | 416.55 | 14% | 17% | 7%@10 | 10% |
| 16 | 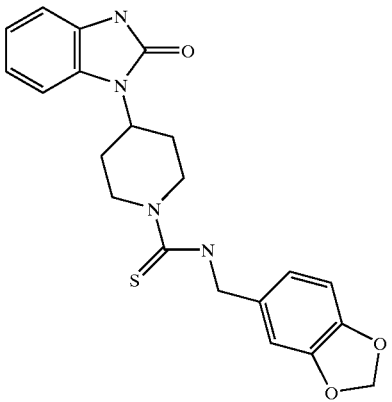 | 410.50 | 15% | 40% | 15%@10 | 0% |
| 17 | 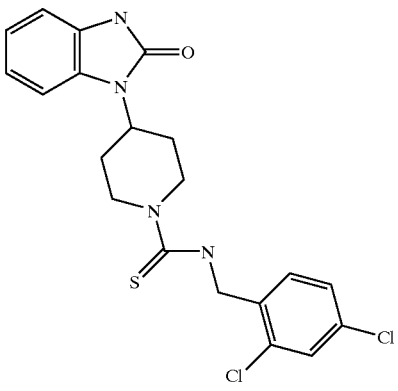 | 435.38 | 15% | 12% | 7%@10 | 14% |

TABLE I-continued
| No. | Structure | M W. | Binding IC$_{50}$ ($\mu$M) or % Inh @ $\mu$M | | | |
| | | | NPY-2@10 | V1a@1.0 | V1b@1.0 | V2@1.0 |
|---|---|---|---|---|---|---|
| 18 | 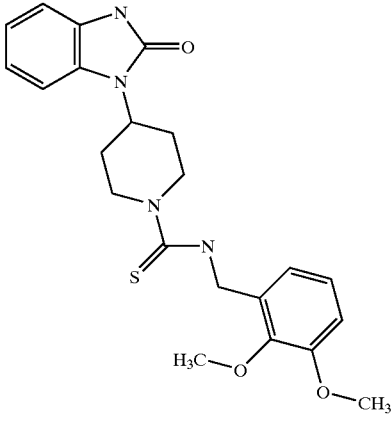 | 426.54 | 10% | 22% | 3%@10 | 9% |
| 19 | 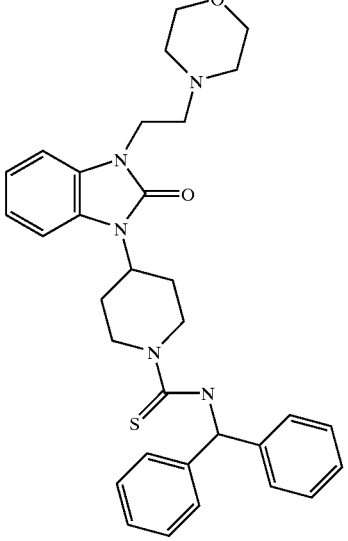 | 555.74 | 69% | 0.27 | — | 42% |
| 20 | 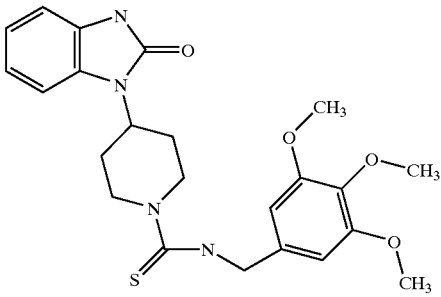 | 456.56 | 12% | 25%@10 | 0%@10 | 0% |

TABLE I-continued

| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 21 | 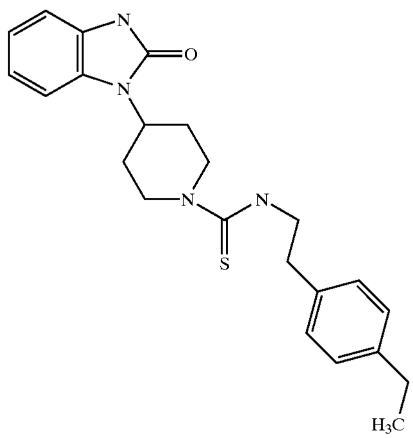 | 408.57 | 13% | 31% | — | 19% |
| 22 | 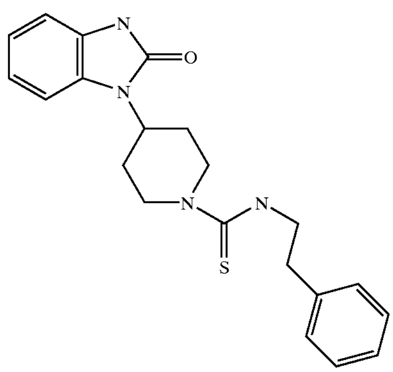 | 380.51 | 11% | 45% | 0%@10 | 4% |
| 23 | 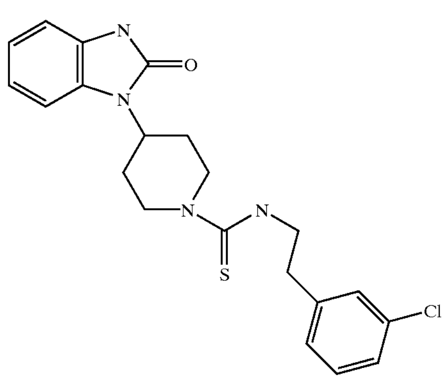 | 414.96 | 15% | 56% | 0%@10 | 12% |

TABLE I-continued

| No. | Structure | M.W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 24 | 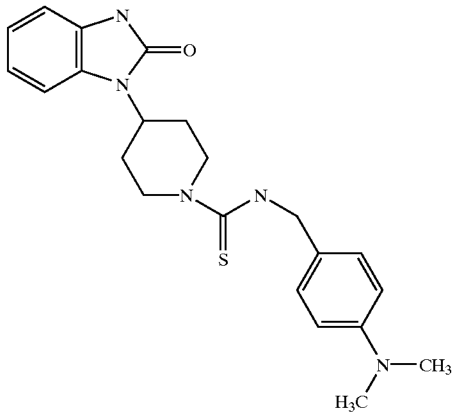 | 409.56 | 12% | 19% | 0%@10 | 9% |
| 25 | 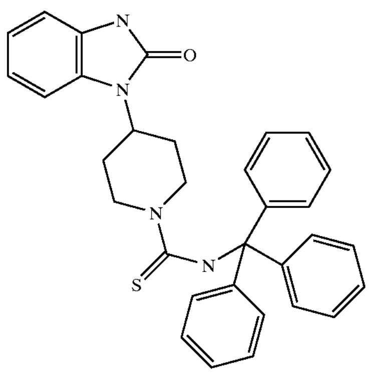 | 518.68 | 13% | 0% | 0%@10 | 0% |
| 26 | 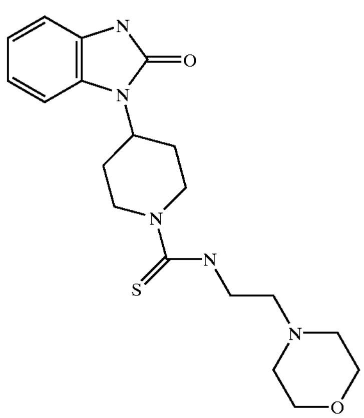 | 389.52 | 10% | 33% | 0%@10 | 20% |
| 27 | 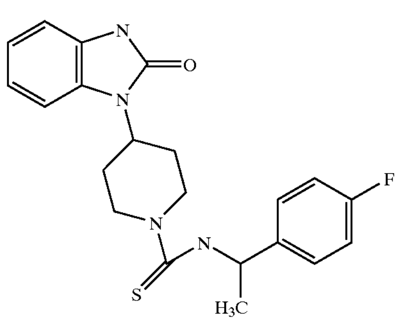 | 398.50 | 15% | 33% | 0%@10 | 20% |

TABLE I-continued

| No. | Structure | M W. | NPY-2@10 | V1a@1.0 | V1b@1.0 | V2@1.0 |
|---|---|---|---|---|---|---|
| | | | Binding IC$_{50}$ ($\mu$M) or % Inh @ $\mu$M | | | |
| 28 | 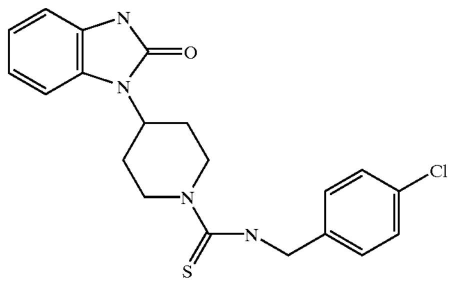 | 400.93 | 24% | 22% | 3%@10 | 0% |
| 29 | 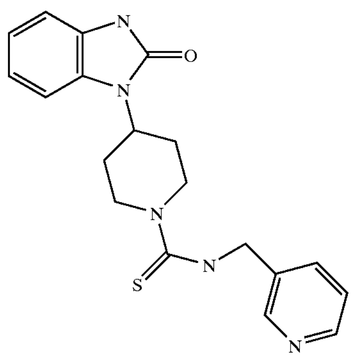 | 367.48 | 11% | 1.9 | 0%@10 | 2% |
| 30 | 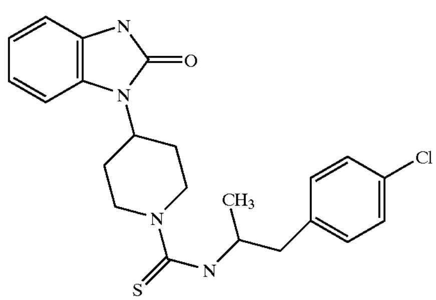 | 428.99 | 23% | 0.39 | 0%@10 | 9% |
| 31 | 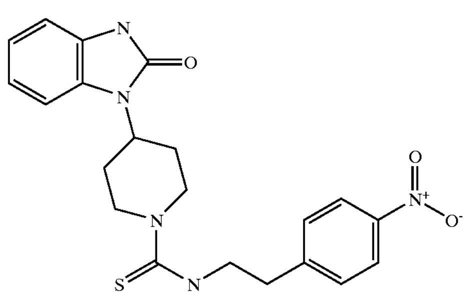 | 425.51 | 17% | 19% | 5%@10 | 15% |

TABLE I-continued

| No. | Structure | M W. | Binding IC$_{50}$ ($\mu$M) or % Inh @ $\mu$M | | | |
|---|---|---|---|---|---|---|
| | | | NPY-2@10 | V1a@1.0 | V1b@1.0 | V2@1.0 |
| 32 | 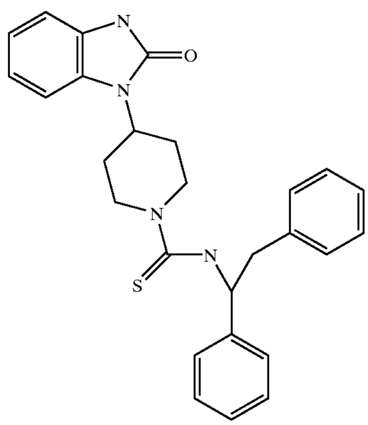 | 456.61 | 26% | 42% | 4%@10 | 9% |
| 33 | 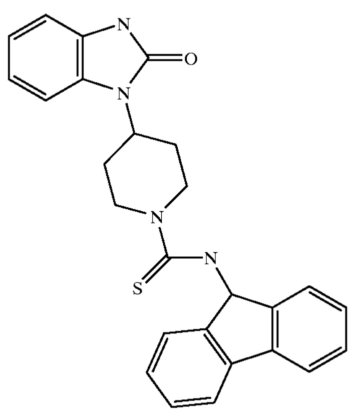 | 440.57 | 13% | 33% | 9%@10 | 0% |
| 34 | 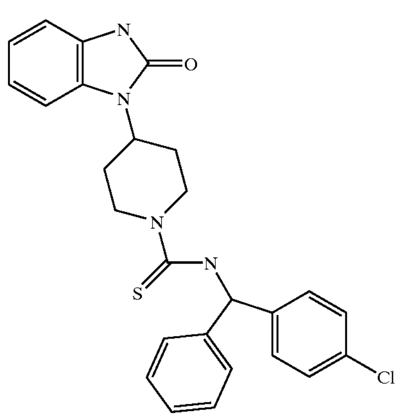 | 477.03 | 22% | 42% | 13%@10 | 21% |

TABLE I-continued
| No. | Structure | M.W. | Binding IC$_{50}$ ($\mu$M) or % Inh @ $\mu$M | | | |
|---|---|---|---|---|---|---|
| | | | NPY-2@10 | V1a@1.0 | V1b@1.0 | V2@1.0 |
| 35 | 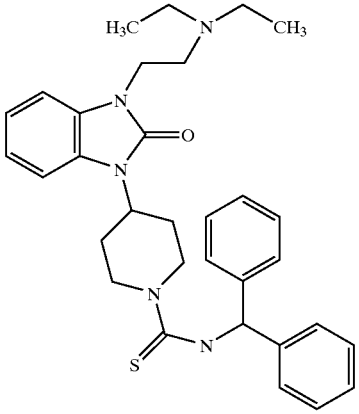 | 541.76 | 74% | 0.075 | 47%@1 | 44% |
| 36 | 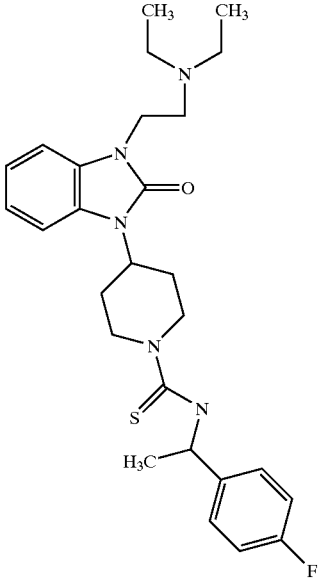 | 497.68 | 16% | 45% | 20%@10 | 0% |
| 37 | 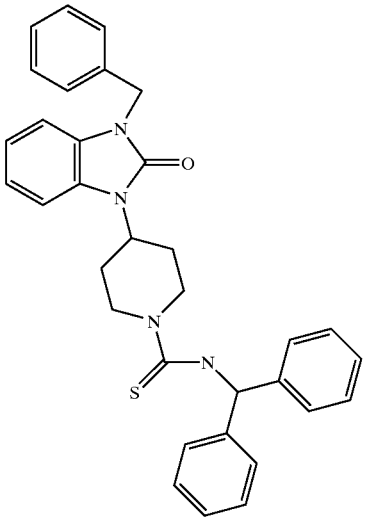 | 532.71 | 0% | 5% | 8%@10 | 2% |

TABLE I-continued

| No. | Structure | M.W. | NPY-2@10 | V1a@1.0 | V1b@1.0 | V2@1.0 |
|-----|-----------|------|----------|---------|---------|--------|
| 38  | 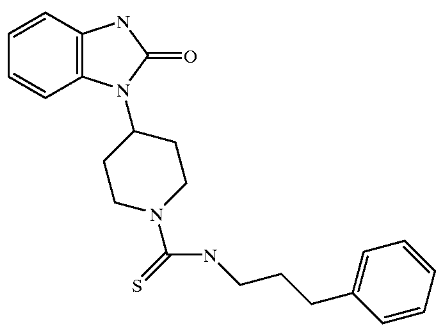          | 394.54 | 7% | 25% | 0%@10 | 9% |
| 39  | 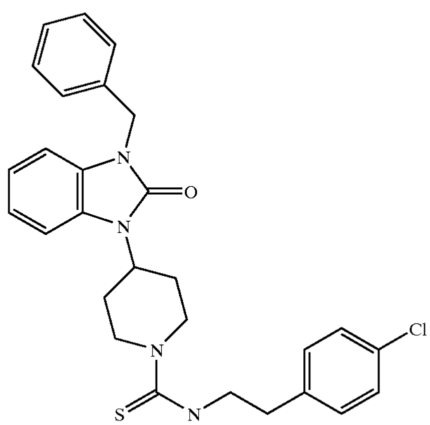          | 505.08 | 18% | 17% | 7%@10 | 0% |
| 40  | 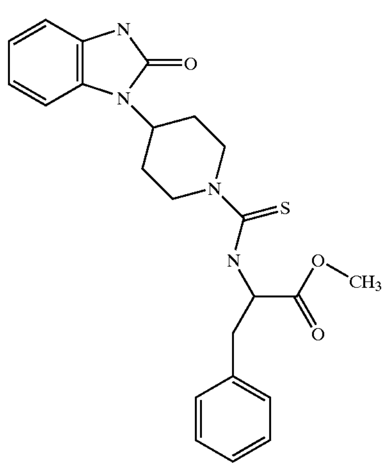          | 438.55 | 17% | 0.19 | 11%@10 | 0% |

Binding IC$_{50}$ ($\mu$M) or % Inh @ $\mu$M

TABLE I-continued

| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 41 | 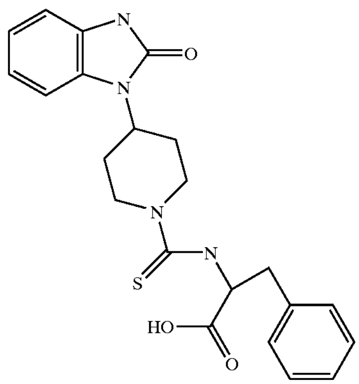 | 424.52 | 11% | 8% | — | 0% |
| 42 | 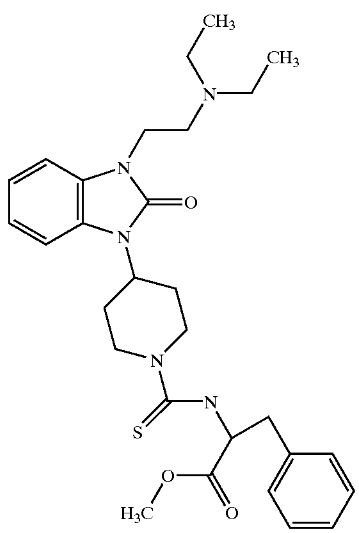 | 537.7266 | 10% | 0.038 | 37%@10 | 0% |
| 43 | 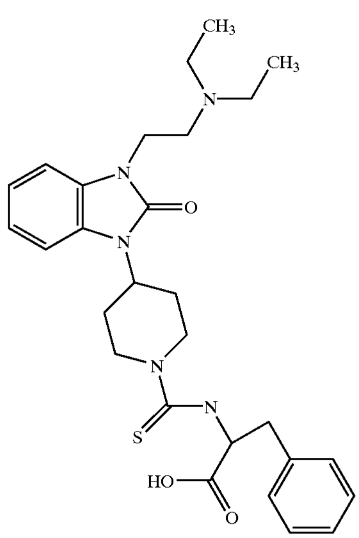 | 523.6997 | 13% | 39% | 16%@10 | 10% |

TABLE I-continued

| | | | Binding IC$_{50}$ ($\mu$M) or % Inh @ $\mu$M | | | |
|---|---|---|---|---|---|---|
| No. | Structure | M.W. | NPY-2@10 | V1a@1.0 | V1b@1.0 | V2@1.0 |
| 44 | | 508.6447 | 9% | 37% | 24%@10 | 2% |
| 45 | | 506.6722 | 15% | 54% | — | 9% |
| 46 | | 566.7247 | 16% | 8%@0.1 | 26%@10 | 0% |

TABLE I-continued

| No. | Structure | M.W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 47 | 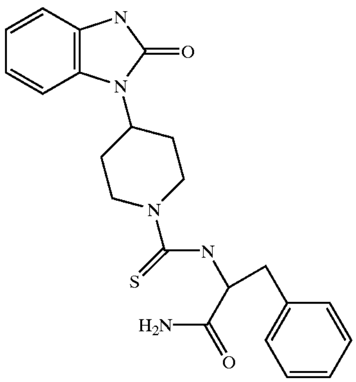 | 423.539 | 10% | 45% | 0%@10 | 14% |
| 48 | 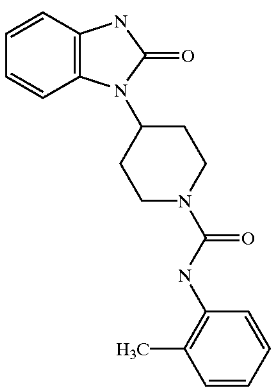 | 350.4204 | 22% | 2% | 3%@10 | 0% |
| 49 | 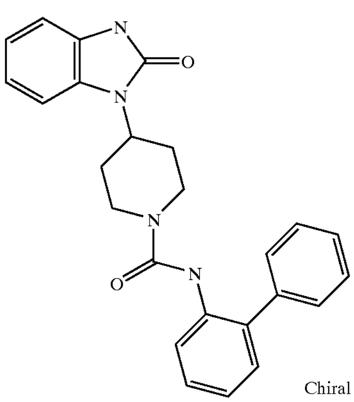 | 412.4913 | 12% | 63% | 18%@10 | 0% |

TABLE I-continued

| No. | Structure | M W. | NPY-2@10 | V1a@1.0 | V1b@1.0 | V2@1.0 |
|-----|-----------|------|----------|---------|---------|--------|
| 50 | 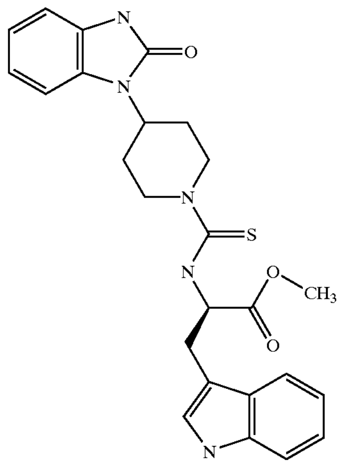 | 477.5873 | 16% | 8% | 15%@10 | 0% |
| 51 | 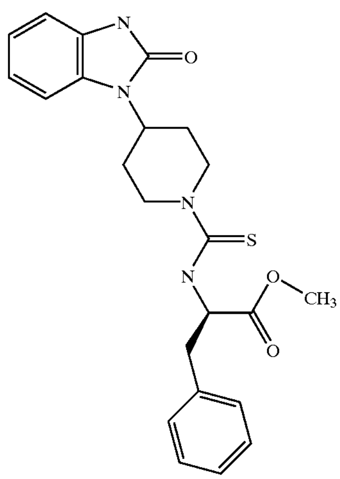 | 438.5506 | 2% | 25% | 19%@10 | 1% |
| 52 | 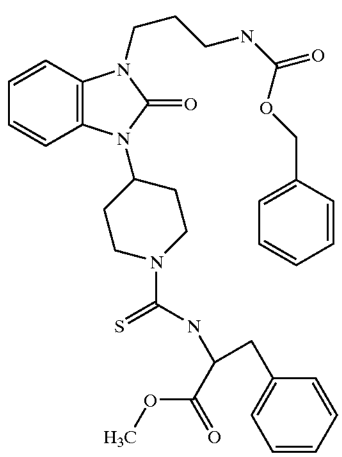 | 629.7803 | 11% | 0.58 | 13%@10 | — |

Binding IC$_{50}$ ($\mu$M) or % Inh @ $\mu$M

TABLE I-continued
| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 54 | 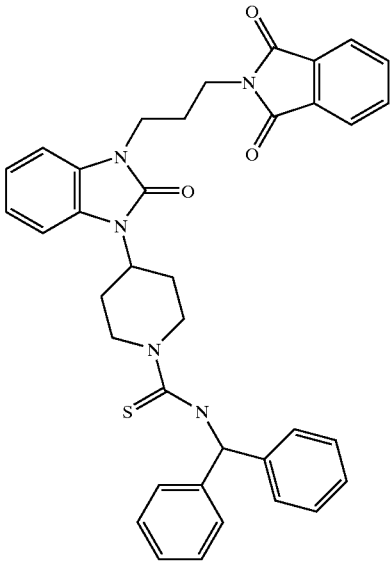 | 629.7828 | 4% | 47% | 18%@10 | 0% |
| 55 | 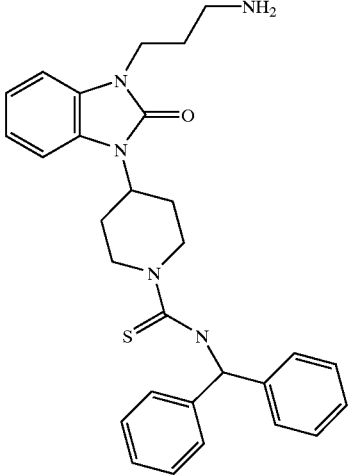 | 536.1405 | 82% | 0.027 | 5.1 | 1.25 |
| 56 | 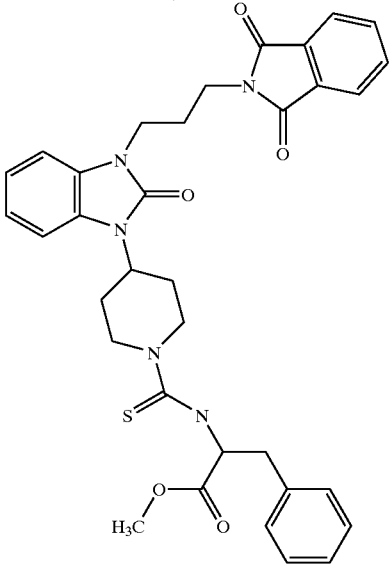 | 625.7486 | 22% | 0.36 | 19%@10 | 3% |

TABLE I-continued

| No. | Structure | M W. | NPY-2@10 | V1a@1.0 | V1b@1.0 | V2@1.0 |
|---|---|---|---|---|---|---|
| | | | Binding IC$_{50}$ ($\mu$M) or % Inh @ $\mu$M | | | |
| 57 | (Chiral structure with benzimidazolone, piperidine, thiourea, phenylalanine methyl ester, propylamine) | 532.1065 | 20% | 0.26 | 25%@10 | 0% |
| 58 | (Chiral structure with benzimidazolone, piperidine, thiourea, phenylalanine methyl ester, guanidinopropyl) | 574.1469 | 2% | 52% | — | — |
| 59 | (Structure with benzimidazolone, piperidine, thiourea, diphenylmethyl, guanidinopropyl) | 541.7205 | 90% | 0.032 | 62%@10 (4.1) | 18% |

TABLE I-continued
| No. | Structure | M.W. | Binding IC$_{50}$ ($\mu$M) or % Inh @ $\mu$M | | | |
|---|---|---|---|---|---|---|
| | | | NPY-2@10 | V1a@1.0 | V1b@1.0 | V2@1.0 |
| 60 | 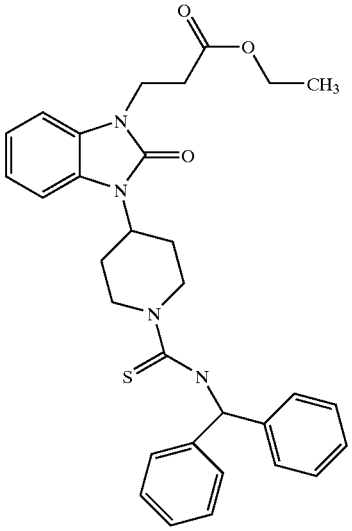 | 542.7021 | 35% | 49% | 19%@10 | 0% |
| 61 | 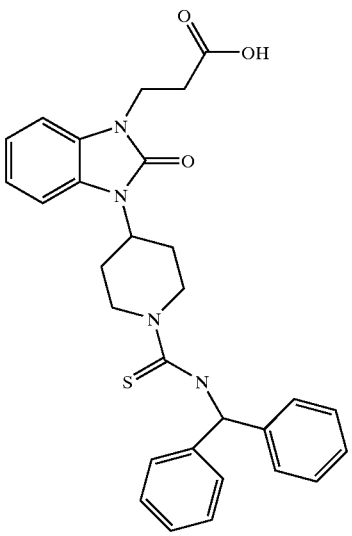 | 514.6484 | 90% | 17% | 22%@10 | 0% |
| 62 | 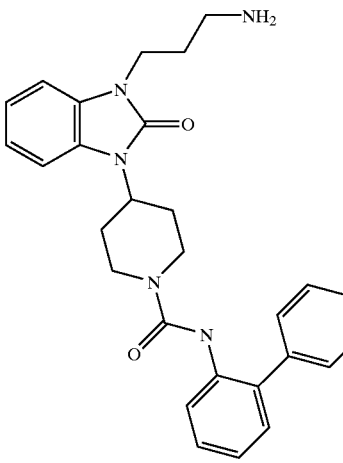 | 506.04 | 50% | 0.2 | 35%@10 | 0% |

TABLE I-continued
| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 63 | 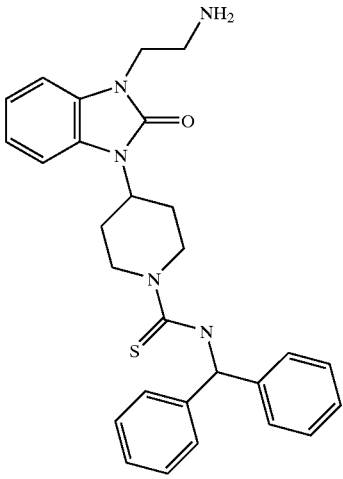 | 522.1138 | 94% | 0.05 | 74%@10 (4.7) | 42% |
| 64 | 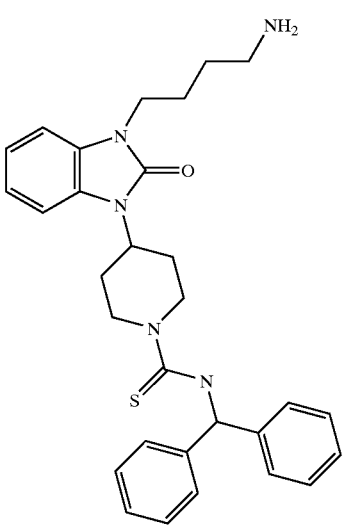 | 550.1676 | 93% | 0.024 | 5.4 | 0.56 |
| 65 | 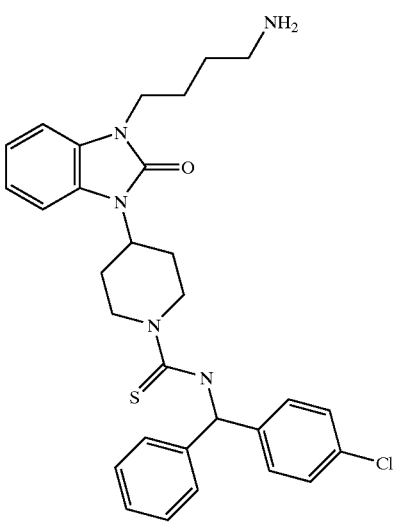 | 584.6124 | 51% | 0.077 | 51%@10 | 0.5 |

TABLE I-continued
| No. | Structure | M W. | NPY-2@10 | V1a@1.0 | V1b@1.0 | V2@1.0 |
|-----|-----------|------|----------|---------|---------|--------|
| 66  | 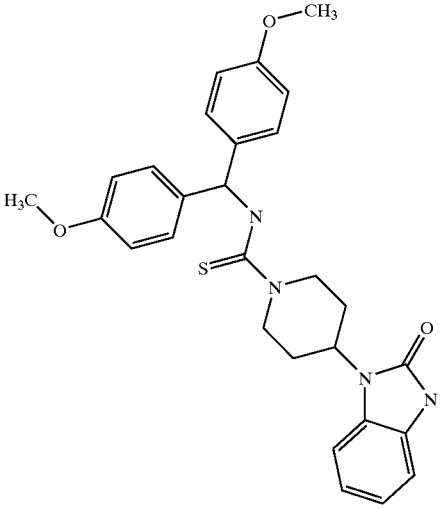 | 502.6374 | 21% | 15%@0.1 | 11%@10 | 0% |
| 67  | 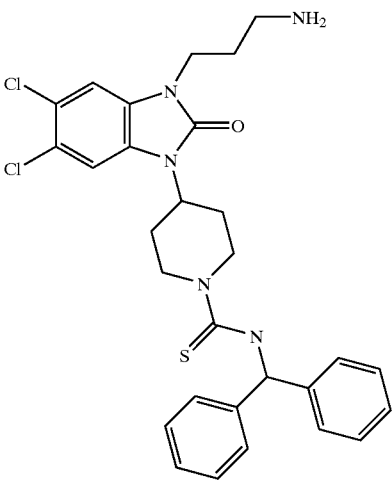 | 568.5696 | 2% | 57%@0.1 | 45%@10 | 0% |
| 68  | 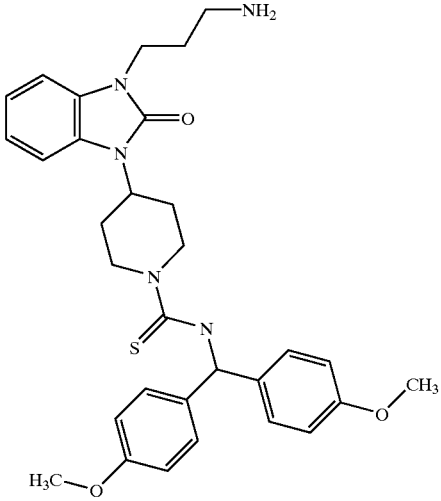 | 559.73 | 11% | 46%@0.1 | 66%@10 (4.6) | 0% |

TABLE I-continued

| No. | Structure | M.W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 69 | 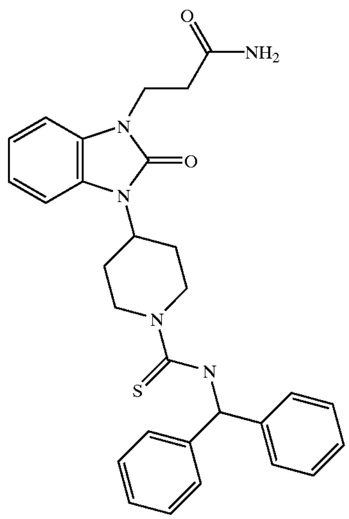 | 513.6636 | 40% | 22% | 27%@10 | 0% |
| 71 | 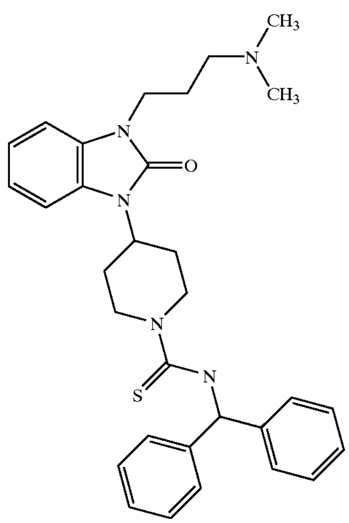 | 527.7339 | 79% | 0.029 | 88%@10 (0.87) | 0% |
| 73 | 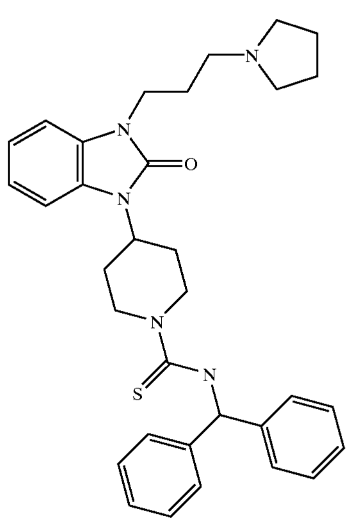 | 553.7718 | 89% | 0.016 | 0.3 | 0% |

TABLE I-continued

| No. | Structure | M W. | NPY-2@10 | V1a@1.0 | V1b@1.0 | V2@1.0 |
|-----|-----------|------|----------|---------|---------|--------|
| | | | Binding IC$_{50}$ ($\mu$M) or % Inh @ $\mu$M | | | |
| 74 | 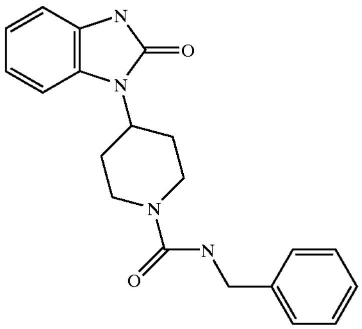 | 350.4204 | 0% | 0% | 29%@10 | 0% |
| 75 | 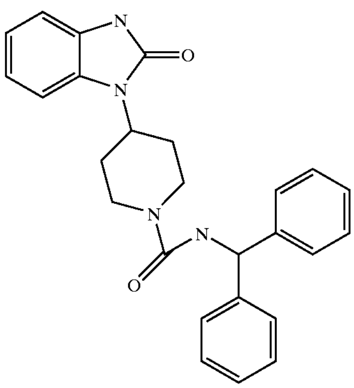 | 426.5182 | 12% | 58% | 1 | 0% |
| 76 | 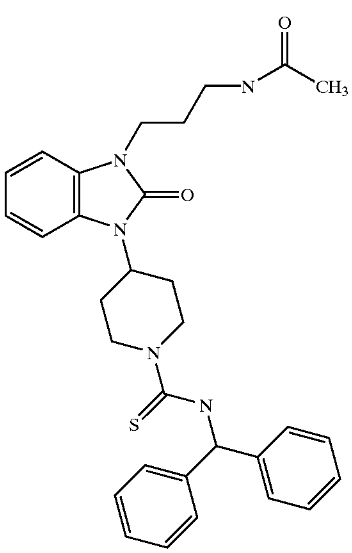 | 541.7174 | 41% | 0.25 | 25%@10 | 0% |

TABLE I-continued
| No. | Structure | M.W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 77 | 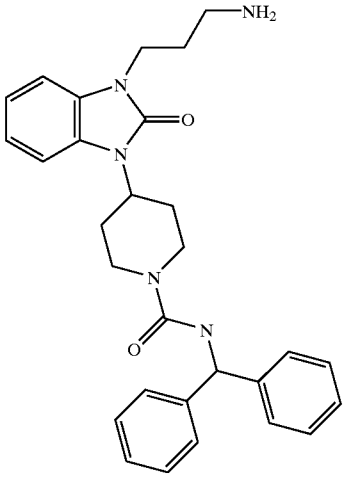 | 483.6135 | 10% | 0.079 | 30%@10 | 0% |
| 78 | 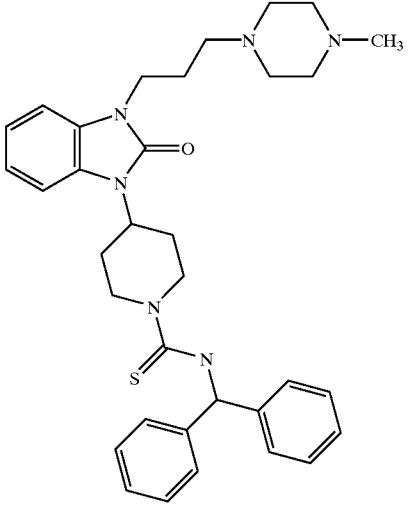 | 582.8133 | 74% | 95% | 41%@10 | 17% |
| 79 | 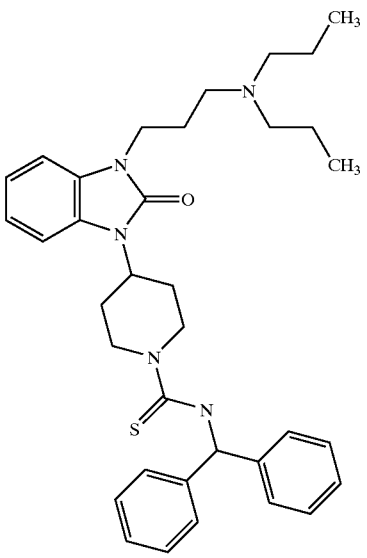 | 583.8414 | 80% | 0.016 | 48% | 13% |

TABLE I-continued
| No. | Structure | M W. | Binding IC$_{50}$ ($\mu$M) or % Inh @ $\mu$M | | | |
| | | | NPY-2@10 | V1a@1.0 | V1b@1.0 | V2@1.0 |
|---|---|---|---|---|---|---|
| 80 | 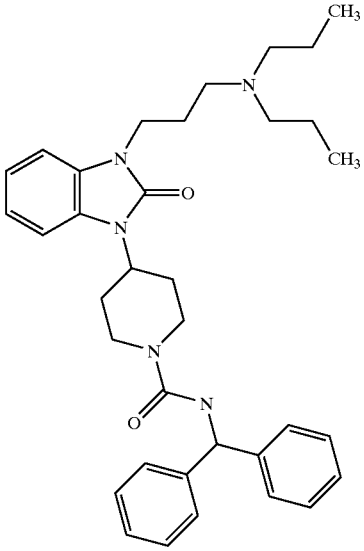 | 567.7748 | — | 0.17 | 38% | 11% |
| 81 | 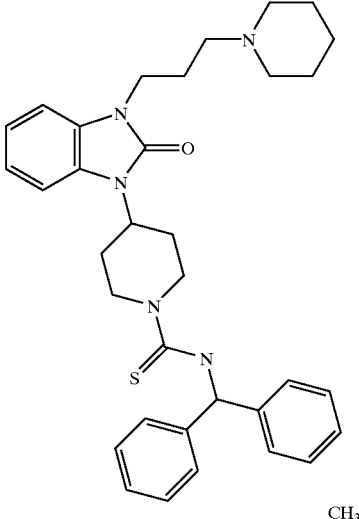 | 567.7986 | 89% | 0.004 | 0.076 | 18% |
| 82 | 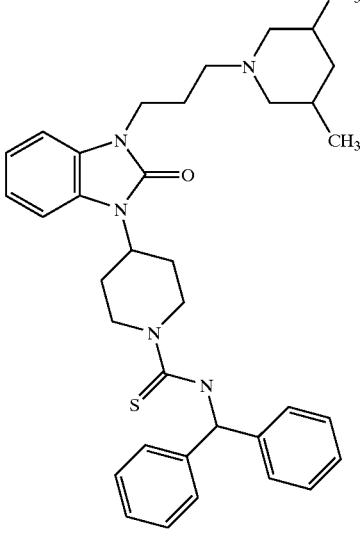 | 595.8524 | 91% | 0.006 | 0.14 | 11% |

TABLE I-continued
| No. | Structure | M W. | NPY-2@10 | V1a@1.0 | V1b@1.0 | V2@1.0 |
|-----|-----------|------|----------|---------|---------|--------|
| | | | Binding IC$_{50}$ ($\mu$M) or % Inh @ $\mu$M | | | |
| 83 | 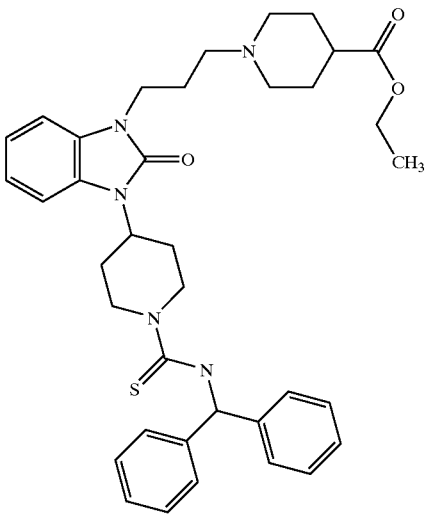 | 639.8622 | 79% | 0.044 | 47% | 2% |
| 84 | 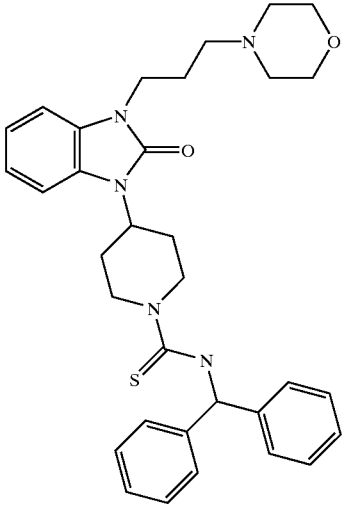 | 569.7712 | 73% | 0.022 | 0.274 | 8% |
| 85 | 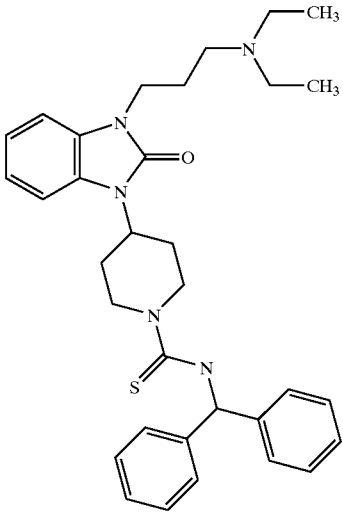 | 555.7877 | 81% | 0.020 | 0.230 | 8% |

TABLE I-continued

| No. | Structure | M.W. | NPY-2@10 | V1a@1.0 | V1b@1.0 | V2@1.0 |
|---|---|---|---|---|---|---|
| | | | Binding IC$_{50}$ ($\mu$M) or % Inh @ $\mu$M | | | |
| 86 | 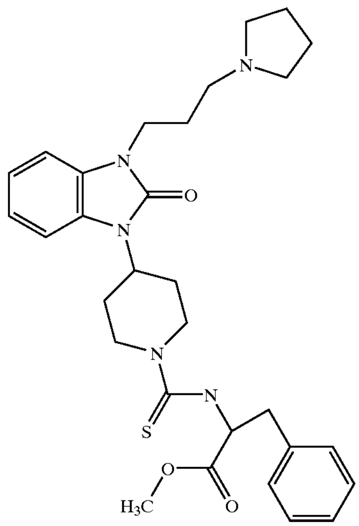 | 549.7375 | 10% | 0.013 | 1.19 | 3% |
| 87 | 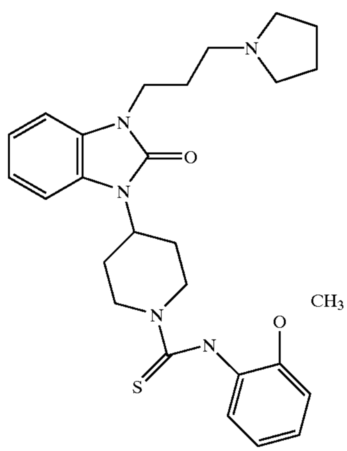 | 493.6734 | 13% | 30% | 23% | 3% |
| 88 | 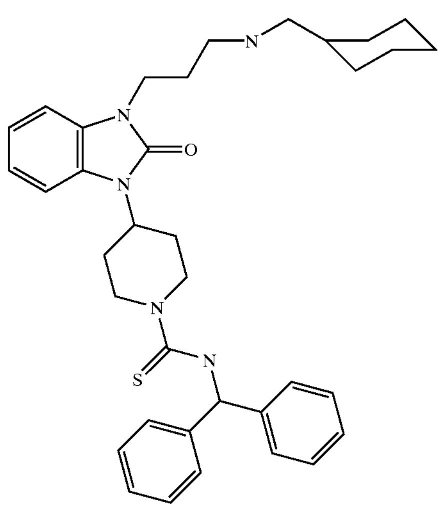 | 595.8524 | — | 0.036 | 1.0 | 3% |

TABLE I-continued
| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 89 | 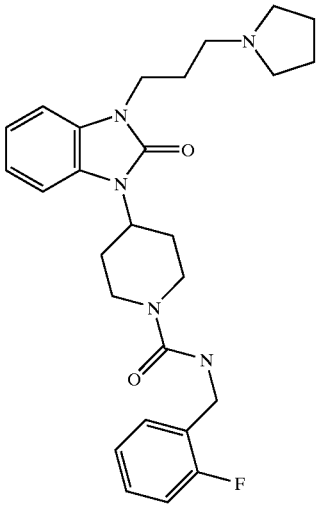 | 479.5979 | 8% | 34% | 10% | 0 |
| 90 | 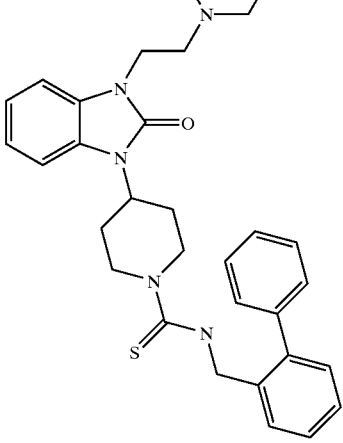 | 541.7607 | 13% | 0.062 | 27% | 5% |
| 91 | 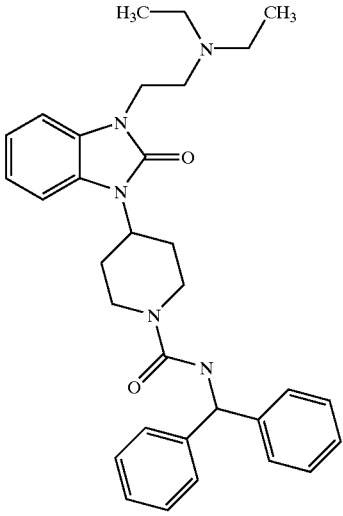 | 525.6942 | 56% | 64% | 24% | 0% |

TABLE I-continued
| No. | Structure | M W. | Binding IC$_{50}$ ($\mu$M) or % Inh @ $\mu$M | | | |
|-----|-----------|------|------|------|------|------|
| | | | NPY-2@10 | V1a@1.0 | V1b@1.0 | V2@1.0 |
| 92 | 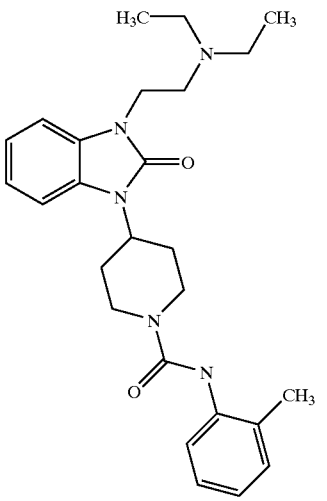 | 449.5964 | 0% | 3% | 5% | 3% |
| 93 | 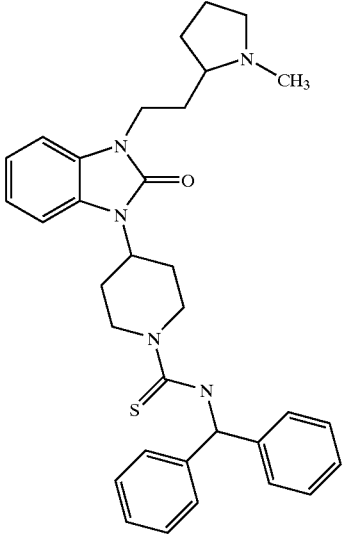 | 553.7718 | 17% | 0.049 | 48% | 0% |
| 94 | 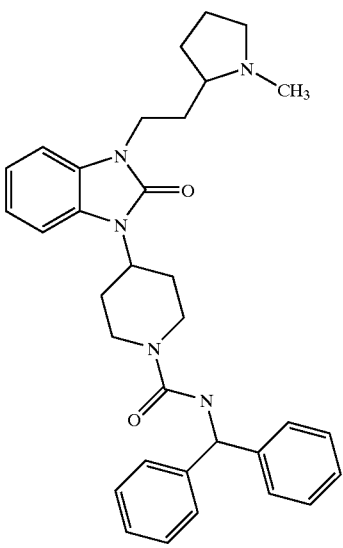 | 537.7051 | 78% | 68% | 33% | 8% |

TABLE I-continued
| No. | Structure | M.W. | Binding IC₅₀ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 95 | 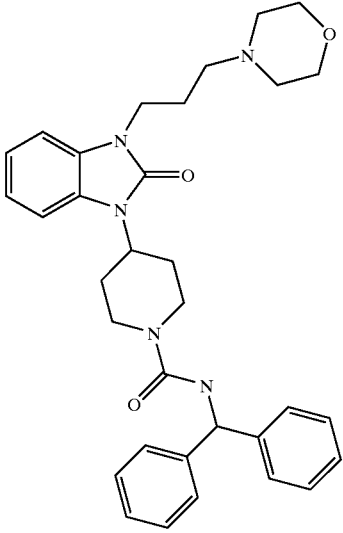 | 553.7046 | 0% | 0.162 | 23% | 2% |
| 96 | 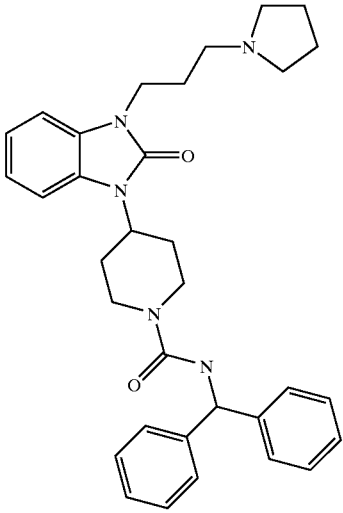 | 537.7051 | 20% | 0.079 | 43% | 0% |
| 97 | 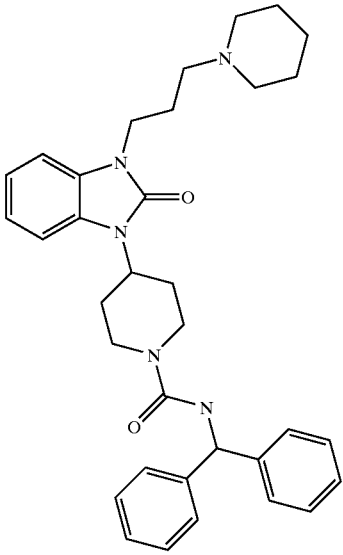 | 551.7321 | 14% | 0.034 | 35% | 0% |

TABLE I-continued
| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 98 | 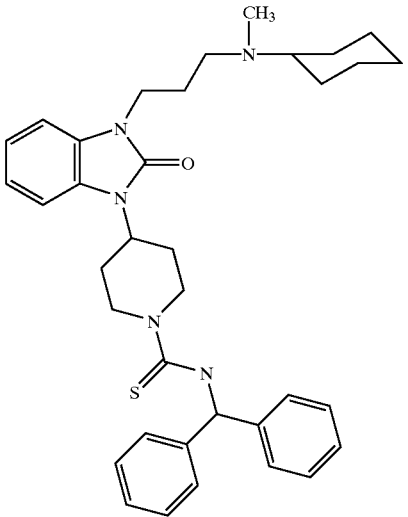 | 595.8524 | 85% | 0.022 | 0.179 | 0% |
| 99 | 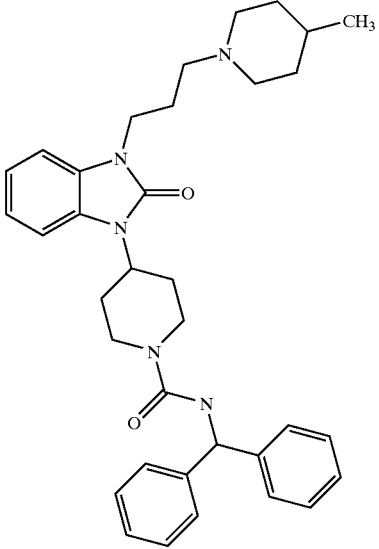 | 565.7589 | 29% | 0.126 | 46% | 16% |
| 100 | 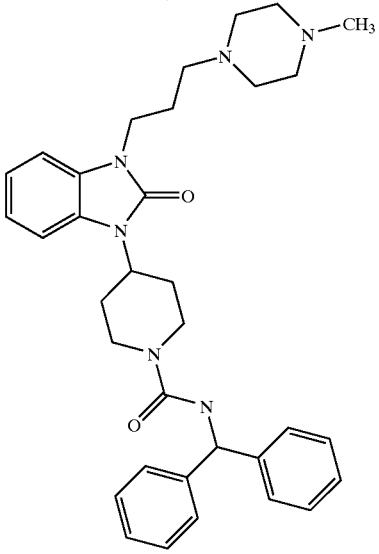 | 566.7467 | 6% | 0.283 | 36% | 24% |

TABLE I-continued

| No. | Structure | M.W. | Binding IC₅₀ (μM) or % Inh @ μM | | | |
|---|---|---|---|---|---|---|
| | | | NPY-2@10 | V1a@1.0 | V1b@1.0 | V2@1.0 |
| 101 | 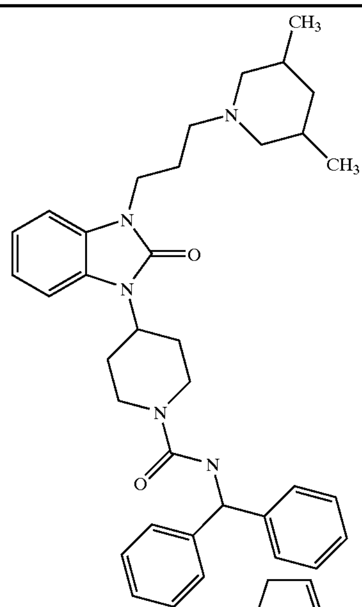 | 579.7858 | 21% | 0.014 | 43% | 0% |
| 102 | 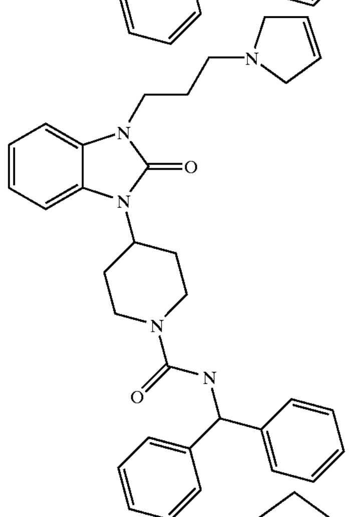 | 535.6893 | 23% | 0.123 | 41% | 6% |
| 104 | 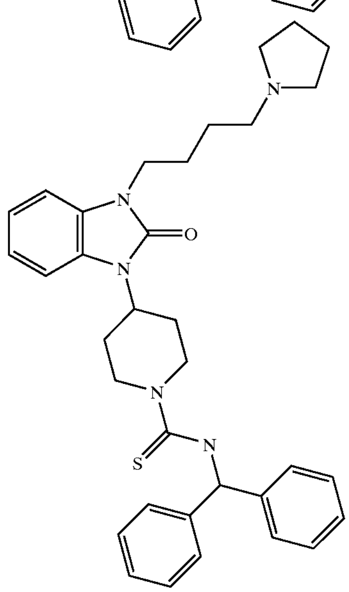 | 567.7986 | 96% | 0.018 | 48% | 14% |

TABLE I-continued

| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 105 | 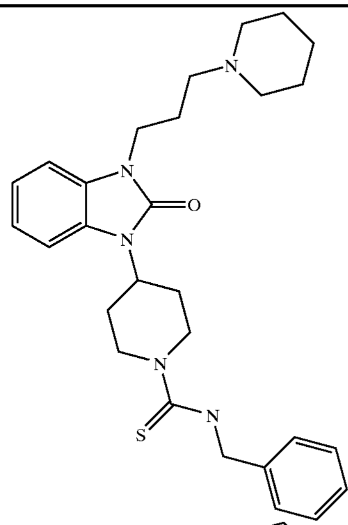 | 491.7009 | 12% | 0.188 (58%) | 30% | 0% |
| 106 | 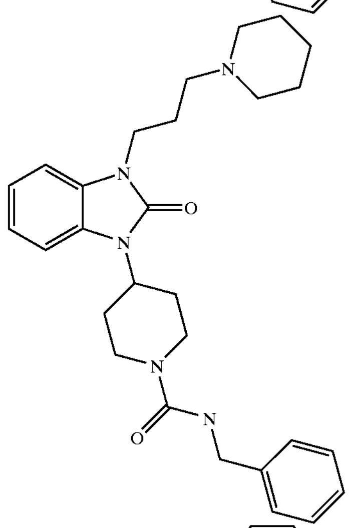 | 475.6343 | 0% | 56% | 32% | 2% |
| 07 | 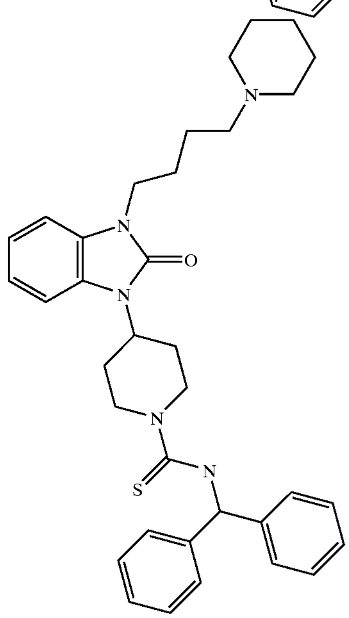 | 581.8255 | 95% | 0.022 | 45% | 12% |

TABLE I-continued
| No. | Structure | M.W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 108 | 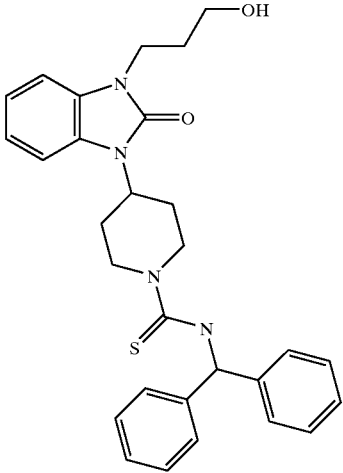 | 500.6648 | 41% | 0.579 | 37% | 16% |
| 109 | 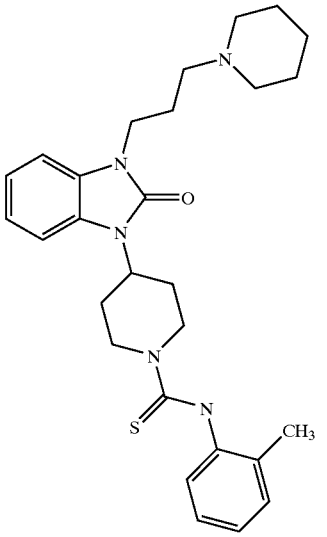 | 491.7009 | 58% | 0.056 | 14% | 0% |
| 110 | 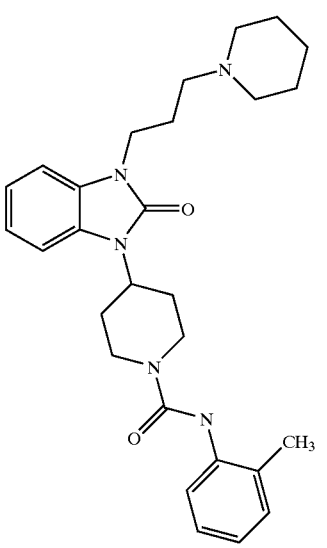 | 475.6343 | 0% | 41% | 19% | 2% |

TABLE I-continued

| | | | Binding IC$_{50}$ ($\mu$M) or % Inh @ $\mu$M | | | |
|---|---|---|---|---|---|---|
| No. | Structure | M.W. | NPY-2@10 | V1a@1.0 | V1b@1.0 | V2@1.0 |
| 111 | | 521.7272 | 31% | 0.109, 0.056 | 30% | 0% |
| 112 | | 541.7607 | 55% | 0.139 | 32% | 0% |

TABLE I-continued

| No. | Structure | M W. | Binding IC$_{50}$ ($\mu$M) or % Inh @ $\mu$M | | | |
|---|---|---|---|---|---|---|
| | | | NPY-2@10 | V1a@1.0 | V1b@1.0 | V2@1.0 |
| 113 | 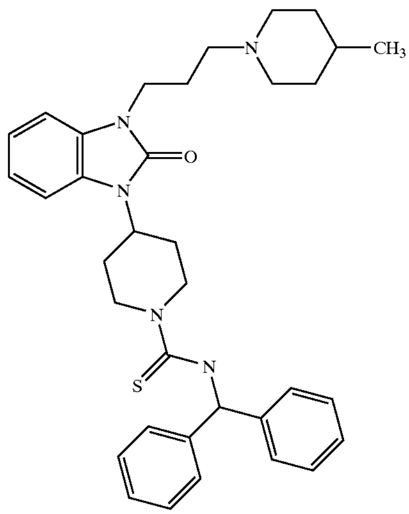 | 581.825 | 89% | 0.023 (70%) | 47% | 7% |
| 114 | 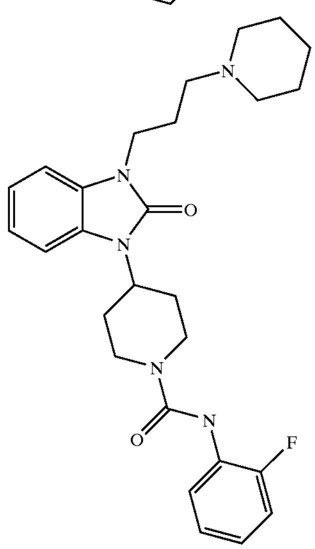 | 479.597 | 17% | 1% | 4% | 2% |
| 115 | 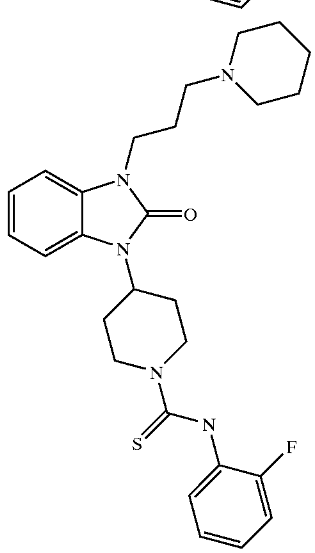 | 495.664 | 26% | 13% | 20% | 11% |

TABLE I-continued
| No. | Structure | M W. | NPY-2@10 | V1a@1.0 | V1b@1.0 | V2@1.0 |
|---|---|---|---|---|---|---|
| | | | Binding IC$_{50}$ ($\mu$M) or % Inh @ $\mu$M | | | |
| 116 | 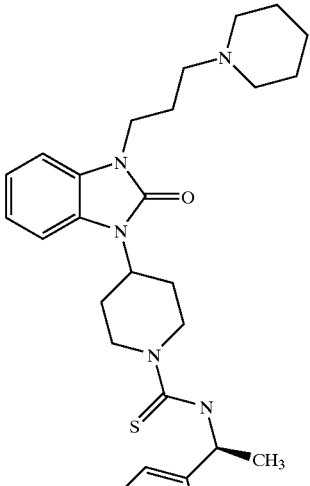 | 505.727 | 25% | 85% | 47% | 18% |
| 117 | 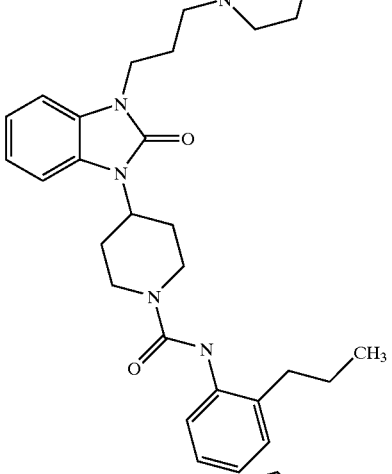 | 503.687 | 1% | 0.331 (68%) | 43% | 15% |
| 118 | 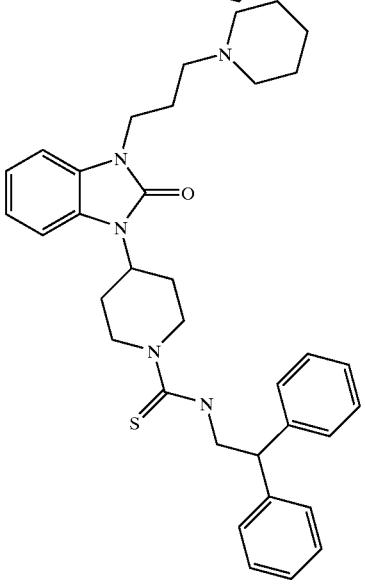 | 581.825 | 52% | 94% | 55% | 21% |

TABLE I-continued
| No. | Structure | M W. | NPY-2@10 | V1a@1.0 | V1b@1.0 | V2@1.0 |
|---|---|---|---|---|---|---|
| | | | | Binding IC$_{50}$ ($\mu$M) or % Inh @ $\mu$M | | |
| 119 | 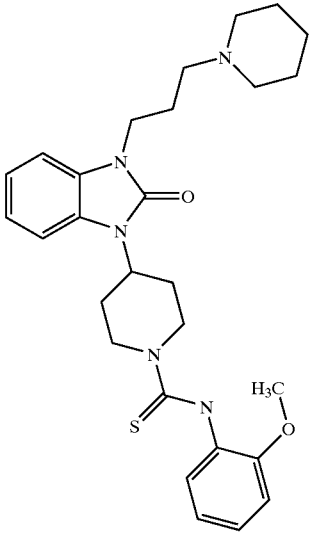 | 507.699 | 13% | 0.061 (48%) | 29% | 19% |
| 120 | 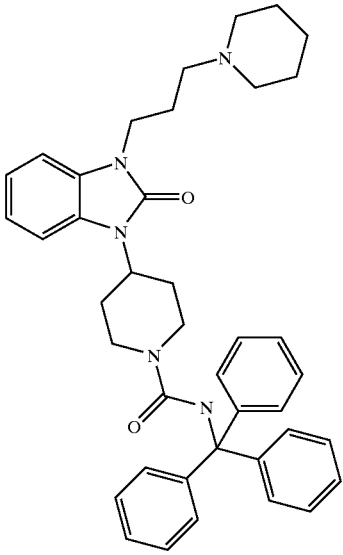 | 627.829 | 100% | 20% | 25% | 20% |
| 121 | 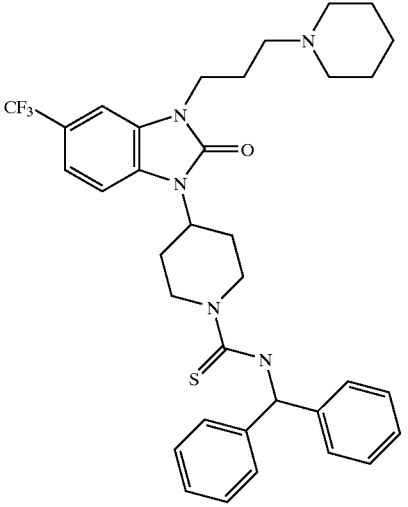 | 635.795 | — | 0.33 | 39% | 3% |

TABLE I-continued
| No. | Structure | M.W. | NPY-2@10 | V1a@1.0 | V1b@1.0 | V2@1.0 |
|-----|-----------|------|----------|---------|---------|--------|
| 122 | 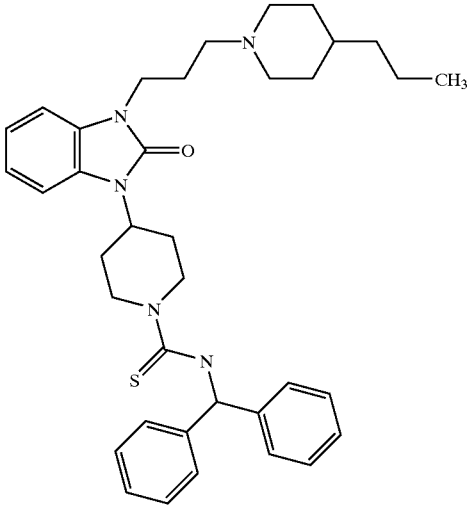 | 609.878 | — | 0.052 | 0.250 (70%) | 0 |
| 123 | 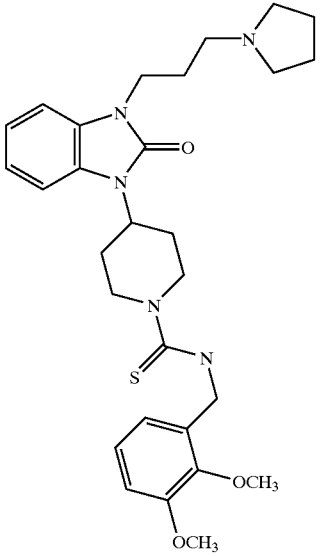 | 537.725 | — | 0.43 | 31% | 2% |
| 124 | 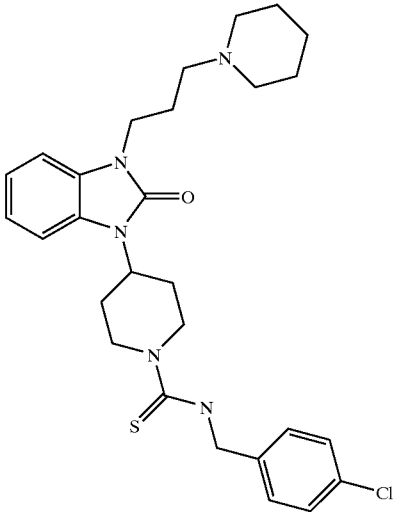 | 526.145 | — | 0.029 | 44% | 3% |
Binding IC$_{50}$ ($\mu$M) or % Inh @ $\mu$M TABLE I-continued

| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 125 | | 483.721 | — | 0.39 | 35% | 0% |
| 126 | | 643.8955 | — | 0% | 0% | 0% |

TABLE I-continued

| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 127 | | 567.7979 | — | 0.022 | 45% | 0% |
| 128 | | 443.6563 | — | 12% | 31% | 0% |

TABLE I-continued

| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 129 | 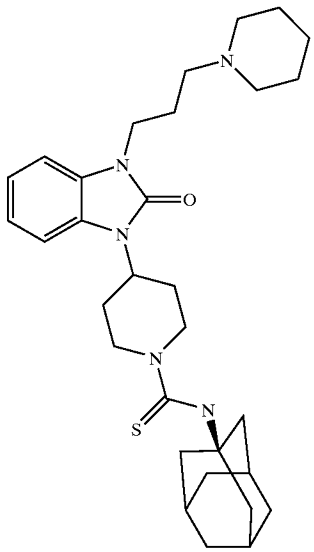 | 535.7965 | — | 0.073 | 53% | 3% |
| 130 | 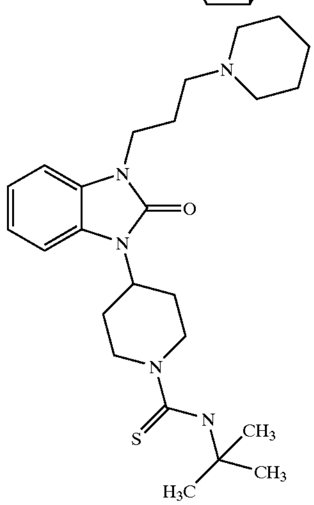 | 457.6831 | — | 19% | 26% | 2% |
| 131 | 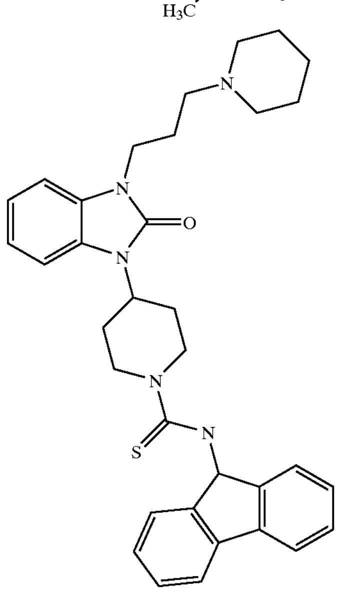 | 565.7821 | — | 0.048 | 62% | 0% |

TABLE I-continued
| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 132 | 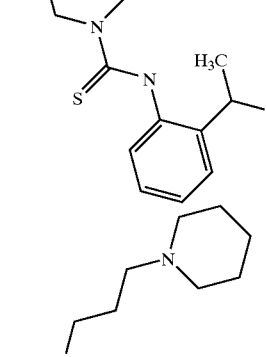 | 519.7539 | — | 66% | 55% | 0% |
| 133 | 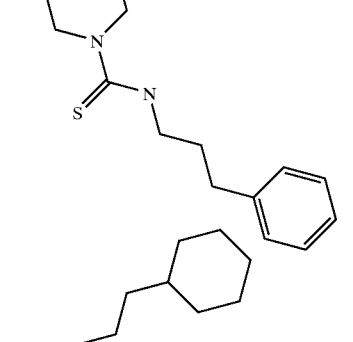 | 519.7539 | — | 0.069 | 42% | 4% |
| 134 | 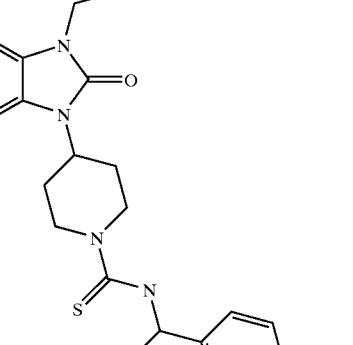 | 566.8098 | — | 0.45 | 37% | 0% |

TABLE I-continued

| No. | Structure | M W. | Binding IC₅₀ (μM) or % Inh @ μM | | | |
| --- | --- | --- | --- | --- | --- | --- |
| | | | NPY-2@10 | V1a@1.0 | V1b@1.0 | V2@1.0 |
| 135 | 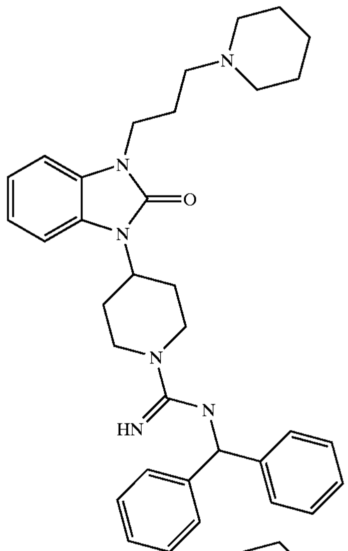 | 550.7468 | — | 24% | 0% | 0% |
| 136 | 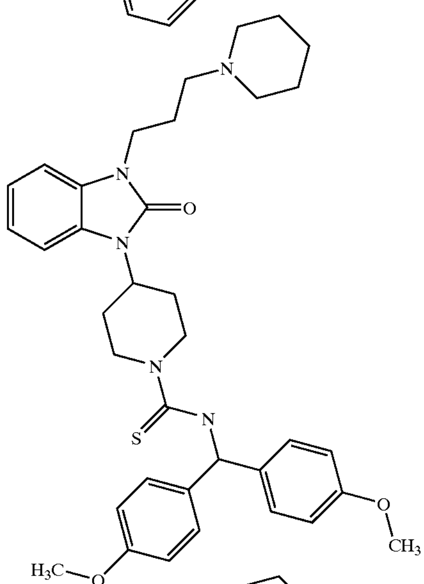 | 627.8495 | — | 0.079 | 50% | 25% |
| 137 | 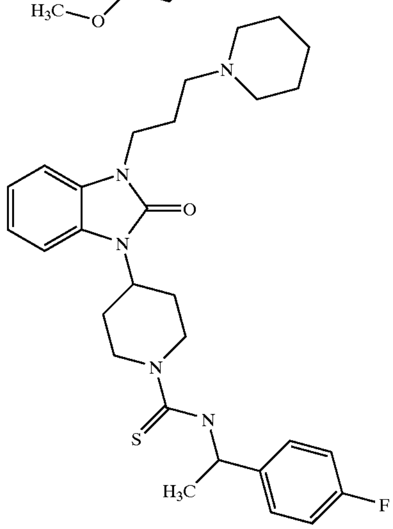 | 523.7172 | — | 0.091 | 41% | 0% |

TABLE I-continued
| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 138 | 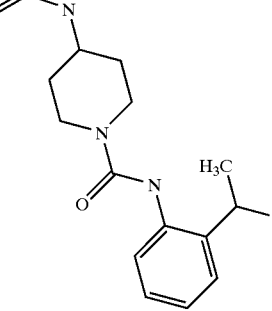 | 503.6869 | — | 58% | 21% | 0% |
| 139 | 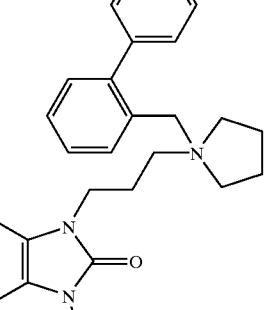 | 704.9578 | — | 0% | 0% | 0% |

TABLE I-continued
| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 140 | 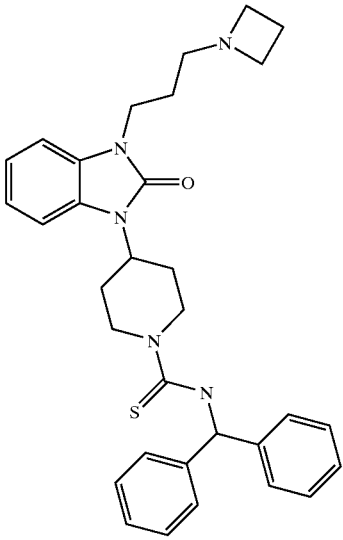 | 539.7443 | — | 59% | 28% | 0% |
| 141 | 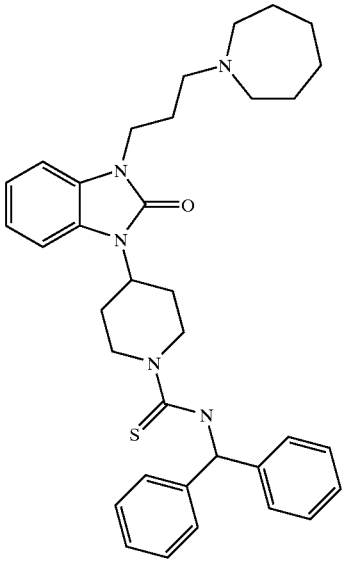 | 581.8247 | — | 83% | 29% | 0% |

TABLE I-continued
| No. | Structure | M W. | Binding IC$_{50}$ ($\mu$M) or % Inh @ $\mu$M | | | |
| | | | NPY-2@10 | V1a@1.0 | V1b@1.0 | V2@1.0 |
|---|---|---|---|---|---|---|
| 142 | 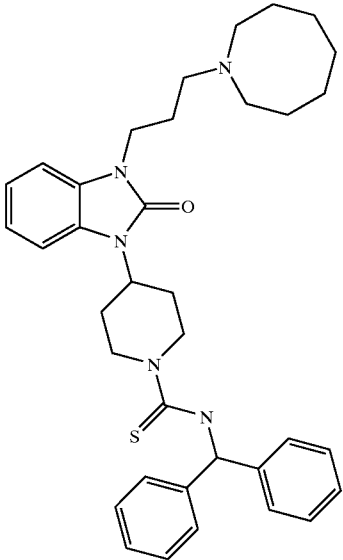 | 595.8515 | — | 0.068 | 56% | 4% |
| 143 | 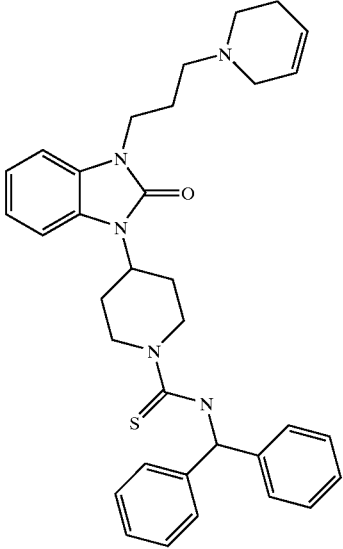 | 565.7821 | — | 0.041 | 65% | 8% |

TABLE I-continued
| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 144 | 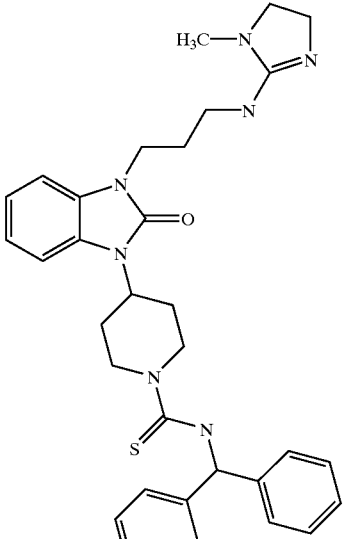 | 581.7851 | — | 0.395 | 31% | 2% |
| 145 | 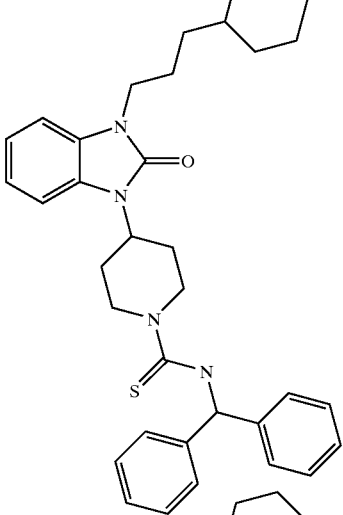 | 566.8098 | — | 0.45 | 37% | 0% |
| 146 | 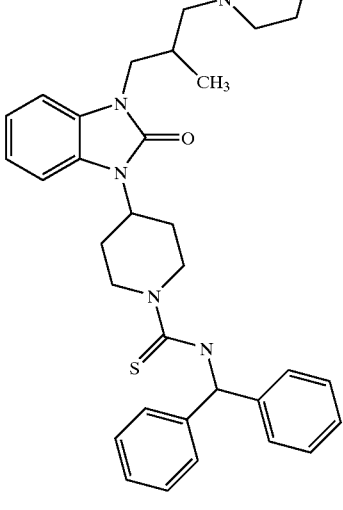 | 581.8247 | — | 85%@1 15%@0.5 | 33% | 0% |

TABLE I-continued
| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 147 | 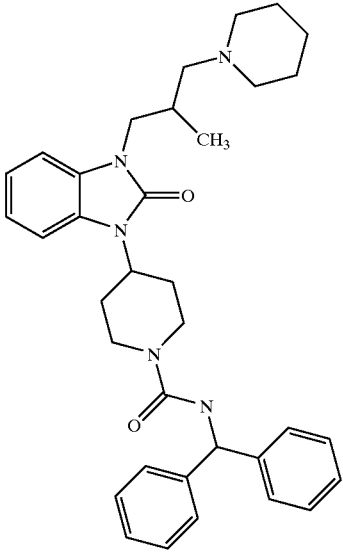 | 565.7577 | — | 0.44 | 27% | 1 |
| 148 | 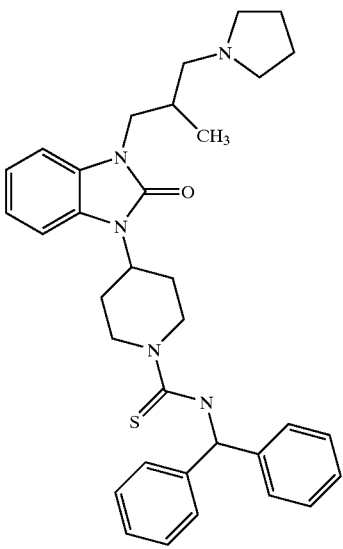 | 567.7979 | — | 0.053 | 40% | 1 |

TABLE I-continued
| No. | Structure | M W. | NPY-2@10 | V1a@1.0 | V1b@1.0 | V2@1.0 |
|-----|-----------|------|----------|---------|---------|--------|
| | | | Binding IC$_{50}$ ($\mu$M) or % Inh @ $\mu$M | | | |
| 149 | 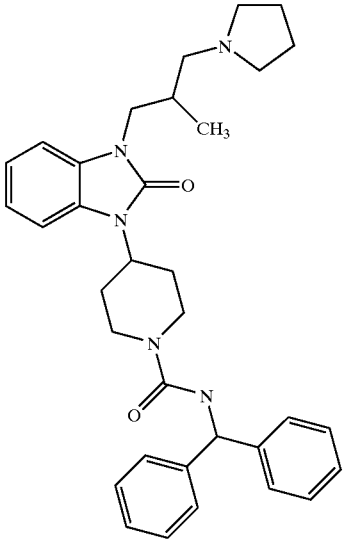 | 551.7309 | — | 0.042 | 44% | 0% |
| 150 | 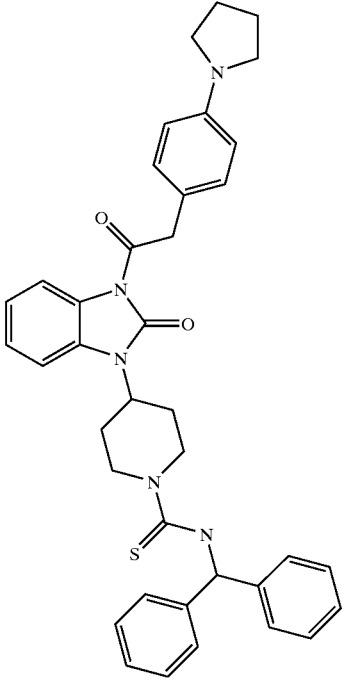 | 629.8251 | — | 38% | 16% | 0% |

TABLE I-continued

| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 151 | | 489.6601 | — | 62% | 37% | 0% |
| 152 | | 549.7151 | — | 0.23 | 38% | 2% |

TABLE I-continued
| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 153 | 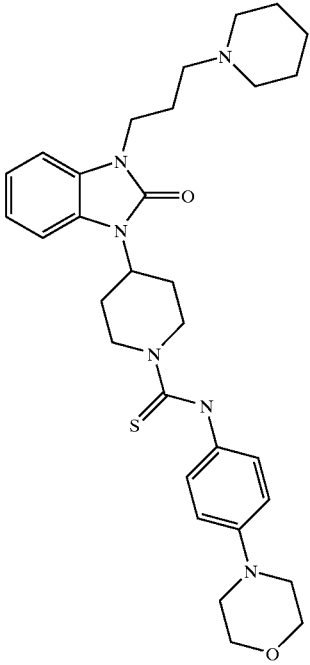 | 562.7788 | — | 0% | 0% | 0% |
| 154 | 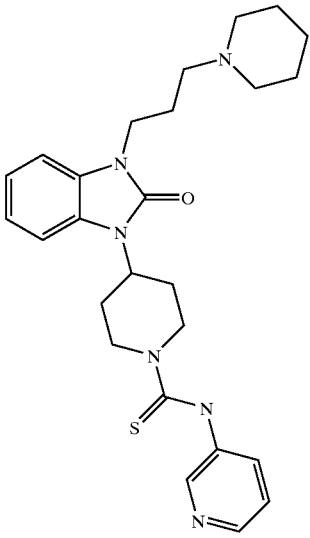 | 478.6616 | — | 7% | 0% | 3% |

TABLE I-continued
| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 155 | 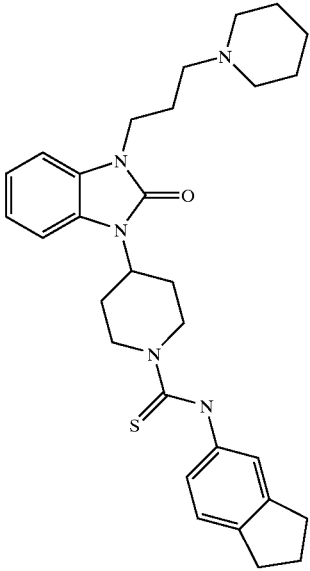 | 517.7381 | — | 28% | 10% | 5% |
| 156 | 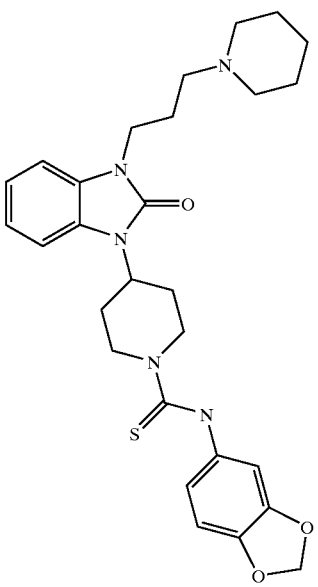 | 521.6825 | — | 0.45 | 22% | 3% |

TABLE I-continued
| No. | Structure | M.W. | NPY-2@10 | V1a@1.0 | V1b@1.0 | V2@1.0 |
|-----|-----------|------|----------|---------|---------|--------|
| 157 | 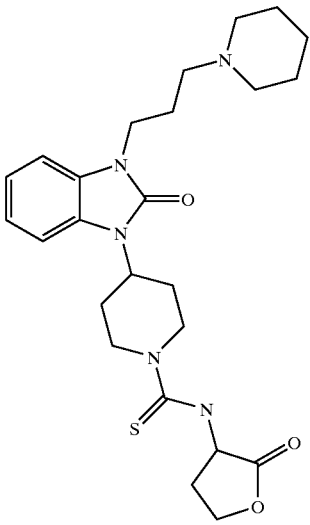 | 485.6495 | — | 5% | 0% | 6% |
| 158 | 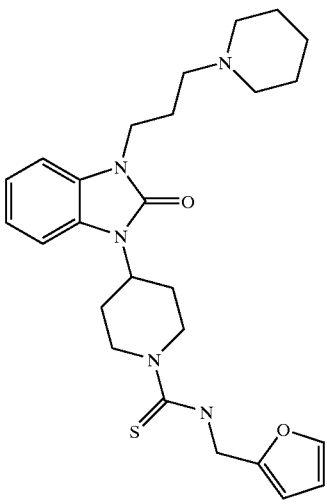 | 481.6615 | — | 55% | 18% | 42% |
| 159 | 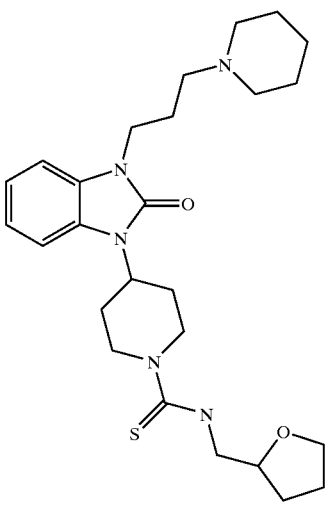 | 485.6931 | — | 2% | 10% | 0% |
Binding IC$_{50}$ ($\mu$M) or % Inh @ $\mu$M TABLE I-continued

| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 160 | 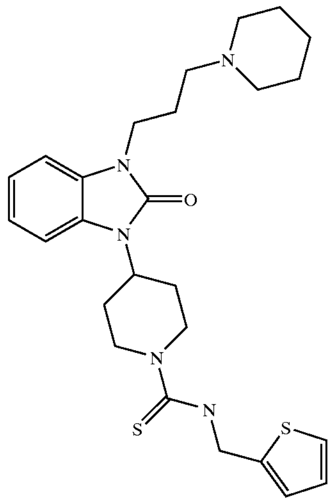 | 497.7285 | — | 0.23 | 27% | 0% |
| 161 | 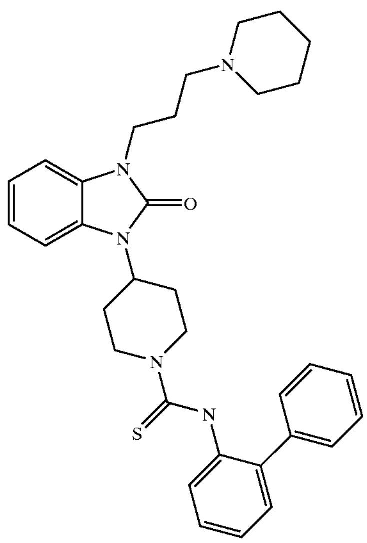 | 553.7711 | — | 0.108 | 40% | 2% |
| 162 | 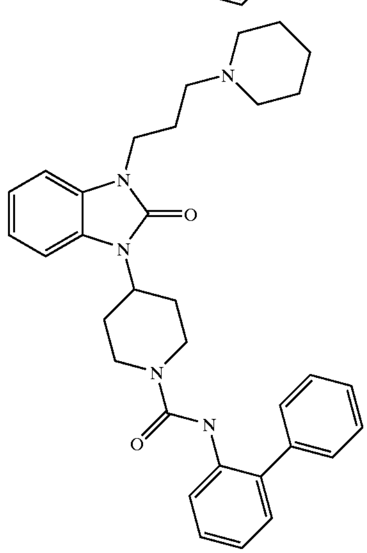 | 537.7041 | — | 0.117 | 26% | 4% |

TABLE I-continued

| No. | Structure | M W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 163 | 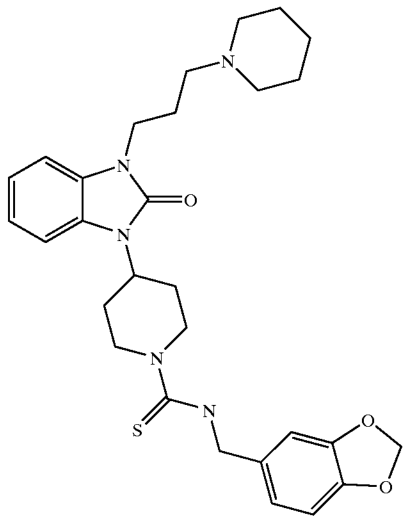 | 535.7093 | — | 0.15 | 27% | 0% |
| 164 | 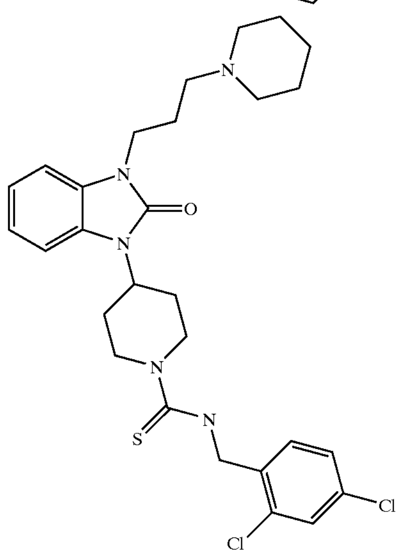 | 560.5905 | — | 0.086 | 35% | 5% |
| 165 | 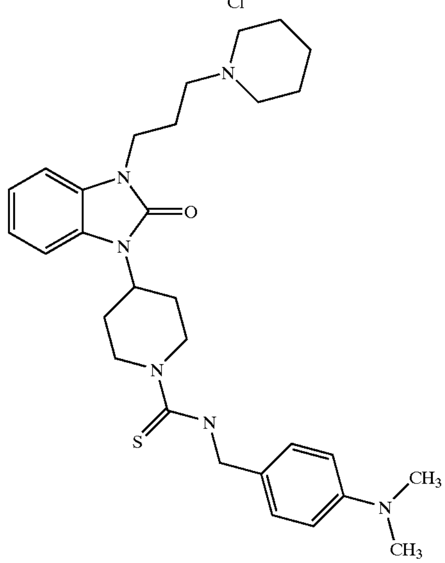 | 534.7688 | — | 40% | 20% | 3% |

TABLE I-continued

| No. | Structure | M.W. | Binding IC$_{50}$ ($\mu$M) or % Inh @ $\mu$M | | | |
| --- | --- | --- | --- | --- | --- | --- |
| | | | NPY-2@10 | V1a@1.0 | V1b@1.0 | V2@1.0 |
| 166 | 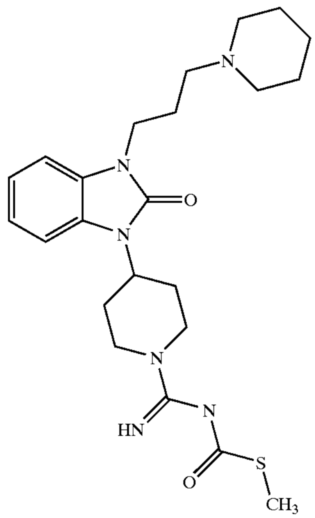 | 458.628 | — | 5% | 16% | 19% |
| 167 | 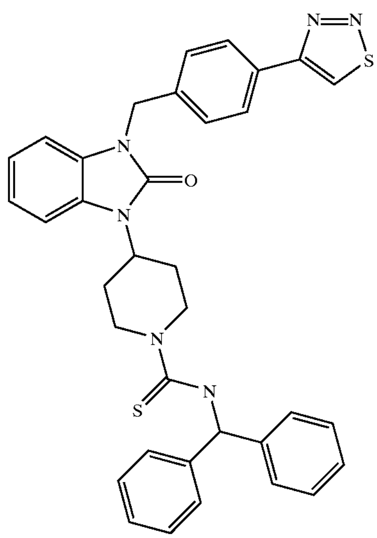 | 616.81 | — | 12% | 1% | 8% |
| 168 | 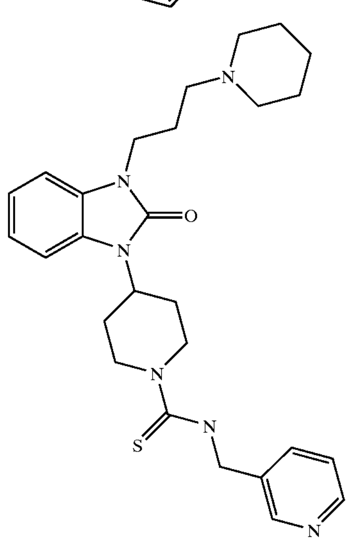 | 492.688 | — | 62% | 25% | 2% |

TABLE I-continued
| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 169 | 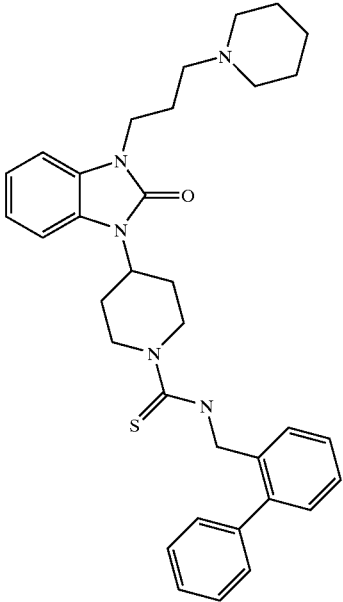 | 567.798 | — | 0.012 | 1.72 | 4% |
| 170 | 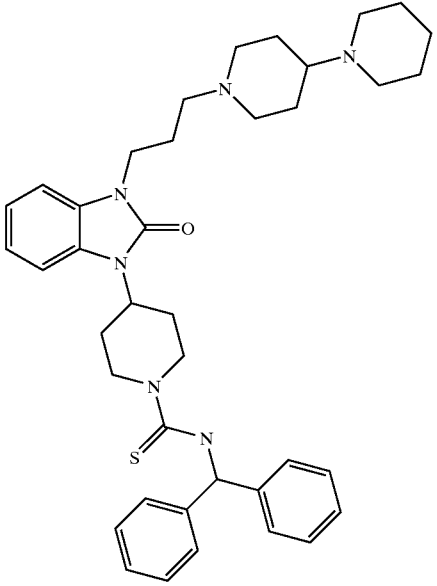 | 650.931 | — | 0.080 | 0.68 | 6% |

TABLE I-continued

| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 171 | | 565.758 | — | 65% | 33% | 2% |
| 172 | | 581.825 | — | 0.072 | 0.70 | 6% |

TABLE I-continued
| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 173 | 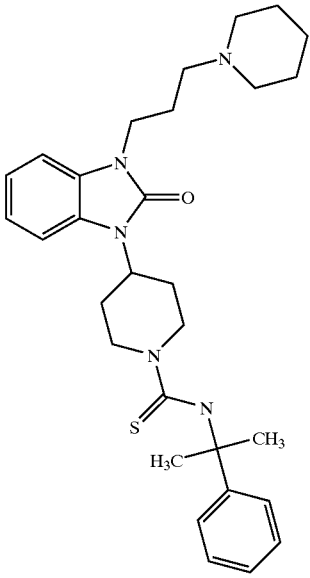 | 519.754 | — | 0.25 | 43% | 0% |
| 174 | 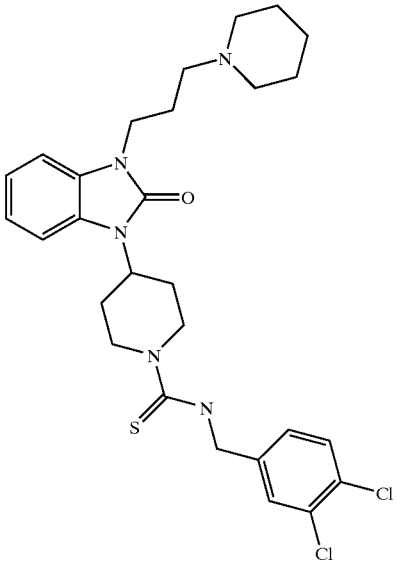 | 560.591 | — | 0.42 | 34% | 0% |

TABLE I-continued

| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 175 | | 567.754 | — | 61% | 23% | — |
| 176 | | 581.781 | — | 59% | 31% | — |

TABLE I-continued
| No. | Structure | M W. | Binding IC$_{50}$ ($\mu$M) or % Inh @ $\mu$M | | | |
| | | | NPY-2@10 | V1a@1.0 | V1b@1.0 | V2@1.0 |
| --- | --- | --- | --- | --- | --- | --- |
| 177 | 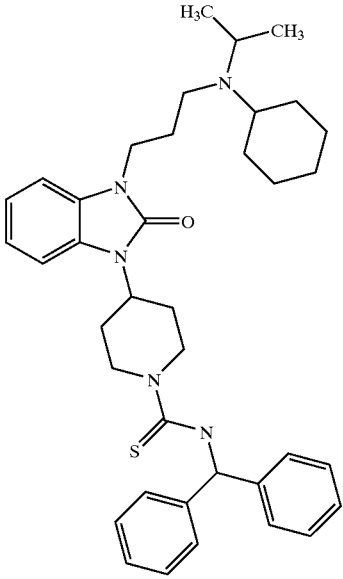 | 623.905 | — | 0.147 | 31% | — |
| 178 | 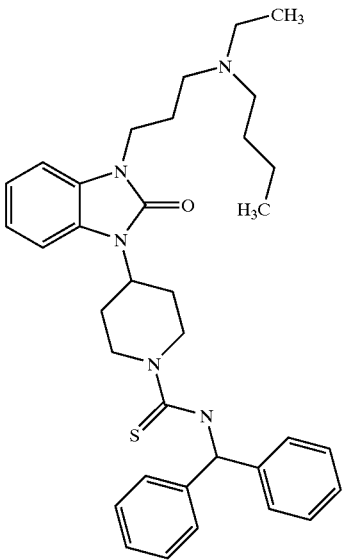 | 583.841 | — | 0.090 | 43% | — |

TABLE I-continued
| | | | Binding IC$_{50}$ ($\mu$M) or % Inh @ $\mu$M | | | |
|---|---|---|---|---|---|---|
| No. | Structure | M W. | NPY-2@10 | V1a@1.0 | V1b@1.0 | V2@1.0 |
| 179 | 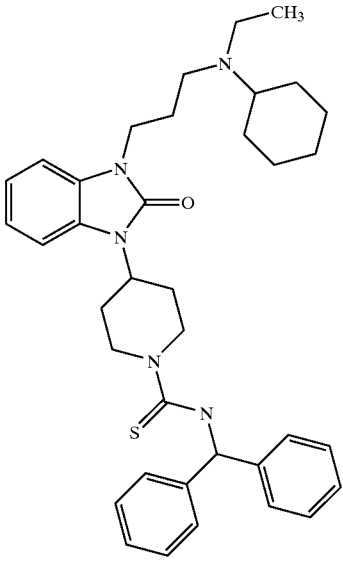 | 609.878 | — | 0.145 | 65% | — |
| 180 | 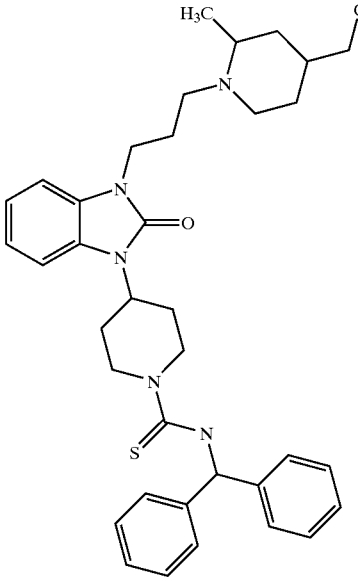 | 609.878 | — | 0.067 | 58% | — |

TABLE I-continued

| No. | Structure | M.W. | NPY-2@10 | V1a@1.0 | V1b@1.0 | V2@1.0 |
|-----|-----------|------|----------|---------|---------|--------|
| | | | Binding IC$_{50}$ ($\mu$M) or % Inh @ $\mu$M | | | |
| 181 | (structure) | 581.825 | — | 0.023 | 0.15 | — |

EXAMPLE 138

V1a, V1b or V2 Functional Assay

HEK-293 cells were grown in DMEM media supplemented with 10% FBS and glutamine (Gibco BRL, Grand Island, N.Y.). Once transfected the cells were passed biweekly by trypsinization and seeded into 96 well plates at 33,000 cells per well. HEK-293 were transfected with human V1a, V1b or V2 DNA using DMRIE-C reagent from Life Technologies, Inc., Grand Island, N.Y. Cells were tested for their responsiveness to vasopressin 48 hours after transfection. Stable lines were generated by selecting cells grown in culture media containing geneticin (500 $\mu$g/ml, Life Technologies).

The accumulation of cAMP was measured in transfected HEK-293 expressing the human V2 receptor. The cells were cultured 4–7 days in 96-well plates. On the day of assay, cells were washed twice in assay media (DMEM/F12 containing 0.1% BSA). The cells were treated with the test compound for 5 minutes and then given AVP (1 nM) in assay media containing 1 mM isobutylmethylxanthine. After 5 minutes, 0.5 N HCl was added to disrupt the cells and solubilize cAMP. The cAMP content of 20 $\mu$l of the cell lysate in each well was measured using cAMP Flashplates (NEN Life Sciences). Data are expressed as pmol cAMP/well. While the assay is optimized to detect and quantitate antagonistic activity, agonistic activity would also be apparent at the higher concentrations of test compounds.

Intracellular calcium mobilization was measured in HEK-293 cells transfected to express either human V1a, oxytocin or V1b receptors. Cells were plated into black 96-well Packard Clear-View plates 4 to 7 days prior to use. The cells were loaded with fluo-3 AM (Molecular Probes, Inc., Eugene, Oreg.) in buffer (25 mM Hepes, 125 mM NaCl, 1 gm/l glucose, 0.1% BSA, 5 mM KCl, 0.5 mM CaCl$_2$, 0.5 mM MgCl$_2$, pH 7.45) containing Pluronic (Molecular Probes) Cells were incubated with 5 $\mu$M fluo-3 AM for 1 hour shielded from light at room temperature. Intracellular fluorescence was measured using FLIPR (fluorometric imaging plate reader; Molecular Devices, Inc., Sunnyvale, Calif.). The FLIPR protocol called for images to be collected at one second intervals with 50 $\mu$l of the test compound added after the initial 10 images. An additional 70 images were then taken to detect any compound agonistic activity. FLIPR then added 50 $\mu$l of agonist peptide and collected a final 40 images for quantitating compound antagonistic activity. V1a- and V1b-expressing HEK cells were challenged with 1 nM and 0.5 nM AVP, respectively. Oxytocin-expressing HEK cells were challenged with 0.5 nM oxytocin (Peninsula Labs).

The data from the cAMP accumulation and the calcium mobilization assays are expressed as IC$_{50}$ values as determined from dose response curves.

Table II below sets forth the vasopressin V1a, V1b receptor cell-based functional activity of some compounds of the instant invention.

TABLE II

| Compound No. | Cell-Based Functional activity (IC$_{50}$ in $\mu$M or % Inh. @ $\mu$M) | | |
|---|---|---|---|
| | V1a | V1b | V2 |
| 35 | 0.458 | 9.99 | 0.623 |
| 42 | 0.81 | 0% @ 30 | 0% @ 10 |
| 55 | 0.139 | 0.318 | 22.8 |
| 57 | 0.482 | 16.84 | 0% @ 30 |
| 58 | 1.43 | 0% @ 30 | 0% @ 30 |
| 59 | 0.24 | 6.61 | 0% @ 30 |
| 62 | 0.69 | 0 @ 30 | — |
| 63 | 0.31 | 8.06 | — |
| 64 | 0.14 | 12.1 | — |
| 65 | 0.46 | 21.0 | — |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I)

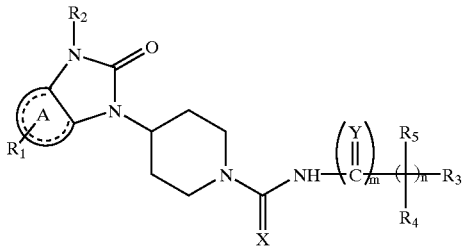

wherein

A is $C_{6-10}$ aryl or $C_{5-10}$ heteroaryl having 0–4 heteroatoms selected from N, O, and S;

X is selected from S, O, NH, and NCN;

Y is S or O;

$R_1$ is 1–3 groups selected from hydrogen, alkyl, substituted alkyl, halogen, nitro, methylenedioxy, nitrile, —$OR^a$, —$NHR^a$, —$NR^aR^b$, —$S(O)_pR^a$, —$N(R^a)C(O)R^b$, —$C(O)OR^a$, —$C(O)NR^aR^b$, —$SO_2NR^aR^b$, —$N(R^a)SO_2R^b$, $N(R^a)C(O)NR^a$, and $NHCOOR^a$, wherein $R^a$ and $R^b$ are independently selected from the group consisting of hydrogen, alkyl, substituted alkyl, aryl, substituted aryl, heterocyclyl, substituted heterocyclyl, heteroaryl, and substituted heteroaryl;

$R^2$ is selected from hydrogen, alkyl, and substituted alkyl;

$R^3$ is selected from hydrogen, alkyl, substituted alkyl, benzhydryl, aryl, substituted aryl, heteroaryl, substituted heteroaryl, heterocyclyl, substituted heterocyclyl, —$C(O)OR^c$, and —$C(O)NR^cR^d$, wherein $R^c$ and $R^d$ are independently selected from hydrogen, alkyl, substituted alkyl, aryl, substituted aryl, heteroaryl, substituted heteroaryl, heterocyclyl, and substituted heterocyclyl, or $NR^cR^d$ may be taken together to form a group selected from heteroaryl, substituted heteroaryl, heterocyclyl, and substituted heterocyclyl;

$R_4$ and $R_5$ are independently selected from hydrogen, alkyl, alkyl substituted with aryl or heteroaryl, phenyl, substituted phenyl, or $R_4$ and $R_5$ are non-existent when n is 0;

p is from 0 to 2;

n is 0 or 1; and m is 0 or 1, with the proviso that when m is 0, X is O, and $R_3$ is selected from heteroaryl, substituted heteroaryl, —$C(O)OR^c$, and —$C(O)NR^cR^d$ wherein $R^c$ and $R^d$ are independently selected from alkyl, substituted alkyl, aryl, substituted aryl, heteroaryl, substituted heteroaryl, heterocyclyl, and substituted heterocyclyl, or $NR^cR^d$ may be taken together to form a group selected from heteroaryl, substituted heteroaryl, heterocyclyl, and substituted heterocyclyl, then n is 0;

or an optical isomer, enantiomer, diastereomer, racemate thereof, or a pharmaceutically acceptable salt thereof.

2. The compound of claim 1 wherein X is selected from S, O, and NH.

3. The compound of claim 1 wherein A is phenyl or substituted phenyl.

4. The compound of claim 3 wherein X is S or NH.

5. The compound of claim 1 wherein $R_2$ is alkyl substituted with one or more groups selected from cycloalkyl, aryl, —$NHC(NH)NR^cR^d$, —$NR^cR^d$, —$C(O)OR^c$, —$OR^c$, —$NHC(O)R^c$, and —$C(O)NR^cR^d$, wherein $R^c$ and $R^d$ are independently selected from hydrogen, alkyl, substituted alkyl, aryl, substituted aryl, heteroaryl, substituted heteroaryl, heterocyclyl, and substituted heterocyclyl, or $NR^cR^d$ may be taken together to form a group selected from aryl, substituted aryl, heteroaryl, substituted heteroaryl, heterocyclyl, and substituted heterocyclyl.

6. The compound of claim 5 wherein X is S and $R_3$ is aryl or substituted aryl.

7. The compound of claim 1 wherein X is O and n is 0.

8. The compound of claim 1 wherein $R_2$ is hydrogen and X is S.

9. The compound of claim 8 wherein $R_4$ and $R_5$ are independently phenyl or substituted phenyl.

10. The compound of claim 1 which is 1-piperidinecarbothioamide, 4-[3-[3-(cyclohexylmethylamino)propyl]-2,3-dihydro-2-oxo-1H-benzimidazol-1-yl]-N-(diphenylmethyl)-.

11. The compound of claim 1 which is 1-piperidinecarbothioamide, 4-[3-[3-(3,5-dimethyl-1-piperidinyl)propyl]-2,3-dihydro-2-oxo-1H-benzimidazol-1-yl]-N-(diphenylmethyl)-.

12. The compound of claim 1 which is 1-piperidinecarbothioamide, 4-[2,3-dihydro-2-oxo-3-[3-(1-piperidinyl)propyl]-1H-benzimidazol-1-yl]-N-(diphenylmethyl)-.

13. The compound of claim 1 which is 1-piperidinecarbothioamide, 4-[3-[3-(dimethylamino)propyl]-2,3-dihydro-2-oxo-1H-benzimidazol-1-yl]-N-(diphenylmethyl)-.

14. The compound of claim 1 which is 1-piperidinecarbothioamide, 4-[2,3-dihydro-2-oxo-3-[3-(1-pyrrolidinyl)propyl]-1H-benzimidazol-1-yl]-N-(diphenylmethyl)-.

15. The compound of claim 1 which is 1-piperidinecarbothioamide, 4-[3-(2-aminoethyl)-2,3-dihydro-2-oxo-1H-benzimidazol-1-yl]-N-(diphenylmethyl)-.

16. The compound of claim 1 which is 1-piperidinecarbothioamide, 4-[3-[3-[(aminoiminomethyl)amino]propyl]-2,3-dihydro-2-oxo-1H-benzimidazol-1-yl]-N-(diphenylmethyl)-.

17. The compound of claim 1 which is 1-piperidinecarbothioamide, 4-[3-(4-aminobutyl)-2,3-dihydro-2-oxo-1H-benzimidazol-1-yl]-N-(diphenylmethyl)-.

18. The compound of claim 1 which is 1-piperidinecarbothioamide, 4-[3-(4-aminobutyl)-2,3-dihydro-2-oxo-1H-benzimidazol-1-yl]-N-[(4-chlorophenyl)phenylmethyl]-.

19. The compound of claim 1 which is 1-piperidinecarbothioamide, 4-[3-(3-aminopropyl)-2,3-dihydro-2-oxo-1H-benzimidazol-1-yl]-N-(diphenylmethyl)-.

20. The compound of claim 1 which is 1-piperidinecarbothioamide, 4-[3-[2-(diethylamino)ethyl]-2,3-dihydro-2-oxo-1H-benzimidazol-1-yl]-N-(diphenylmethyl)-.

21. The compound of claim 1 which is phenylalanine, N-[[4-(2,3-dihydro-2-oxo-1H-benzimidazol-1-yl)-1-piperidinyl]carbonothioyl]-, methyl ester.

22. The compound of claim 1 which is 1-piperidinecarbothioamide, 4-(2,3-dihydro-2-oxo-1H-benzimidazol-1-yl)-N-(1,2-diphenylethyl)-.

23. A pharmaceutical composition comprising a compound according to claim 1 and a pharmaceutically acceptable carrier.

* * * * *